(12) United States Patent
Dolle et al.

(10) Patent No.: US 7,544,676 B2
(45) Date of Patent: *Jun. 9, 2009

(54) SULFAMOYL BENZAMIDES AND METHODS OF THEIR USE

(75) Inventors: Roland E. Dolle, King of Prussia, PA (US); Karin Worm, East Windsor, NJ (US)

(73) Assignee: Adolor Corporation, Exton, PA (US)

(*) Notice: Subject to any disclaimer, the term of this patent is extended or adjusted under 35 U.S.C. 154(b) by 17 days.

This patent is subject to a terminal disclaimer.

(21) Appl. No.: 11/558,332

(22) Filed: Nov. 9, 2006

(65) Prior Publication Data

US 2008/0058302 A1 Mar. 6, 2008

Related U.S. Application Data

(60) Provisional application No. 60/735,571, filed on Nov. 10, 2005.

(51) Int. Cl.

| | | |
|---|---|---|
| A61K 31/195 | (2006.01) | |
| A61K 31/34 | (2006.01) | |
| A61K 31/397 | (2006.01) | |
| A61K 31/40 | (2006.01) | |
| A61K 31/445 | (2006.01) | |
| A61K 31/535 | (2006.01) | |
| A61P 25/00 | (2006.01) | |
| C07C 307/02 | (2006.01) | |
| C07D 265/30 | (2006.01) | |

(52) U.S. Cl. .............. 514/210.01; 514/563; 514/238.8; 514/237.8; 514/323; 514/424; 514/470; 544/144; 544/158; 546/201; 548/484; 548/542; 548/950

(58) Field of Classification Search .............. 514/231.2, 514/608, 210.01, 237.8, 323, 424, 470, 563; 544/158, 144; 564/86, 88; 546/201; 548/484, 548/542, 950

See application file for complete search history.

(56) References Cited

U.S. PATENT DOCUMENTS

| 4,029,787 A | 6/1977 | Sturm et al. ............ 424/248.53 |
| 4,550,179 A * | 10/1985 | Perrot et al. ................. 548/571 |
| 7,297,796 B2 * | 11/2007 | Dolle et al. ................. 546/205 |

FOREIGN PATENT DOCUMENTS

| WO | 2004/017920 A2 | 3/2004 |
| WO | WO2005/066126 A1 | 7/2005 |
| WO | WO2006/044654 A2 | 4/2006 |

OTHER PUBLICATIONS

Cannabinoid receptors, Wikipedia.*
Cited ref—STN preliminary search—11558332.*

Bhargava, H.N., et al., "Effect of nitric oxide synthases inhibition on tolerance to the analgesic action of D-Pen$^2$, D-Pen$^5$ enkephalin and morphine in the mouse," *Neuropeptides*, 1996, 30(3), 219-223.

Bilsky, E.J., et al., "Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice," *J. Pharmacol. Exp. Ther.*, 1996, 277(1), 484-490.

Cheng, Y.-C., et al., "Relationship between the inhibition constant ($K_i$) and the concentration of inhibitor which causes 50 percent inhibition ($I_{50}$) of an enzymatic reaction," *Biochem. Pharmacol.*, 1973, 22, 3099-3108.

Compton, D.R., et al., "Cannabinoid behaviors: specific versus non-specific actions," *Marijuana: An International Research Report*, 1987, 7, 213-218.

Costa, A. et al., "AlPO$_4$-Al$_2$O$_3$ Promoted Cyclodehydration of Diols," *Synthetic Communications*, 1987, 17(11), 1373-1376.

DeLean, A.P., et al., "Simultaneous analysis of families of sigmoidal curves: application to bioassay, radioligand assay, and physiological dose-response curves," *Am. J. Physiol.*, 1978, 235, E97-E102.

Dourish, C.T., et al., "Enhancement of morphine analgesia and prevention of morphine tolerance in the rat by the cholecystokinin antagonist L-364,718," *Eur. J. Pharmacol.*, 1988, 147, 469-472.

Flippin, L.A. et al., "A Convenient Method for the Reduction of Ozonides to Alcohols with Borane-Dimethyl Sulfide Complex," *Journal of Organic Chemistry*, 1989, 54(6), 1430-2.

Gill, E.W., et al., "Brain levels of $\Delta^1$-tetrahydrocannabinol and its metabolites in mice-correlation with behaviour, and the effect of the metabolic inhibitors SKF 525A and piperonyl butoxide," *Biochem. Pharmacol.*, 1972, 21, 2237-2248.

Gill, E.W., et al., "Preliminary experiments on the chemistry and pharmacology of cannabis," *Nature*, 1970, 228, 134-136.

Howlett, A.C., et al., "International union of pharmacology. XXVII.. Classification of cannabinoid receptors," *Pharmacological Reviews*, 2002, 54(2), 161-202.

Idris, A.I., et al., "Regulation of bone mass, bone loss and osteoclast activity by cannabinoid receptors," *Nature Medicine*, 2005, 11(7), 774-779.

(Continued)

*Primary Examiner*—Rei-Tsang Shiao
*Assistant Examiner*—Yong Chu
(74) *Attorney, Agent, or Firm*—Feldman Gale, P.A.; David A. Cherry

(57) ABSTRACT

Novel sulfamoyl benzamide compounds, pharmaceutical compositions containing the sulfamoyl benzamide compounds, and methods of their pharmaceutical use are disclosed. In certain embodiments, the sulfamoyl benzamide compounds are agonists and/or ligands of cannabinoid receptors and may be useful, inter alia, for treating and/or preventing pain, gastrointestinal disorders, inflammation, auto-immune diseases, ischemic conditions, immune-related disorders, hypertension, neurological disorders, and neurodegenerative diseases, for providing cardioprotection against ischemic and reperfusion effects, for inducing apoptosis in malignant cells, for inhibiting mechanical hyperalgesia associated with nerve injury, and as an appetite stimulant.

74 Claims, No Drawings

OTHER PUBLICATIONS

Iwamura, H., et al., "In vitro and in vivo pharmacological characterization of JTE-907, a novel selective ligand for cannabinoid $CB_2$ receptor," *J. Pharm. Exp. Ther.*, 2001, 296(2), 420-425.

Jain, K.K., "A guide to drug evaluation for chronic pain," *Emerging Drugs*, 2000, 5(2), 241-257.

Lavey, B.J., et al., "Triaryl bis-sulfones as a new class of cannabinoid CB2 receptor inhibitors: identification of a lead and initial SAR studies," *Bioorg. & Med. Chem. Lett*, 2005, 15, 783-786.

Lunn, C.A., et al., "Triaryl bis-sulfones as a new class of cannabinoid CB2 receptor inhibitors: identification of a lead and initial biological characterization," *ICRS 15th Annual Symposium of the Cannabinoids*, Clearwater Beach, FL, Jun. 24-27, 2005, p. 3 Abstract.

Malan, T.P., Jr., et al., "$CB_2$ cannabinoid receptor agonists: pain relief without psychoactive effects?," *Curr. Opin. Pharm.*, 2003, 3, 62-67.

Mao, J., et al., "Oral administration of dextromethorphan prevents the development of morphine tolerance and dependence in rats," *Pain*, 1996, 67, 361-368.

Mechoulam, R., (Ed.), *Cannabinoids as therapeutic agents*, CRC Press, Boca Raton, FL, Jul, 1986, Chapter 1, 1-19.

Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.

Olah, G.A., et al., "Synthetic Methods and Reactions: 99[1]. Preparation of Cyclic Ethers over Superacidic Perfluorinated Reinsulfonic Acid (Nafion-H) Catalyst," *Synthesis*, 1981, 474-476.

Parolaro, D., "Presence and functional regulations of cannabinoid receptors in immune cells," *Life Sci.*, 1999, 65(6/7), 637-644.

Pertwee, R.B., "Pharmacology of cannabinoid receptor ligands," *Current Medicinal Chem.*, 1999, 6, 635-664.

Pertwee, R.G., "Cannabinoid receptors and pain," *Prog. in Neurobiol.*, 2001, 63, 569-611.

Pertwee, R.G., "The ring test: a quantitative method for assessing the 'cataleptic' effect of cannabis in mice," *Br. J. Pharmacology*, 1972, 46, 753-763.

Rice, A.S., "Cannabinoids and pain," *Curr. Opin, Investig. Drugs*, 2001, 2(3), 399-414.

Rinaldi-Carmona, M., et al., "SR 144528, the first potent and selective antagonist of the CB2 cannabinoid receptor," *J. of Pharmacology & Experimental Therapeutics*, 1998, 284(2), 644-650.

* cited by examiner

SULFAMOYL BENZAMIDES AND METHODS OF THEIR USE

CROSS REFERENCE TO RELATED APPLICATION

This application claims the benefit of U.S. Provisional Application Ser. No. 60/735,571 filed Nov. 10, 2005, the disclosure of which is incorporated herein by reference in its entirety.

FIELD OF THE INVENTION

This invention relates to novel sulfamoyl benzamide compounds, pharmaceutical compositions containing such compounds, and uses thereof. More particularly, the present invention relates to novel sulfamoyl benzamide compounds that may affect the cannabinoid receptor system and thus may be useful, inter alia, as agonists or antagonists of cannabinoid receptors.

BACKGROUND OF THE INVENTION

*Cannabis sativa* preparations have long been known as therapeutic agents to treat various diseases (Mechoulam, R., "Cannabinoids as Therapeutic Agents" CRC Press, Boca Raton, Fla. 1-19, 1986). The native active constituent, delta 9-tetrahydrocannabinol ($\Delta^9$-THC), is prescribed today, under the generic name dronabinol, as an anti-emetic and for enhancement of appetite, mainly in AIDS patients. However, separation between the clinically undesirable psychotropic effects and the therapeutically desirable effects on the peripheral nervous systems, the cardiovascular system, the immune and endocrine system is problematic. The discovery of two cannabinoid receptors, CB1 and CB2, has helped to elucidate the diverse cannabinoid effects.

The CB1 receptor has been cloned from rat, mouse, and human tissues and exhibits 97-99% amino acid sequence identity across species. The CB2 receptor exhibits 48% homology with the CB1 receptor (A. C. Howlett et al. *Pharmacological Reviews* 2002, 54, 161-202). The structures of both receptors are consistent with seven transmembrane G-protein coupled receptors. In addition, both receptors exert their effect by negative regulation of adenylyl cyclase activity through pertussis toxin-sensitive GTP-binding proteins. They have been shown to activate the mitogen activated protein kinase (MAPK) in certain cell types (Parolaro, D., *Life Sci.* 1999, 65, 637-44).

The CB1 receptor is expressed mainly in the central nervous systems (CNS) and to a lesser extent in other tissues including, for example, gastrointestinal tissues, immune cells, reproductive organs, heart, lung, urinary bladder and adrenal gland. The CB2 receptor is expressed mostly in peripheral tissue associated with immune functions including, for example, macrophages, B cells, T cells and mast cells, as well as in peripheral nerve terminals (Pertwee, R. G., *Prog. Neurobiol.* 2001, 63, 569-611). The central distribution pattern of CB1 receptors accounts for several unwanted pharmacological properties of cannabinoids, such as impaired cognition and memory, altered control of motor function, and psychotropic and other neurobehavioral effects. CB1 receptors are also found on pain pathways in brain, spinal cord and at the peripheral terminals of primary sensory neurons (A. S. Rice, *Curr. Opin. Investig. Drugs* 2001 2(3), 399-414).

CB1 knockout mice have been shown to be unresponsive to cannabinoids in behavioral assays providing molecular evidence that the psychotropic effects, including sedation, hallucinations and antinociception are manifested through the activation of the CB1 receptor, present primarily in the CNS. Analysis of the CB2 knockout mouse has corroborated the evidence for the function of CB2 receptors in modulating the immune system. The CB2 receptor does not affect immune cell development and differentiation as determined by FACS analysis of cells from the spleen, lymph node and thymus from CB2 knockout mice. Further studies in these mice have shown that the immunosuppressive effects of $\Delta^9$-THC are mediated by the CB2 receptor.

Some cannabinoid receptor agonists have been shown to produce potent antinociception with equivalent efficacy to morphine in animal models of acute pain, persistent inflammatory pain, and neuropathic pain. They have also been reported to induce a number of unwanted CNS side effects. Furthermore, the known cannabinoid receptor agonists are in general highly lipophilic and insoluble in water. There is thus a need for cannabinoid receptor agonists with improved properties for uses as therapeutic agents.

Known CB1 cannabinoid receptor agonists produce a characteristic profile of in vivo effects in mice, including suppression of spontaneous activity, antinociception, hypothermia, and catalepsy. Measurement of these four properties, commonly referred to as the tetrad test, has played a key role in establishing the structure-activity relationship of cannabinoids and cannabimimetics acting at CB1 receptors. Catalepsy in mice is indicative of CB1 activation and predictive of cannabinoid psychoactivity. Pertwee showed a correlation between catalepsy in the ring test in mice and the previously validated dog static ataxia model (R. G. Pertwee, *Br. J. Pharmacology* 1972, 46, 753-763). Therefore, catalepsy in mice is viewed as excellent predictor of CNS effects in humans (D. R. Compton, *Marijuana: An International Research Report* 7, 213-218, 1987; E. W. Gill and G. Jones, *Biochem. Pharmacol.* 21, 2237-2248, 1972; E. W. Gill et al. *Nature* 228, 134-136, 1970).

Efforts have been made to separate therapeutic effects from undesirable CNS side effects by increasing the selectivity for the CB2 receptor, thereby leading to efforts to design compounds with selectivity for the CB2 receptor over the CB1 receptor. These compounds would be predicted to lack side effects even if they penetrate the CNS because they would not activate the CB1 receptors in the CNS (Malan, T. Philip, Jr. et al. "CB2 cannabinoid receptor agonists: pain relief without psychoactive effects?" *Curr Op. Pharm.* 2003, 3(1), 62-67; WO2004/017920).

Recent studies have identified CB2 selective inverse agonists with antiedema effects in vivo (Iwamura et al., *J. Pharm. Exp. Ther.* 2001, 420-425; Lavey et al. *Bioorg. Med. Chem. Lett.* 2005, 783-786), suggesting an involvement of CB2 selective inverse agonists in inflammatory processes and the pharmacological efficacy of CB2 inverse agonists by themselves.

Lunn, et al. (ICRS 15th Annual Symposium of the Cannabinoids, Clearwater Beach, Fla., Jun. 24-27, 2005) have reported that CB2 receptor-selective inverse agonists are capable of altering cellular chemotaxis mediated by either cannabinoids or chemokines, both in vivo and in vitro. They have reported that administration of these compounds can decrease allergic eosinophilia in animal models for asthma.

Other research has shown that pharmacological antagonists of CB1 and CB2 receptors prevented ovariectomy-induced bone loss in vivo and caused osteoclast inhibition in vitro by promoting osteoclast apoptosis and inhibiting production of several osteoclast survival factors. These studies show that the CB1 receptor has a role in the regulation of bone mass and ovariectomy-induced bone loss and that CB1- and CB2-selective cannabinoid receptor antagonists are a new class of osteoclast inhibitors that may be of value in the treatment of osteoporosis and other bone diseases (A. I Idris, et al., *Nature Medicine*, 2005, 11(7), 774-79).

There is considerable interest in developing new cannabimimetic compounds possessing preferentially high affinity for the CB2 receptor. Such compounds that preferentially stimulate the CB2 receptor, directly or indirectly, may provide clinically useful effects without unwanted effects on the subject's central nervous system and can offer a rational therapeutic approach to a variety of disease states. The present invention is directed to these and other important ends.

SUMMARY OF THE INVENTION

Accordingly, the present invention is directed, in part, to novel sulfamoyl benzamide compounds which may be modulators, agonists, and/or antagonists of cannabinoid receptors and which thus may be useful, inter alia, for the treatment of diseases or disorders which are associated with the cannabinoid receptor system.

Specifically, in certain embodiments, the present invention relates to compounds of formula I:

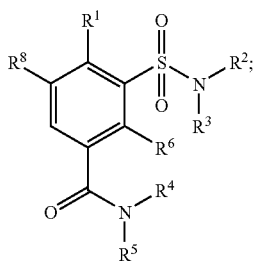

wherein:

$R^1$ is $SR^x$ or $NR^yR^z$;

each $R^x$, $R^y$ and $R^z$ is independently H, alkyl, cycloalkyl, cycloalkylalkyl, aryl, aralkyl, heterocycloalkyl, heterocycloalkylalkyl, heteroaryl, or heteroaralkyl; or $R^y$ and $R^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H, alkyl, or aryl;

$R^5$ is:

$$\left(\begin{array}{c}R^a\\R^b\end{array}\right)_r Z \quad \text{or} \quad \begin{array}{c}\text{alkyl}\\R^a\\\text{aryl}\end{array};$$

or $R^4$ and $R^5$, taken together with the nitrogen atom to which they are attached, form a 5- to 8-membered heterocyclic ring;

Z is $$\begin{array}{c}R^e\\R^d\\R^c\end{array},$$

a 1 or 2 heteroatom containing heteroaryl, or a 1 or 2 heteroatom containing heterocycloalkyl, wherein each heteroatom of said heteroaryl or heterocycloalkyl group is independently selected from the group consisting of N, N($R^{11}$), O, and S;

each $R^a$ and $R^b$ is independently H or alkyl;

$R^c$ is H, alkyl, or aryl;

$R^d$ and $R^e$ are each independently H or alkyl, with the proviso that at least two of $R^c$, $R^d$, and $R^e$ are other than H; or $R^d$ and $R^e$, taken together with the carbon atom to which they are attached, form a carbocyclic or heterocyclic ring; or $R^c$, $R^d$, and $R^e$, taken together with the carbon atom to which they are attached, form a bicycloalkyl, tricycloalkyl, heterobicyclic, or heterotricyclic ring;

$R^6$ and $R^8$ are each independently H, F, Cl, Br, or alkyl;

each $R^9$ is independently H, alkyl, aryl, —C(=O)—$R^{11}$, —C(=O)—$OR^{11}$, —[C($R^{11}$)($R^{11}$)]$_s$—C(=O)—$OR^{11}$, —SO$_2R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

with the provisos that:

(1) when $R^d$ and $R^e$ are each independently H or alkyl, then $R^c$ is H or alkyl; and (2) when $R^c$ is aryl, then $R^d$ and $R^e$, taken together with the carbon atom to which they are attached, form a carbocyclic or heterocyclic ring;

or a pharmaceutically acceptable salt thereof.

In other embodiments, the present invention also relates, in part, to compounds of formula II:

wherein:
R$^w$ is H, alkyl, cycloalkyl, cycloalkylalkyl, aryl, aralkyl, heterocycloalkyl, heterocycloalkylalkyl, heteroaryl, or heteroaralkyl;
R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;
R$^4$ is H or alkyl;
R$^5$ is:

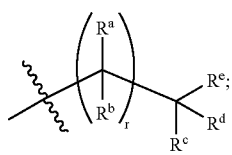

each R$^a$, R$^b$, R$^c$, R$^d$, and R$^e$ is independently H or alkyl, provided that at least two of R$^c$, R$^d$, and R$^e$ are other than H; or R$^d$ and R$^e$, taken together with the carbon atom to which they are attached, form a carbocyclic ring; or R$^c$, R$^d$, and R$^e$, taken together with the carbon atom to which they are attached, form a bicycloalkyl or tricycloalkyl ring;
R$^6$, R$^7$, and R$^8$ are each independently H, F, Cl, Br, or alkyl;
each R$^9$ is independently H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;
each R$^{10}$ is independently H, alkyl, or aryl;
each R$^{11}$ is independently H or alkyl;
r is 0, 1, 2, or 3; and
s is 1, 2, 3, or 4;
or a pharmaceutically acceptable salt thereof.

The present invention is directed, in part, to pharmaceutical compositions, comprising:
a pharmaceutically acceptable carrier; and a compound of formula I:

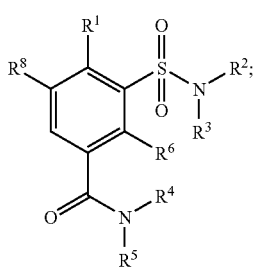

I wherein:
R$^1$ is SR$^x$ or NR$^y$R$^z$;
each R$^x$, R$^y$ and R$^z$ is independently H, alkyl, cycloalkyl, cycloalkylalkyl, aryl, aralkyl, heterocycloalkyl, heterocycloalkylalkyl, heteroaryl, or heteroaralkyl; or R$^y$ and R$^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;
R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;
R$^4$ is H, alkyl, or aryl;
R$^5$ is:

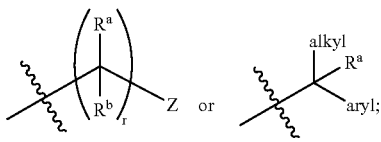

or R$^4$ and R$^5$, taken together with the nitrogen atom to which they are attached, form a 5- to 8-membered heterocyclic ring;
Z is

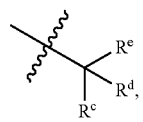

a 1 or 2 heteroatom containing heteroaryl, or a 1 or 2 heteroatom containing heterocycloalkyl, wherein each heteroatom of said heteroaryl or heterocycloalkyl group is independently selected from the group consisting of N, O, or S;
each R$^a$ and R$^b$ is independently H or alkyl;
R$^c$ is H, alkyl, or aryl;
R$^d$ and R$^e$ are each independently H or alkyl, with the proviso that at least two of R$^c$, R$^d$, and R$^e$ are other than H; or R$^d$ and R$^e$, taken together with the carbon atom to which they are attached, form a carbocyclic or heterocyclic ring; or R$^c$, R$^d$, and R$^e$, taken together with the carbon atom to which they are attached, form a bicycloalkyl, tricycloalkyl, heterobicyclic, or heterotricyclic ring;
R$^6$ and R$^8$ are each independently H, F, Cl, Br, or alkyl;
each R$^9$ is independently H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;
each R$^{10}$ is independently H, alkyl, or aryl;
each R$^{11}$ is independently H or alkyl;
r is 0, 1, 2, or 3; and
s is 1, 2, 3, or 4;
with the provisos that:
(1) when R$^d$ and R$^e$ are each independently H or alkyl, then R$^c$ is H or alkyl; and
(2) when R$^c$ is aryl, then R$^d$ and R$^e$, taken together with the carbon atom to which they are attached, form a carbocyclic or heterocyclic ring;
or a pharmaceutically acceptable salt thereof.

The present invention is also directed, in part, to methods of binding cannabinoid receptors in a patient in need thereof, comprising the step of:

administering to said patient an effective amount of a compound according to formula I:

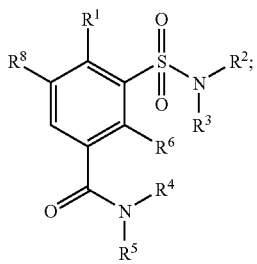

I wherein:

$R^1$ is $SR^x$ or $NR^yR^z$;

each $R^x$, $R^y$ and $R^z$ is independently H, alkyl, cycloalkyl, cycloalkylalkyl, aryl, aralkyl, heterocycloalkyl, heterocycloalkylalkyl, heteroaryl, or heteroaralkyl; or $R^y$ and $R^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H, alkyl, or aryl;

$R^5$ is:

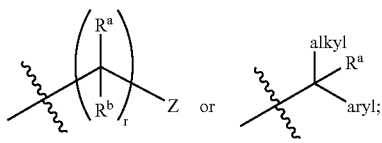

or $R^4$ and $R^5$, taken together with the nitrogen atom to which they are attached, form a 5- to 8-membered heterocyclic ring;

Z is

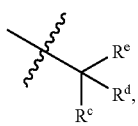

a 1 or 2 heteroatom containing heteroaryl, or a 1 or 2 heteroatom containing heterocycloalkyl, wherein each heteroatom of said heteroaryl or heterocycloalkyl group is independently selected from the group consisting of N, O, or S;

each $R^a$ and $R^b$ is independently H or alkyl;

$R^c$ is H, alkyl, or aryl;

$R^d$ and $R^e$ are each independently H or alkyl, with the proviso that at least two of $R^c$, $R^d$, and $R^e$ are other than H; or $R^d$ and $R^e$, taken together with the carbon atom to which they are attached, form a carbocyclic or heterocyclic ring; or $R^c$, $R^d$, and $R^e$, taken together with the carbon atom to which they are attached, form a bicycloalkyl, tricycloalkyl, heterobicyclic, or heterotricyclic ring;

$R^6$ and $R^8$ are each independently H, F, Cl, Br, or alkyl;

each $R^9$ is independently H, alkyl, aryl, —C(=O)—$R^{11}$, —C(=O)—$OR^{11}$, —[C($R^{11}$)($R^{11}$)]$_s$—C(=O)—$OR^{11}$, —SO$_2R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

with the provisos that:

(1) when $R^d$ and $R^e$ are each independently H or alkyl, then $R^c$ is H or alkyl; and (2) when $R^c$ is aryl, then $R^d$ and $R^e$, taken together with the carbon atom to which they are attached, form a carbocyclic or heterocyclic ring;

or a pharmaceutically acceptable salt thereof.

The invention is also directed to pharmaceutical compositions, comprising:

a pharmaceutically acceptable carrier; and a compound of formula II:

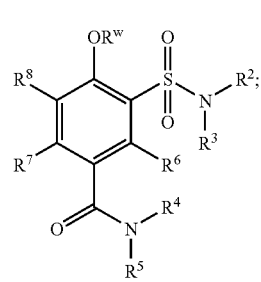

II wherein:

$R^w$ is H, alkyl, cycloalkyl, cycloalkylalkyl, aryl, aralkyl, heterocycloalkyl, heterocycloalkylalkyl, heteroaryl, or heteroaralkyl;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

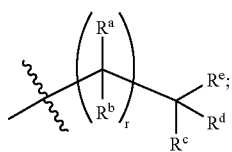

each $R^a$, $R^b$, $R^c$, $R^d$, and $R^e$ is independently H or alkyl, provided that at least two of $R^c$, $R^d$, and $R^e$ are other than H; or $R^d$ and $R^e$, taken together with the carbon atom to which they are attached, form a carbocyclic ring; or $R^c$, $R^d$, and $R^e$, taken together with the carbon atom to which they are attached, form a bicycloalkyl or tricycloalkyl ring;

$R^6$, $R^7$, and $R^8$ are each independently H, F, Cl, Br, or alkyl;

each $R^9$ is independently H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

or a pharmaceutically acceptable salt thereof.

The present invention is further directed to methods of binding cannabinoid receptors in a patient in need thereof, comprising the step of:

administering to said patient an effective amount of a compound according to formula II:

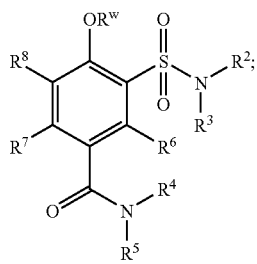

wherein:

$R^w$ is H, alkyl, cycloalkyl, cycloalkylalkyl, aryl, aralkyl, heterocycloalkyl, heterocycloalkylalkyl, heteroaryl, or heteroaralkyl;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

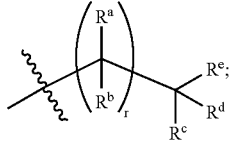

each $R^a$, $R^b$, $R^c$, $R^d$, and $R^e$ is independently H or alkyl, provided that at least two of $R^c$, $R^d$, and $R^e$ are other than H; or $R^d$ and $R^e$, taken together with the carbon atom to which they are attached, form a carbocyclic ring; or $R^c$, $R^d$, and $R^e$, taken together with the carbon atom to which they are attached, form a bicycloalkyl or tricycloalkyl ring;

$R^6$, $R^7$, and $R^8$ are each independently H, F, Cl, Br, or alkyl;

each $R^9$ is independently H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

or a pharmaceutically acceptable salt thereof.

DETAILED DESCRIPTION OF ILLUSTRATIVE EMBODIMENTS

The present invention is generally directed to sulfamoyl benzamide compounds, pharmaceutical compositions containing these compounds, and methods of their pharmaceutical use.

As employed above and throughout the disclosure, the following terms, unless otherwise indicated, shall be understood to have the following meanings.

As used herein, the term "alkyl" refers to an optionally substituted, saturated, straight or branched hydrocarbon having from about 1 to about 20 carbon atoms (and all combinations and subcombinations of ranges and specific numbers of carbon atoms therein), with from about 1 to about 8 carbon atoms, herein referred to as "lower alkyl," being preferred. Alkyl groups include, but are not limited to, methyl, ethyl, n-propyl, isopropyl, n-butyl, isobutyl, sec-butyl, t-butyl, n-pentyl, isopentyl, neopentyl, n-hexyl, isohexyl, 3-methylpentyl, 2,2-dimethylbutyl, and 2,3-dimethylbutyl.

As used herein, the term "cycloalkyl" or "carbocyclic ring" each refers to an optionally substituted, mono-, di-, tri-, or other multicyclic alicyclic ring system having from about 3 to about 20 carbon atoms (and all combinations and subcombinations of ranges and specific numbers of carbon atoms therein). In some preferred embodiments, the cycloalkyl groups have from about 3 to about 8 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

As used herein, "bicycloalkyl" refers to an optionally substituted, alicyclic group having two bridged rings in its structure and having from about 7 to about 20 carbon atoms (and all combinations and subcombinations of ranges and specific numbers of carbon atoms therein), with from about 7 to about 15 carbon atoms being preferred. Exemplary bicycloalkyl-ring structures include, but are not limited to, norbornyl, bornyl, [2.2.2]-bicyclooctyl, cis-pinanyl, trans-pinanyl, camphanyl, iso-bornyl, and fenchyl.

As used herein, "tricycloalkyl" refers to an optionally substituted, alicyclic group having three bridged rings in its structure and having from about 7 to about 20 carbon atoms (and all combinations and subcombinations of ranges and specific numbers of carbon atoms therein), with from about 7 to about 15 carbon atoms being preferred. Exemplary tricycloalkyl-ring structures include, but are not limited to, tricyclo [5.1.2.0$^{2,6}$]decane, 1,7,7-trimethyl tricyclo[2.2.1.0$^{2,6}$]heptane, alpha-santalol, patchouli alcohol, alpha-cedrene, and longifolene.

As used herein, the term "cycloalkylalkyl" refers to an optionally substituted ring system comprising an alkyl radical bearing one or more cycloalkyl substituents, and having from about 6 to about 50 carbon atoms (and all combinations and subcombinations of ranges and specific numbers of carbon atoms therein), with from about 6 to about 10 carbon atoms being preferred, wherein alkyl and cycloalkyl are as previously defined. Non-limiting examples include, for example, cyclopropylmethyl, cyclobutylethyl, cyclopentylpropyl, cyclohexylmethyl, 2-cyclooctyl-1-methylethyl, 2-[4-isopropyl-1-methyl-7-oxa-bicyclo[2.2.1]heptanyl]methyl, 2-[1,2,3,4-tetrahydro-naphthalenyl]ethyl, and adamantylpropyl.

As used herein, the term "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, the term "heterocycloalkyl" and "heterocyclic ring" each refers to an optionally substituted ring system composed of a cycloalkyl radical wherein in at least one of the rings, one or more of the carbon atom ring members is independently replaced by a heteroatom group selected from the group consisting of O, S, N, and NH, wherein cycloalkyl is as previously defined. Heterocycloalkyl ring systems having a total of from about 5 to about 14 carbon atom ring members and heteroatom ring members (and all combinations and subcombinations of ranges and specific numbers of carbon and heteroatom ring members) are preferred. In other preferred embodiments, the heterocyclic groups may be fused to one or more aromatic rings. In certain preferred embodiments, heterocycloalkyl moieties are attached via a ring carbon atom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, thiazolidinyl, piperazinyl, 2-oxo-morpholinyl, morpholinyl, 2-oxo-piperidinyl, piperadinyl, decahydroquinolyl, octahydrochromenyl, octahydro-cyclopenta[c]pyranyl, 1,2,3,4,-tetrahydroquinolyl, 1,2,3,4-tetrahydroquinazolinyl, octahydro-[2]pyridinyl, decahydro-cycloocta[c]furanyl, 1,2,3,4-tetrahydroisoquinolyl, 2-oxo-imidazolidinyl, and imidazolidinyl. In some embodiments, two moieties attached to a heteroatom may be taken together to form a heterocycloalkyl ring, such as when $R^2$ and $R^3$, taken together with the nitrogen atom to which they are attached, form a heterocycloalkyl ring. In certain of these embodiments, 1 or 2 of the heterocycloalkyl ring carbon atoms may be replaced by other moieties which contain either one (—O—, —S—, —N($R^9$)—) or two (—N($R^{10}$)—C(=O)—, or —C(=O)—N($R^{10}$)—) ring replacement atoms. When a moiety containing one ring replacement atom replaces a ring carbon atom, the resultant ring, after replacement of a ring atom by the moiety, will contain the same number of ring atoms as the ring before ring atom replacement. When a moiety containing two ring replacement atoms replaces a ring carbon atom, the resultant ring after replacement will contain one more ring atom than the ring prior to replacement by the moiety. For example, when a piperidine ring has one of its ring carbon atoms replaced by —N($R^{10}$)—C(=O)—, the resultant ring is a 7-membered ring containing 2 ring nitrogen atoms and the carbon of a carbonyl group in addition to 4 other carbon ring atoms ($CH_2$ groups) from the original piperidine ring.

As used herein, the term "heterocycloalkylalkyl" refers to an optionally substituted ring system composed of an alkyl radical having one or more heterocycloalkyl substituents, wherein heterocycloalkyl and alkyl are as previously defined. In some preferred embodiments, the alkyl moieties of the heterocycloalkylalkyl groups have from about 1 to about 3 carbon atoms. Exemplary heterocycloalkyl groups include, but are not limited to, azepanylmethyl, tetrahydrofuranyl-ethyl, hexahydropyrimidinylisobutyl, tetrahydrothienylpropyl, piperidinyl-2,2-dimethylethyl, pyrrolidinylmethyl, isoxazolidinylethyl, isothiazolidinylpropyl, pyrazolidinylmethyl, oxazolidinylbutyl, thiazolidinylisopropyl, piperazinylmethyl, 2-oxo-morpholinylmethyl, morpholinylethyl, 2-oxo-piperidinylethyl, piperadinylmethyl, decahydroquinolyl-ethyl, octahydrochromenylpropyl, octahydro-cyclopenta[c]pyranylbutyl, 1,2,3,4,-tetrahydroquinolylethyl, 1,2,3,4-tetrahydroquinazolinylmethyl, octahydro-[2]pyridinylethyl, decahydro-cycloocta[c]furanylmethyl, 1,2,3,4-tetrahydroisoquinolylmethyl, 2-oxo-imidazolidinylethyl, and imidazolidinylmethyl.

As used herein, the term "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

As used herein, the term "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, the term "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, the term "aralkyl" refers to an optionally substituted ring system comprising an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

As used herein, the term "alkylaralkyl" refers to an optionally substituted ring system comprising an alkyl radical bearing an aralkyl substituent and having from about 6 to about 50 carbon atoms (and all combinations and subcombinations of ranges and specific numbers of carbon atoms therein), with from about 6 to about 10 carbon atoms being preferred, wherein alkyl and aralkyl are as previously defined. Non-limiting examples include, for example, tolylmethyl, bis(isopropylphenyl)methyl, 1-tolyl-1-ethylphenylmethyl, tert-butylphenylethyl, and ortho-methyl-para-butylphenylethyl.

As used herein, the term "alkoxyl" refers to an optionally substituted alkyl-O— group wherein alkyl is as previously defined. In some preferred embodiments, the alkyl moieties of the alkoxy groups have from about 1 to about 4 carbon atoms. Exemplary alkoxy groups include, but are not limited to, methoxy, ethoxy, n-propoxy, i-propoxy, n-butoxy, and heptoxy.

As used herein, the term "aryloxyl" refers to an optionally substituted aryl-O— group wherein aryl is as previously defined. Exemplary aryloxy groups include, but are not limited to, phenoxy and naphthoxy.

As used herein, the term "aralkoxyl" refers to an optionally substituted aralkyl-O— group wherein aralkyl is as previously defined. Exemplary aralkoxy groups include, but are not limited to, benzyloxy, 1-phenylethoxy, 2-phenylethoxy, and 3-naphthylheptoxy.

As used herein, the term "halo" refers to a fluoro, chloro, bromo, or iodo moiety, with fluoro, chloro, or bromo moieties being preferred.

As used herein, the term "heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members (and all combinations and subcombinations of ranges and specific numbers of carbon and heteroatom ring members) are preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached via a carbon or a heteroatom to the rest of the molecule.

As used herein, the term "heteroarylalkyl" refers to an optionally substituted ring system comprising an alkyl radical bearing a heteroaryl substituent, having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, the term "spiroalkyl" refers to an optionally substituted alkylene diradical, both ends of which are bonded to the same carbon atom of the parent group to form a spirocyclic group. The spirocyclic group, as herein defined, has 3 to 20 ring atoms, preferably with 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroarylalkyl, spiroalkyl, heterocycloalkyl, hydroxyl (—OH), alkoxyl, aryloxyl, aralkoxyl, nitro (—NO$_2$), cyano (—CN), amino (—NH$_2$), N-substituted amino (—NHR"), N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), N-substituted aminocarbonyl (—C(=O)NHR"), N,N-disubstituted aminocarbonyl (—C(=O)N(R")R"), thiolato (SR"), sulfonic acid and its esters (—SO$_3$R"), phosphonic acid and its mono-ester (—P(=O)(OR")(OH) and di-esters (—P(=O)(OR")(OR"), —S(=O)$_2$R", —S(=O)$_2$NH$_2$, —S(=O)$_2$NHR", —S(=O)$_2$NR"R", —SO$_2$NHC(=O)R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. Aryl substituents may also include (CH$_2$)$_u$SO$_2$NR"(CH$_2$)$_v$, and (CH$_2$)$_u$CO$_2$NR"(CH$_2$)$_v$, where u and v are, independently, 0 to 3, where the methylene units are attached in a 1,2 arrangement yielding substituted aryls of the type:

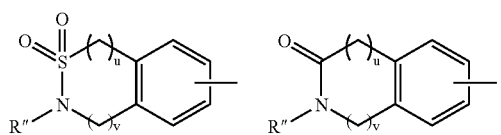

In relation to the aforementioned substituents, each moiety R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl)- groups, for example.

As used herein, the term "cannabinoid" refers to any one of a group of naturally occurring compounds of related structure that may be isolable from *Cannabis sativa*, more commonly known as marijuana, and structurally modified derivatives thereof. Cannabinoids include for example, compounds such as Δ$^9$-tetrahydrocannabinol, Δ$^8$-tetrahydrocannabinol, cannabichromene, cannabicyclol, cannabidiol, cannabielsoin, cannabigerol, cannabinol, cannabitriol, nabilone, and nantradol, and numerous structural variants. Typically cannabinoids are lipophilic and have low solubility in water.

As used herein, the term "cannabimimetic" refers to any of a group of endogenous or exogenous receptor ligands that bind one or more of the receptors bound by cannabinoids and mimic one or more behaviors of cannabinoids while so bound. Examples of endogenous cannabimimetics (also referred to as "endocannabinoids") produced in mammalian tissues include, for example, arachidonoylethanolamide (anandamide), 2-arachidonoyl glycerol, 1(3)-arachidonoyl glycerol, and palmitoylethanolamide. Examples of exogenous cannabimimetics include, for example WIN 55,212-2, CP 55,940, HU-210, and the like. Other examples of exogenous cannbimimetics may be found in publications such as R. B. Pertwee, "Pharmacology of Cannabinoid Receptor Ligands", *Current Medicinal Chemistry*, 1999, 6, 635-664, and A. C. Howlett, et al. "International Union of Pharmacology. XXVII. Classification of Cannabinoid Receptors", *Pharmacological Reviews*, 2002, 54(2), 161-202, the disclosures of which are each hereby incorporated herein by reference in their entireties.

As used herein, the term "antagonist" refers to a compound that binds to a receptor to form a complex that preferably does not elicit any response, in the same manner as an unoccupied receptor, and does not alter the equilibrium between inactive and active receptor.

As used herein, "agonist" refers to a ligand that produces a conformational change in the receptor and alters the equilibrium of the receptor's active and inactive states, which in turn induces a series of events, resulting in a measurable biological response. Agonists include, for example, conventional agonists, which exhibit positive receptor activity, and inverse agonists, which exhibit a negative intrinsic activity.

As used herein, the term "prodrug" refers to compounds that may serve to maximize the amount of active species that reaches the desired site of reaction that are themselves typically inactive or minimally active for the activity desired, but through biotransformation are converted into biologically active metabolites.

As used herein, the term "stereoisomers" refers to compounds that have identical chemical constitution, but differ as regards the arrangement of the atoms or groups in space.

As used herein, the term "partial stereoisomers" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

Asymmetric carbon atoms may be introduced into the molecule depending on the structure of the moiety $R^5$ when $R^a$ and $R^b$ are non-identical or when $R^c$, $R^d$, and $R^e$ are non-identical. For example, when $R^a$ is hydrogen and $R^b$ is other than H, the carbon atom to which $R^a$ is attached is asymmetric.

Other asymmetric centers are contemplated in the present invention. Asymmetric centers are, by convention, present in $R^5$ moieties structure such as those shown below at the ring carbon atoms identified with an asterisk (*). As such, these classes of compounds can exist as

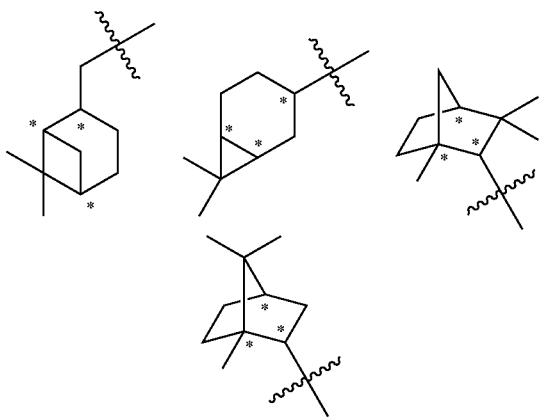

the individual "R" or "S" stereoisomers at each or any of these asymmetric centers, alone or in combination with any other asymmetric centers so formed in the compound to provide single enantiomers, any of the possible racemic mixtures of isomers or diastereomeric mixtures thereof, and all are contemplated as within the scope of the present invention.

As used herein, the term "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, the term "hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer >1) including, for example, dihydrates ($R.2H_2O$), trihydrates ($R.3H_2O$), and the like, or hemihydrates, such as, for example, $R.n_{1/2}H_2O$, $R.n_{1/3}H_2O$, $R.n_{1/4}H_2O$ and the like wherein n is an integer.

As used herein, the term "solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n (solvent)) wherein n is an integer >1) including, for example, disolvates (R.2(solvent)), trisolvates (R.3(solvent)), and the like, or hemisolvates, such as, for example, $R.n_{1/2}$(solvent), $R.n_{1/3}$(solvent), $R.n_{1/4}$(solvent) and the like wherein n is an integer. Solvents herein include mixed solvents, for example, methanol/water, and as such, the solvates may incorporate one or more solvents within the solvate.

As used herein, the term "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

As used herein, the term "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

As used herein, the term "effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the binding of cannabinoid receptors (for example, in connection with the treatment and/or prevention of pain), wherein the treatment or prevention comprises, for example, agonizing the activity thereof by contacting cells, tissues or receptors with compounds of the present invention. Thus, for example, the term "effective amount," when used in connection with cannabinoids, for example, for the treatment of pain, refers to the treatment and/or prevention of the painful condition. The term "effective amount", when used in connection with the present cannabinoid receptor agonist compounds, refers to the treatment, reduction and/or prevention of side effects typically associated with cannabinoids including, for example, such side effects as those hereinabove mentioned.

As used herein, the term "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio.

As used herein, the term "in combination with", "combination therapy" and "combination products" refer, in certain embodiments, to the concurrent administration to a patient of cannabinoids and the compounds of the formula I or II. When administered in combination, each component may be administered at the same time or sequentially in any order at different points in time. Thus, each component may be administered separately but sufficiently closely in time so as to provide the desired therapeutic effect.

As used herein, the term "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

The term "treatment" as used herein includes preventative (e.g., prophylactic), curative or palliative treatment and "treating" as used herein also includes preventative, curative and palliative treatment.

As used herein, the term "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs,* 5(2), 241-257 (2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, pain caused by rheumatoid arthritis, migraine, allodynia, and the like.

As used herein, the term "patient" refers to animals, including mammals, preferably humans.

As used herein, the term "side effect" refers to a consequence other than the one(s) for which an agent or measure is used, as the adverse effects produced by a drug, especially on a tissue or organ system other then the one sought to be benefited by its administration. In the case, for example, of cannabinoids, the term "side effect" may refer to such conditions as, for example, psychotropic effects, such as confusion, anxiety, panic, distortion of perception, fantasizing, sedation, inner unrest, irritability and insomnia, sweating, rhinorrhoea, loose stools, hiccups, dry mouth, tachycardia, ataxia, dizziness, orthostatic hypotension, and anorexia.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

Accordingly, the present invention is directed, in part, to a new class of cannabinoid receptor modulator compounds, preferably sulfamoyl benzamide compounds, which may be highly useful in connection with the binding of cannabinoid receptors. Compounds binding cannabinoid receptors may agonize and/or antagonize the receptors. In situations where a cannabimimetic compound or ligand agonizes one or more cannabinoid receptors, the resultant binding is believed to trigger an event or series of events in the cell that results in a change in the cell's activity, its gene regulation, or the signals that it sends to neighboring cells, similar to that of a cannabinoid. Thus, in some embodiments, compounds of the invention may serve to prevent or treat diseases or disorders in which cannabinoid receptors are implicated. In situations where a cannabimimetic compound or ligand antagonizes one or more cannabinoid receptors, the resultant binding typically occurs comparatively to a greater extent relative to that of the cannabinoid, but does not trigger one or more of the events of signal transduction. Compounds with these properties are highly useful, for example, in connection with the study of functions of cannabinoid receptors, which may result, for example, in the development of new cannabimimetic agonist compounds, such as those, for example, reported in Rinaldi-Carmona, M. et al., *Journal of Pharmacology and Experimental Therapeutics*, 1998, 284(2), 644-650, the disclosure of which is hereby incorporated herein by reference, in its entirety.

Accordingly, in one embodiment, the present invention provides compounds of formula I:

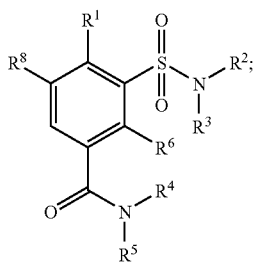

I wherein:

$R^1$ is $SR^x$ or $NR^yR^z$;

each $R^x$, $R^y$ and $R^z$ is independently H, alkyl, cycloalkyl, cycloalkylalkyl, aryl, aralkyl, heterocycloalkyl, heterocycloalkylalkyl, heteroaryl, or heteroaralkyl; or $R^y$ and $R^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H, alkyl, or aryl;

$R^5$ is:

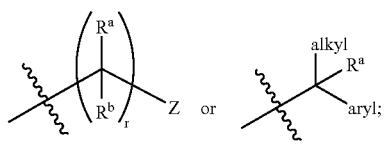

or $R^4$ and $R^5$, taken together with the nitrogen atom to which they are attached, form a 5- to 8-membered heterocyclic ring;

Z is

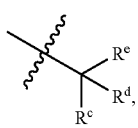

a 1 or 2 heteroatom containing heteroaryl, or a 1 or 2 heteroatom containing heterocycloalkyl, wherein each heteroatom of said heteroaryl or heterocycloalkyl group is independently selected from the group consisting of N, N($R^{11}$), O, and S;

each $R^a$ and $R^b$ is independently H or alkyl;

$R^c$ is H, alkyl, or aryl;

$R^d$ and $R^e$ are each independently H or alkyl, with the proviso that at least two of $R^c$, $R^d$, and $R^e$ are other than H; or $R^d$ and $R^e$, taken together with the carbon atom to which they are attached, form a carbocyclic or heterocyclic ring; or $R^c$, $R^d$, and $R^e$, taken together with the carbon atom to which they are attached, form a bicycloalkyl, tricycloalkyl, heterobicyclic, or heterotricyclic ring;

$R^6$ and $R^8$ are each independently H, F, Cl, Br, or alkyl;

each $R^9$ is independently H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

with the provisos that:

(1) when $R^d$ and $R^e$ are each independently H or alkyl, then $R^c$ is H or alkyl; and (2) when $R^c$ is aryl, then $R^d$ and $R^e$, taken together with the carbon atom to which they are attached, form a carbocyclic or heterocyclic ring;

or a pharmaceutically acceptable salt thereof.

In certain preferred embodiments, the compounds of the invention have the formula I described hereinabove with the provisos that:

(3) $NR^yR^z$ is other than an optionally substituted piperazine ring;

(4) when $R^1$ is S-methyl, $R^2$ is H, $R^3$ is methyl, $R^4$, $R^6$, and $R^8$ are each H, then $R^5$ is other than sec-butyl, tert-pentyl, or 1,3-dimethylbutyl; and (5) when $R^4$ is H and $R^5$ is sec-butyl, or $R^4$ and $R^5$ taken together with the nitrogen atom to which they are connected form a pyrrolidinyl, piperidinyl, 3,5-dimethylpiperidinyl, 4-methylpiperidinyl, 3-[pyrrolidin-2-on-1-yl]propyl, 1,4-dioxa-8-aza-spiro[4.5]decan-8-yl, or optionally N-substituted piperazinyl, and $R^6$, $R^8$, and one of $R^2$ and $R^3$ is H, then the other of $R^2$ and $R^3$ is other than:

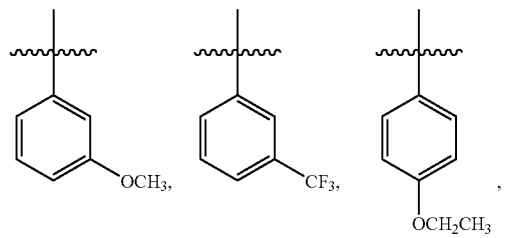

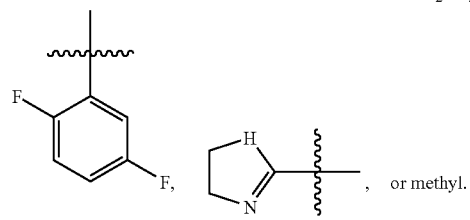

, or methyl.

In certain preferred embodiments of formula I compounds, $R^1$ is $NR^yR^z$.

In some preferred embodiments of formula I compounds, each $R^y$ and $R^z$ is independently H or alkyl, more preferably one of $R^y$ and $R^z$ is H, and still more preferably, $R^y$ and $R^z$ are each H. In certain embodiments where $R^y$ or $R^z$ is alkyl, it is more preferably $C_1$-$C_6$alkyl, still more preferably $C_1$-$C_3$alkyl, yet more preferably optionally substituted methyl or optionally substituted ethyl. In some preferred embodiments the alkyl, preferably $C_2$-$C_3$alkyl, is optionally substituted with amino, alkylamino, dialkylamino, or alkoxy, wherein the alkyl moieties of said alkylamino, dialkylamino, or alkoxy, preferably dialkylamino or alkoxy, are each independently $C_1$-$C_6$alkyl, still more preferably $C_1$-$C_3$alkyl, yet more preferably methyl or ethyl.

In other preferred embodiments of formula I compounds, $R^y$ and $R^z$, when taken together with the nitrogen atom to which they are attached, form a 3- to 8-membered, more preferably 4- to 7-membered, yet more preferably 4- to 6-membered, still more preferably 5- to 6-membered, heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—; more preferably in which 1 of the heterocycloalkyl ring carbon atoms independently may be optionally replaced by —O—, even more preferably is replaced by —O—.

In certain preferred embodiments of formula I compounds, $R^2$ and $R^3$ are each independently alkyl, cycloalkyl, cycloalkylalkyl, aryl, aralkyl, heterocycloalkyl, heterocycloalkylalkyl, heteroaryl, or heteroaralkyl, yet more preferably H or alkyl, even more preferably alkyl. In certain embodiments where $R^2$ or $R^3$ is alkyl, it is more preferably $C_1$-$C_6$alkyl, still more preferably $C_1$-$C_3$alkyl, yet more preferably optionally substituted methyl. In some preferred embodiments, the alkyl is optionally substituted with —C(=O)O-alkyl, wherein the alkyl moiety of said —C(=O)O-alkyl, is $C_1$-$C_6$alkyl, still more preferably $C_1$-$C_3$alkyl, yet more preferably methyl. In other preferred embodiments, $R^2$ or $R^3$ are each independently alkyl or aralkyl. When $R^2$ or $R^3$ is aralkyl it is preferably $C_6$aryl$C_1$alkyl, with benzyl being more preferred.

In certain preferred embodiments of formula I compounds, $R^2$ and $R^3$, when taken together with the nitrogen atom to which they are attached, form a 3- to 8-, more preferably a 4- to 6-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—. In certain embodiments, 1 of the heterocycloalkyl ring carbon atoms independently is replaced by —O—. In other preferred embodiments, the heterocycloalkyl ring is fused to a $C_6$aryl, more preferably phenyl, ring. In some preferred embodiments, $R^2$ and $R^3$ taken together with the nitrogen atom to which they are attached, form a piperidine, pyrrolidine, or morpholine ring, more preferably a piperidine or pyrrolidine ring, each optionally substituted, preferably with hydroxy. In certain other preferred embodiments, $R^2$ and $R^3$ taken together with the nitrogen atom to which they are attached, form a morpholine ring.

In other preferred embodiments of formula I compounds, $R^4$ is H or alkyl, more preferably H. In embodiments wherein $R^4$ is alkyl, it is preferably $C_1$-$C_6$alkyl, with $C_1$-$C_3$alkyl being more preferred.

In some preferred embodiments of formula I compounds, $R^5$ is:

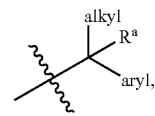

more preferably

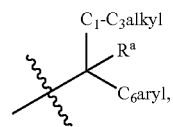

yet more preferably

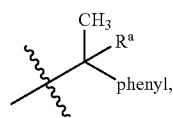

still more preferably

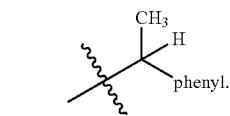

In certain preferred embodiments of formula I compounds, $R^5$ is:

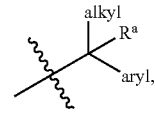

more preferably

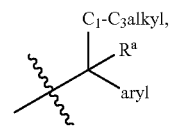

yet more preferably

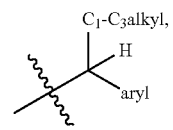

still more preferably

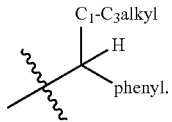

In other preferred embodiments of formula I compounds, $R^5$ is:

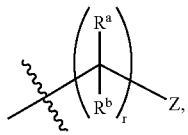

more preferably

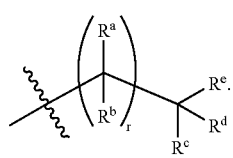

In some preferred embodiments of formula I compounds wherein $R^5$ is:

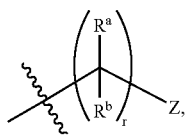

Z is a 1 or 2 heteroatom containing $C_5$-$C_6$heteroaryl, or a 1 or 2 heteroatom containing $C_5$-$C_6$heterocycloalkyl, wherein each heteroatom is independently selected from the group consisting of —N($R^{11}$), O, or S.

In other preferred embodiments of formula I compounds, at least one of $R^a$ and $R^b$ is H, more preferably $R^a$ is H, yet more preferably $R^a$ and $R^b$ are each H. In embodiments where $R^a$ or $R^b$ is alkyl, it is more preferably $C_1$-$C_6$alkyl, still more preferably $C_1$-$C_3$alkyl, yet more preferably optionally substituted methyl.

In certain more preferred embodiments of formula I compounds, $R^5$ is:

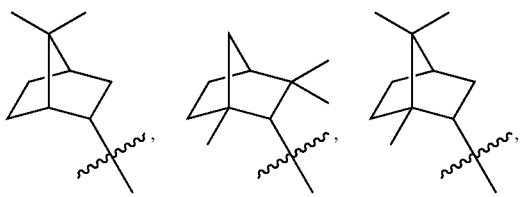

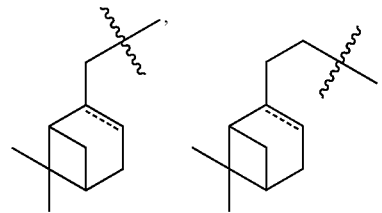

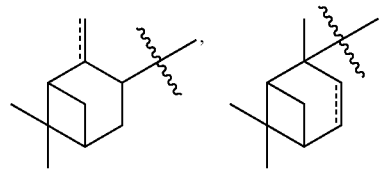

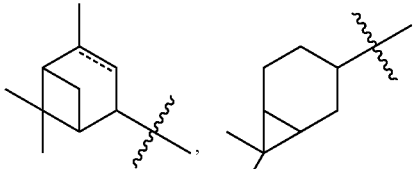

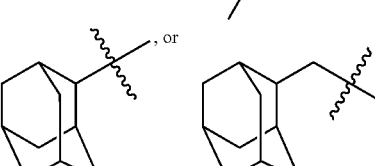

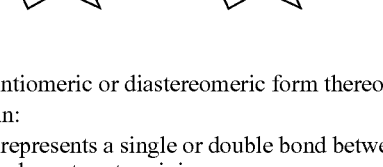

or an enantiomeric or diastereomeric form thereof;
wherein:
 ===== represents a single or double bond between the two bonded carbon atom termini.

In other preferred embodiments of formula I compounds, $R^5$ is:

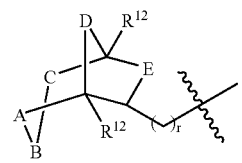

or an enantiomeric or diastereomeric form thereof;
wherein:
A, B, and C are each independently $C(R^{12})(R^{12})$, a bond, or —O—, provided that no more than one of A, B, and C is a bond and provided that no more than one of A, B, and C is —O—;
D and E are each independently $C(R^{12})(R^{12})$ or —O—, provided that at least three of A, B, C, D, and E are other than —O—; and
each $R^{12}$ is independently H or $C_1$-$C_3$alkyl.

In some preferred embodiments of formula I compounds, $R^c$ is H or alkyl, more preferably alkyl. When $R^c$ is alkyl, it is more preferably $C_1$-$C_6$alkyl, still more preferably $C_1$-$C_3$alkyl, with optionally substituted methyl or ethyl being even more preferred. In other embodiments where $R^c$ is aryl, it is preferably $C_6$aryl, with phenyl being more preferred.

In certain preferred embodiments of formula I compounds, at least one of $R^6$ and $R^8$ is H, more preferably, each is H.

In some preferred embodiments of formula I compounds, $R^d$ and $R^e$ are each H or $C_1$-$C_6$alkyl, still more preferably H or $C_1$-$C_3$alkyl. In other preferred embodiments, $R^d$ and $R^e$ are each alkyl, more preferably $C_1$-$C_6$alkyl, still more preferably $C_1$-$C_3$alkyl.

In other preferred embodiments of formula I compounds, $R^d$ and $R^e$, taken together with the carbon atom to which they are attached, form a carbocyclic or heterocyclic ring in which 1 or 2 of the heterocycloalkyl ring carbon atoms independently may each be optionally replaced by —O—, more preferably with the number of ring atoms of the carbocyclic or heterocyclic ring being from about 3 to about 12, yet more preferably about 3 to about 10, with about 5 to about 10 ring atoms being even more preferred. In certain of these embodiments, $R^c$ is aryl or alkyl, more preferably, $C_1$-$C_6$alkyl or $C_6$aryl, still more preferably $C_1$-$C_3$alkyl or phenyl. In certain preferred embodiments, $R^d$ and $R^e$, taken together with the carbon atom to which they are attached, form a monocyclic carbocyclic, bicyclic carbocyclic, monocyclic heterocyclic, or bicyclic heterocyclic ring. In other embodiments, $R^d$ and $R^e$, taken together with the carbon atom to which they are attached, form a bicycloalkyl, tricycloalkyl, heterobicyclic or heterotricyclic ring, more preferably bicycloalkyl or tricycloalkyl, even more preferably wherein the bicycloalkyl ring is substituted with 1-3 alkyl groups.

In certain preferred embodiments of formula I compounds, $R^c$, $R^d$, and $R^e$, taken together with the carbon atom to which they are attached, form a bicycloalkyl, tricycloalkyl, heterobicyclic, or heterotricyclic ring wherein 1 or 2 of the heterobicyclic or heterotricyclic ring carbon atoms independently may each be optionally replaced by —O—, more preferably with the number of ring atoms of the bicycloalkyl, tricycloalkyl, heterobicyclic, or heterotricyclic ring being from about 5 to about 12, yet more preferably about 6 to about 10, with about 7 to about 10 ring atoms being even more preferred. In certain preferred embodiments, $R^c$, $R^d$, and $R^e$, taken together with the carbon atom to which they are attached, form a bicycloalkyl, tricycloalkyl, heterobicyclic or heterotricyclic ring, more preferably bicycloalkyl or tricycloalkyl. In embodiments when $R^c$, $R^d$, and $R^e$, taken together with the carbon atom to which they are attached, form a bicycloalkyl or tricycloalkyl ring, substitution of the ring with 1-3 alkyl groups is even more preferred.

In other preferred embodiments of formula I compounds, r is 0, 1, 2, or 3, more preferably 0, 1, or 2, still more preferably 0 or 1, with 0 being even more preferred.

In certain preferred embodiments, the compounds of formula I are selected from the group consisting of:
4-(methylamino)-3-(morpholinosulfonyl)-N-(1,3,3-trimethylbicyclo[2.2.1]heptan-2-yl)benzamide;
3-(N,N-dimethylsulfamoyl)-4-(methylamino)-N-(-1,3,3-trimethyl-bicyclo[2.2.1]heptan-2-yl)benzamide;
N-(bicyclo-[2.2.1]heptan-2-yl)-4-(methylamino)-3-(morpholinosulfonyl)benzamide;
N-(6-methoxy-1,1-dimethyl-1,2,3,4-tetrahydronaphthalen-2-yl)-4-(methylamino)-3-(morpholinosulfonyl)benzamide;
N-(5-methyl-3-phenylisoxazol-4-yl)-4-(methylamino)-3-(morpholinosulfonyl)benzamide;
3-(isoindolin-2-ylsulfonyl)-4-(methylamino)-N-(1,3,3-trimethyl-bicyclo[2.2.1]heptan-2-yl)-benzamide;
N-(bicyclo[2.2.1]heptan-2-yl)-3-(isoindolin-2-ylsulfonyl)-4-(methylamino)benzamide;
N-(7,7-dimethylbicyclo[2.2.1]heptan-2-yl)-3-(isoindolin-2-ylsulfonyl)-4-(methyl-amino)benzamide;
3-(1,3-dihydro-isoindole-2-sulfonyl)-N-[1-(3-hydroxyadamantan-1-yl)-ethyl]-4-methylaminobenzamide;
3-(isoindolin-2-ylsulfonyl)-4-(methylamino)-N-neopentylbenzamide;
3-(isoindolin-2-ylsulfonyl)-4-(methylamino)-N-(1-phenylethyl)benzamide;
3-(isoindolin-2-ylsulfonyl)-4-(methylamino)-N-((1-phenylcyclopentyl)methyl)benzamide;
N-(1-ethylpiperidin-3-yl)-3-(isoindolin-2-ylsulfonyl)-4-(methylamino)benzamide;
3-(isoindolin-2-ylsulfonyl)-4-(methylamino)-N-(1-morpholinobutan-2-yl)benzamide;
3-(N-(2-methoxyethyl)-N-methylsulfamoyl)-4-(methylamino)-N-(1,3,3-trimethylbicyclo-[2.2.1]heptan-2-yl)benzamide;
methyl 2-(N-methyl-2-(methylamino)-5-(1,3,3-trimethylbicyclo[2.2.1]heptan-2-ylcarbamoyl)phenylsulfonamido)acetate;
methyl 2-(5-(-bicyclo[2.2.1]heptan-2-ylcarbamoyl)-N-methyl-2-(methylamino)phenylsulfonamido)acetate;
methyl 2-(5-(7,7-dimethylbicyclo-[2.2.1]heptan-2-ylcarbamoyl)-N-methyl-2-(methylamino)phenylsulfonamido)acetate;
({5-[1-(3-hydroxy-adamantan-1-yl)-ethylcarbamoyl]-2-methylaminobenzenesulfonyl}-methylamino)acetic acid methyl ester;
methyl 2-(N-methyl-2-(methylamino)-5-(neopentylcarbamoyl)phenylsulfonamido) acetate;
methyl 2-(N-methyl-2-(methylamino)-5-(1-phenylethylcarbamoyl)phenylsulfonamido) acetate;
methyl 2-(N-methyl-2-(methylamino)-5-((1-phenylcyclopentyl)methylcarbamoyl)phenylsulfonamido)acetate;
methyl 2-(N-methyl-5-(8-methyl-8-azabicyclo-[3.2.1]octan-3-ylcarbamoyl)-2-(methylamino)phenylsulfonamido)acetate;
3-(azetidin-1-ylsulfonyl)-4-(methylamino)-N-(1,3,3-trimethylbicyclo-[2.2.1]heptan-2-yl)benzamide;
4-(2-(dimethylamino)-ethylamino)-3-(morpholinosulfonyl)-N-(1,3,3-trimethylbicyclo-[2.2.1]heptan-2-yl)benzamide;
4-(2-aminoethylamino)-3-(morpholinosulfonyl)-N-(1,3,3-trimethyl-bicyclo[2.2.1]heptan-2-yl)benzamide;
4-morpholino-3-(morpholinosulfonyl)-N-(1,3,3-trimethyl-bicyclo-[2.2.1]heptan-2-yl)benzamide;
4-(2-methoxyethylamino)-3-(morpholinosulfonyl)-N-(1,3,3-trimethylbicyclo[2.2.1]heptan-2-yl)benzamide;
4-(dimethylamino)-3-(morpholinosulfonyl)-N-(1,3,3-trimethylbicyclo[2.2.1]heptan-2-yl)benzamide;
4-(ethylamino)-3-(morpholinosulfonyl)-N-(1,3,3-trimethyl-bicyclo-[2.2.1]heptan-2-yl)benzamide;
4-(isopropylamino)-3-(morpholinosulfonyl)-N-(1,3,3-trimethylbicyclo[2.2.1]-heptan-2-yl)benzamide; and
4-amino-3-(morpholinosulfonyl)-N-(1,3,3-trimethylbicyclo[2.2.1]heptan-2-yl)benzamide;
or a pharmaceutically acceptable salt thereof.

In other preferred embodiments, the compounds of formula I are selected from the group consisting of:
4-(methylamino)-3-(morpholinosulfonyl)-N-((1S,4R)-1,3,3-trimethylbicyclo[2.2.1]heptan-2-yl)benzamide;
3-(N,N-dimethylsulfamoyl)-4-(methylamino)-N-((1S,4R)-1,3,3-trimethylbicyclo[2.2.1]heptan-2-yl)benzamide;
N-((1R,2R,4S)-bicyclo-[2.2.1]heptan-2-yl)-4-(methylamino)-3-(morpholinosulfonyl)benzamide;
N-(6-methoxy-1,1-dimethyl-1,2,3,4-tetrahydronaphthalen-2-yl)-4-(methylamino)-3-(morpholinosulfonyl)benzamide;
N-(5-methyl-3-phenylisoxazol-4-yl)-4-(methyl-amino)-3-(morpholinosulfonyl)benzamide;
3-(isoindolin-2-ylsulfonyl)-4-(methylamino)-N-((1S,4R)-1,3,3-trimethylbicyclo[2.2.1]heptan-2-yl)-benzamide;

N-((1R,2R,4S)-bicyclo[2.2.1]heptan-2-yl)-3-(isoindolin-2-ylsulfonyl)-4-(methylamino)benzamide;
N-((1R,2S,4R)-7,7-dimethylbicyclo[2.2.1]heptan-2-yl)-3-(isoindolin-2-ylsulfonyl)-4-(methyl-amino)benzamide;
3-(1,3-Dihydro-isoindole-2-sulfonyl)-N-[1-(3-hydroxyadamantan-1-yl)-ethyl]-4-methylaminobenzamide;
3-(isoindolin-2-ylsulfonyl)-4-(methylamino)-N-neopentylbenzamide;
3-(isoindolin-2-ylsulfonyl)-4-(methylamino)-N-(1-phenylethyl)benzamide;
3-(isoindolin-2-ylsulfonyl)-4-(methylamino)-N-((1-phenylcyclopentyl)methyl)benzamide;
N-(1-ethylpiperidin-3-yl)-3-(isoindolin-2-ylsulfonyl)-4-(methylamino)benzamide;
3-(isoindolin-2-ylsulfonyl)-4-(methylamino)-N-(1-morpholinobutan-2-yl)-benzamide;
3-(N-(2-methoxyethyl)-N-methylsulfamoyl)-4-(methylamino)-N-((1S,4R)-1,3,3-trimethylbicyclo-[2.2.1]heptan-2-yl)benzamide;
methyl 2-(N-methyl-2-(methylamino)-5-((1S,4R)-1,3,3-trimethylbicyclo-[2.2.1]heptan-2-ylcarba-moyl)phenylsulfonamido)-acetate;
methyl 2-(5-((1R,2R,4S)-bicyclo[2.2.1]heptan-2-ylcarbamoyl)-N-methyl-2-(methylamino)phenylsulfonamido)acetate;
methyl 2-(5-((1R,2S,4R)-7,7-dimethylbicyclo-[2.2.1]heptan-2-ylcarbamoyl)-N-methyl-2-(methyl-amino)phenylsulfonamido)-acetate;
({5-[1-(3-hydroxy-adaman-tan-1-yl)-ethylcarbamoyl]-2-methylaminobenzenesulfonyl}-methyl-amino)-acetic acid methyl ester;
methyl 2-(N-methyl-2-(methylamino)-5-(neopentylcarbamoyl)phenylsulfonamido) acetate;
methyl 2-(N-methyl-2-(methylamino)-5-(1-phenylethylcarbamoyl)phenylsulfonamido) acetate;
methyl 2-(N-methyl-2-(methylamino)-5-((1-phenylcyclopentyl)methylcarbamoyl)phenylsulfonamido)acetate;
methyl 2-(N-methyl-5-(8-methyl-8-azabicyclo-[3.2.1]octan-3-ylcarbamoyl)-2-(methylamino)-phenylsulfonamido)acetate;
3-(azetidin-1-ylsulfonyl)-4-(methylamino)-N-((1S,4R)-1,3,3-trimethylbicyclo-[2.2.1]heptan-2-yl)benzamide;
4-(2-(dimethylamino)-ethylamino)-3-(morpholinosulfonyl)-N-((1S,4R)-1,3,3-trimethylbicyclo[2.2.1]heptan-2-yl)benzamide;
4-(2-aminoethylamino)-3-(morpholinosulfonyl)-N-((1S,4R)-1,3,3-trimethylbicyclo[2.2.1]heptan-2-yl)benzamide;
4-morpholino-3-(morpholinosulfonyl)-N-((1S,4R)-1,3,3-trimethylbicyclo[2.2.1]heptan-2-yl)benzamide;
4-(2-methoxyethylamino)-3-(morpholinosulfonyl)-N-((1S,4R)-1,3,3-trimethylbicyclo[2.2.1]heptan-2-yl)benzamide;
4-(dimethylamino)-3-(morpholinosulfonyl)-N-((1S,4R)-1,3,3-trimethylbicyclo[2.2.1]heptan-2-yl)-benzamide;
4-(ethylamino)-3-(morpholinosulfonyl)-N-((1S,4R)-1,3,3-trimethylbicyclo[2.2.1]heptan-2-yl)benzamide;
4-(isopropylamino)-3-(morpholinosulfonyl)-N-((1S,4R)-1,3,3-trimethylbicyclo[2.2.1]-heptan-2-yl)benzamide; and
4-amino-3-(morpholinosulfonyl)-N-((1S,4R)-1,3,3-trimethylbicyclo[2.2.1]hep-tan-2-yl)benzamide;
or a pharmaceutically acceptable salt thereof.

In some preferred embodiments, the compounds of formula I are selected from the group consisting of:
4-(methylamino)-3-(morpholinosulfonyl)-N-(-1,3,3-trimethylbicyclo[2.2.1]heptan-2-yl)benzamide;
3-(N,N-dimethylsulfamoyl)-4-(methylamino)-N-(-1,3,3-trimethyl-bicyclo[2.2.1]heptan-2-yl)benzamide;
4-(2-methoxyethylamino)-3-(morpholinosulfonyl)-N-1,3,3-trimethylbicyclo[2.2.1]heptan-2-yl)benzamide;
3-(isoindolin-2-ylsulfonyl)-4-(methylamino)-N-(-1,3,3-trimethyl-bicyclo[2.2.1]heptan-2-yl)-benzamide;
N-(-bicyclo[2.2.1]heptan-2-yl)-3-(isoindolin-2-ylsulfonyl)-4-(methylamino)benzamide;
N-(-7,7-dimethylbicyclo[2.2.1]heptan-2-yl)-3-(isoindolin-2-ylsulfonyl)-4-(methylamino)benzamide;
3-(1,3-dihydro-isoindole-2-sulfonyl)-N-[1-(3-hydroxyadamantan-1-yl)-ethyl]-4-methylaminobenzamide;
3-(N-(2-methoxyethyl)-N-methylsulfamoyl)-4-(methylamino)-N-(-1,3,3-trimethylbicyclo[2.2.1]heptan-2-yl)benzamide;
4-(2-(dimethylamino)-ethylamino)-3-(morpholinosulfonyl)-N-(-1,3,3-trimethylbicyclo-[2.2.1]heptan-2-yl)benzamide; and
4-(dimethylamino)-3-(morpholinosulfonyl)-N-(-1,3,3-trimethyl-bicyclo[2.2.1]heptan-2-yl)-benzamide;
or a pharmaceutically acceptable salt thereof.

In other preferred embodiments, the compounds of formula I are selected from the group consisting of:
4-(methylamino)-3-(morpholinosulfonyl)-N-((1S,4R)-1,3,3-trimethylbicyclo[2.2.1]heptan-2-yl)benzamide;
3-(N,N-dimethylsulfamoyl)-4-(methylamino)-N-((1S,4R)-1,3,3-trimethylbicyclo[2.2.1]heptan-2-yl)benzamide;
4-(2-methoxyethylamino)-3-(morpholinosulfonyl)-N-((1S,4R)-1,3,3-trimethylbicyclo[2.2.1]heptan-2-yl)benzamide;
3-(isoindolin-2-ylsulfonyl)-4-(methylamino)-N-((1S,4R)-1,3,3-trimethylbicyclo[2.2.1]heptan-2-yl)-benzamide;
N-((1R,2R,4S)-bicyclo[2.2.1]heptan-2-yl)-3-(isoindolin-2-ylsulfonyl)-4-(methylamino)benzamide;
N-((1R,2S,4R)-7,7-dimethylbicyclo[2.2.1]heptan-2-yl)-3-(isoindolin-2-ylsulfonyl)-4-(methylamino)benzamide;
3-(1,3-dihydro-isoindole-2-sulfonyl)-N-[1-(3-hydroxyadamantan-1-yl)-ethyl]-4-methylaminobenzamide;
3-(N-(2-methoxyethyl)-N-methylsulfamoyl)-4-(methylamino)-N-((1S,4R)-1,3,3-trimethylbicyclo[2.2.1]heptan-2-yl)benzamide;
4-(2-(dimethylamino)-ethylamino)-3-(morpholinosulfonyl)-N-((1S,4R)-1,3,3-trimethylbicyclo[2.2.1]heptan-2-yl)benzamide; and
4-(dimethylamino)-3-(morpholinosulfonyl)-N-((1S,4R)-1,3,3-trimethylbicyclo[2.2.1]heptan-2-yl)-benzamide;
or a pharmaceutically acceptable salt thereof.

In certain preferred embodiments, the compounds of formula I are selected from the group consisting of:
4-(methylamino)-3-(morpholinosulfonyl)-N-(-1,3,3-trimethylbicyclo[2.2.1]heptan-2-yl)benzamide;
3-(N,N-dimethylsulfamoyl)-4-(methylamino)-N-(-1,3,3-trimethyl-bicyclo[2.2.1]heptan-2-yl)benzamide;
4-(2-methoxyethylamino)-3-(morpholinosulfonyl)-N-(1,3,3-trimethylbicyclo[2.2.1]heptan-2-yl)benzamide;
3-(isoindolin-2-ylsulfonyl)-4-(methylamino)-N-(-1,3,3-trimethyl-bicyclo[2.2.1]heptan-2-yl)-benzamide; and
4-(dimethylamino)-3-(morpholinosulfonyl)-N-(-1,3,3-trimethyl-bicyclo[2.2.1]heptan-2-yl)-benzamide;
or a pharmaceutically acceptable salt thereof.

In other preferred embodiments, the compounds of formula I are selected from the group consisting of:
4-(methylamino)-3-(morpholinosulfonyl)-N-((1S,4R)-1,3,3-trimethylbicyclo[2.2.1]heptan-2-yl)benzamide;
3-(N,N-dimethylsulfamoyl)-4-(methylamino)-N-((1S,4R)-1,3,3-trimethylbicyclo[2.2.1]heptan-2-yl)benzamide;
4-(2-methoxyethylamino)-3-(morpholinosulfonyl)-N-((1S,4R)-1,3,3-trimethylbicyclo[2.2.1]heptan-2-yl)benzamide;
3-(isoindolin-2-ylsulfonyl)-4-(methylamino)-N-((1S,4R)-1,3,3-trimethylbicyclo[2.2.1]heptan-2-yl)-benzamide; and 4-(dimethylamino)-3-(morpholinosulfonyl)-N-((1S,4R)-1,3,3-trimethylbicyclo[2.2.1]heptan-2-yl)-benzamide;

or a pharmaceutically acceptable salt thereof.

In some preferred embodiments, the compounds of formula I are selected from the group consisting of:

3-(N,N-dimethylsulfamoyl)-4-(methylamino)-N-(1,3,3-trimethylbicyclo[2.2.1]heptan-2-yl)benzamide;
N-(bicyclo[2.2.1]heptan-2-yl)-3-(N,N-dimethylsulfamoyl)-4-(methylamino)benzamide;
3-(4-hydroxypiperidin-1-ylsulfonyl)-4-(methylamino)-N-(1,3,3-trimethylbicyclo[2.2.1]heptan-2-yl)benzamide;
3-(3-hydroxypiperidin-1-ylsulfonyl)-4-(methylamino)-N-(1,3,3-trimethylbicyclo[2.2.1]heptan-2-yl)benzamide;
4-(methylamino)-3-(pyrrolidin-1-ylsulfonyl)-N-(1,3,3-trimethylbicyclo[2.2.1]heptan-2-yl)benzamide;
N-(bicyclo[2.2.1]heptan-2-yl)-4-(methylamino)-3-(pyrrolidin-1-ylsulfonyl)-benzamide;
N-(3,3-dimethylbutan-2-yl)-4-(methylamino)-3-(pyrrolidin-1-ylsulfonyl)-benzamide;
4-(methylamino)-3-(pyrrolidin-1-ylsulfonyl)-N-(3,3,5-trimethylcyclohexyl)-benzamide;
3-(3-hydroxypyrrolidin-1-ylsulfonyl)-4-(methylamino)-N-(1,3,3-trimethylbicyclo[2.2.1]hep-tan-2-yl)benzamide;
3-(3-hydroxypyrrolidin-1-ylsulfonyl)-4-(methylamino)-N-(1,3,3-trimethylbicyclo[2.2.1]heptan-2-yl)benzamide;
N-adamantan-1-yl-4-methylamino-3-(morpholine-4-sulfonyl)-benzamide;
3-(N-tert-butylsulfamoyl)-4-(methylamino)-N-(1,3,3-trimethylbicyclo[2.2.1]heptan-2-yl)benzamide;
3-(N-ethyl-N-methyl-sulfamoyl)-4-(methylamino)-N-(1,3,3-trimethylbicyclo[2.2.1]heptan-2-yl)benzamide;
methyl 3-(2-(morpholinosulfonyl)-4-(1,3,3-trimethylbicyclo[2.2.1]-heptan-2-ylcarbamoyl)-phenyl)amino)propanoate;
4-(2-methoxyethylamino)-3-(pyrrolidin-1-ylsulfonyl)-N-(1,3,3-trimethylbicyclo[2.2.1]heptan-2-yl)benzamide;
4-(benzylamino)-3-(pyrro-lidin-1-ylsulfonyl)-N-(1,3,3-trimethylbicyclo[2.2.1]heptan-2-yl)benzamide;
3-(N,N-dimethylsulfamoyl)-4-(2-methoxyethylamino)-N-(1,3,3-trimethylbicyclo[2.2.1]heptan-2-yl)benzamide;
3-(N-(2-hydroxyethyl)-N-methylsulfamoyl)-4-(2-methoxyethylamino)-N-(1,3,3-trimethylbicyclo[2.2.1]heptan-2-yl)benzamide;
4-amino-3-(N-tert-butyl-sulfamoyl)-N-(1,3,3-trimethylbicyclo[2.2.1]heptan-2-yl)benzamide; and
3-(N-benzyl-N-methyl-sulfamoyl)-4-(2-(dimethyl-amino)ethylamino)-N-(1,3,3-trimethylbicyclo[2.2.1]heptan-2-yl)-benzamide;

or a pharmaceutically acceptable salt thereof.

In other preferred embodiments, the compounds of formula I are selected from the group consisting of:

3-(N,N-dimethylsulfamoyl)-4-(methylamino)-N-((1S,4R)-1,3,3-trimethylbicyclo[2.2.1]heptan-2-yl)benzamide;
N-((1R,2R,4S)-bicyclo[2.2.1]heptan-2-yl)-3-(N,N-dimethylsulfamoyl)-4-(methylamino)benzamide;
3-(4-hydroxypiperidin-1-ylsulfonyl)-4-(methylamino)-N-((1S,4R)-1,3,3-trimethylbicyclo[2.2.1]heptan-2-yl)benzamide;
3-(3-hydroxypiperidin-1-ylsulfonyl)-4-(methylamino)-N-((1S,4R)-1,3,3-trimethylbicyclo[2.2.1]heptan-2-yl)benzamide;
4-(methylamino)-3-(pyrrolidin-1-ylsulfonyl)-N-((1S,4R)-1,3,3-trimethylbicyclo[2.2.1]heptan-2-yl)benzamide;
N-((1R,2R,4S)-bicyclo[2.2.1]heptan-2-yl)-4-(methylamino)-3-(pyrrolidin-1-ylsulfonyl)benzamide;
N-(3,3-dimethylbutan-2-yl)-4-(methylamino)-3-(pyrrolidin-1-ylsulfonyl)-benzamide;
4-(methylamino)-3-(pyrrolidin-1-ylsulfonyl)-N-(3,3,5-trimethylcyclohexyl)-benzamide;
3-((R)-3-hydroxypyrrolidin-1-ylsulfonyl)-4-(methylamino)-N-((1S,4R)-1,3,3-trimethylbicyclo[2.2.1]hep-tan-2-yl)benzamide;
3-((S)-3-hydroxypyrrolidin-1-ylsulfonyl)-4-(methylamino)-N-((1S,4R)-1,3,3-trimethylbicyclo[2.2.1]heptan-2-yl)benzamide;
N-adamantan-1-yl-4-methylamino-3-(morpholine-4-sulfonyl)-benzamide;
3-(N-tert-butylsulfamoyl)-4-(methylamino)-N-((1S,4R)-1,3,3-trimethylbicyclo[2.2.1]heptan-2-yl)benzamide;
3-(N-ethyl-N-methyl-sulfamoyl)-4-(methylamino)-N-((1S,4R)-1,3,3-trimethylbicyclo[2.2.1]heptan-2-yl)benzamide;
methyl 3-(2-(morpholinosulfonyl)-4-((1S,4R)-1,3,3-trimethylbicyclo[2.2.1]-heptan-2-ylcarbamoyl)-phenyl)amino)propanoate;
4-(2-methoxyethylamino)-3-(pyrrolidin-1-ylsulfonyl)-N-((1S,4R)-1,3,3-trimethylbicyclo[2.2.1]heptan-2-yl)benzamide;
4-(benzylamino)-3-(pyrro-lidin-1-ylsulfonyl)-N-((1S,4R)-1,3,3-trimethylbicyclo[2.2.1]heptan-2-yl)benzamide;
3-(N,N-dimethylsulfamoyl)-4-(2-methoxyethylamino)-N-((1S,4R)-1,3,3-trimethylbicyclo[2.2.1]heptan-2-yl)benzamide;
3-(N-(2-hydroxyethyl)-N-methylsulfamoyl)-4-(2-methoxyethylamino)-N-((1S,4R)-1,3,3-trimethylbicyclo[2.2.1]heptan-2-yl)benzamide;
4-amino-3-(N-tert-butyl-sulfamoyl)-N-((1S,4R)-1,3,3-trimethylbicyclo[2.2.1]heptan-2-yl)benzamide; and
3-(N-benzyl-N-methyl-sulfamoyl)-4-(2-(dimethyl-amino)ethylamino)-N-((1S,4R)-1,3,3-trimethylbicyclo[2.2.1]heptan-2-yl)-benzamide;

or a pharmaceutically acceptable salt thereof.

In certain preferred embodiments, the compounds of formula I are selected from the group consisting of:

3-(N,N-dimethylsulfamoyl)-4-(methylamino)-N-(1,3,3-trimethylbicyclo[2.2.1]heptan-2-yl)benzamide;
N-adamantan-1-yl-4-methylamino-3-(morpholine-4-sulfonyl)-benzamide;
({5-[1-(3-Hydroxyadamantan-1-yl)-ethyl-carbamoyl]-2-methylaminobenzenesulfonyl}-methylamino)-acetic acid methyl ester;
3-(3-hydroxypiperidin-1-ylsulfonyl)-4-(methylamino)-N-(1,3,3-trimethylbicyclo[2.2.1]heptan-2-yl)benzamide;
3-(3-hydroxypyrrolidin-1-ylsulfonyl)-4-(methylamino)-N-(1,3,3-trimethylbicyclo[2.2.1]heptan-2-yl)benzamide;
4-(benzylamino)-3-(pyrrolidin-1-ylsulfonyl)-N-(1,3,3-trimethylbicyclo[2.2.1]heptan-2-yl)benzamide;
3-(N,N-dimethylsulfamoyl)-4-(2-methoxyethylamino)-N-(1,3,3-trimethylbicyclo[2.2.1]heptan-2-yl)benzamide;
N-(3,3-dimethylbutan-2-yl)-4-(methylamino)-3-(pyrrolidin-1-ylsulfonyl)-benzamide;
3-(N-ethyl-N-methylsulfamoyl)-4-(methylamino)-N-(1,3,3-trimethylbicyclo[2.2.1]heptan-2-yl)benzamide; and
4-(2-methoxyethylamino)-3-(pyrrolidin-1-ylsulfonyl)-N-(1,3,3-trimethylbicyclo[2.2.1]heptan-2-yl)benzamide;

or a pharmaceutically acceptable salt thereof.

In some preferred embodiments, the compounds of formula I are selected from the group consisting of:

3-(N,N-dimethylsulfamoyl)-4-(methylamino)-N-((1S,4R)-1,3,3-trimethylbicyclo[2.2.1]heptan-2-yl)benzamide;
N-adamantan-1-yl-4-methylamino-3-(morpholine-4-sulfonyl)-benzamide;
({5-[1-(3-Hydroxyadamantan-1-yl)-ethyl-carbamoyl]-2-methylaminobenzenesulfonyl}-methylamino)-acetic acid methyl ester;

3-(3-hydroxypiperidin-1-ylsulfonyl)-4-(methylamino)-N-((1S,4R)-1,3,3-trimethylbicyclo[2.2.1]heptan-2-yl)benzamide;

3-((S)-3-hydroxypyrrolidin-1-ylsulfonyl)-4-(methylamino)-N-((1S,4R)-1,3,3-trimethylbicyclo[2.2.1]heptan-2-yl)benzamide;

4-(benzylamino)-3-(pyrrolidin-1-ylsulfonyl)-N-((1S,4R)-1,3,3-trimethylbicyclo[2.2.1]heptan-2-yl)benzamide;

3-(N,N-dimethylsulfamoyl)-4-(2-methoxyethylamino)-N-((1S,4R)-1,3,3-trimethylbicyclo[2.2.1]heptan-2-yl)benzamide;

N-(3,3-dimethylbutan-2-yl)-4-(methylamino)-3-(pyrrolidin-1-ylsulfonyl)-benzamide;

3-(N-ethyl-N-methylsulfamoyl)-4-(methylamino)-N-((1S,4R)-1,3,3-trimethylbicyclo[2.2.1]heptan-2-yl)benzamide; and 4-(2-methoxyethylamino)-3-(pyrrolidin-1-ylsulfonyl)-N-((1S,4R)-1,3,3-trimethylbicyclo[2.2.1]heptan-2-yl)benzamide;

or a pharmaceutically acceptable salt thereof.

In other preferred embodiments, the compounds of formula I are selected from the group consisting of:

3-(N,N-dimethylsulfamoyl)-4-(methylamino)-N-(1,3,3-trimethylbicyclo[2.2.1]heptan-2-yl)benzamide;

N-adamantan-1-yl-4-methylamino-3-(morpholine-4-sulfonyl)-benzamide;

({5-[1-(3-Hydroxyadamantan-1-yl)-ethyl-carbamoyl]-2-methylaminobenzenesulfonyl}-methylamino)-acetic acid methyl ester;

3-(3-hydroxypiperidin-1-ylsulfonyl)-4-(methylamino)-N-(1,3,3-trimethylbicyclo[2.2.1]heptan-2-yl)benzamide; and 3-(3-hydroxypyrrolidin-1-ylsulfonyl)-4-(methylamino)-N-(1,3,3-trimethylbicyclo[2.2.1]heptan-2-yl)benzamide;

or a pharmaceutically acceptable salt thereof.

In certain preferred embodiments, the compounds of formula I are selected from the group consisting of:

3-(N,N-dimethylsulfamoyl)-4-(methylamino)-N-((1S,4R)-1,3,3-trimethylbicyclo[2.2.1]heptan-2-yl)benzamide;

N-adamantan-1-yl-4-methylamino-3-(morpholine-4-sulfonyl)-benzamide;

({5-[1-(3-Hydroxyadamantan-1-yl)-ethyl-carbamoyl]-2-methylaminobenzenesulfonyl}-methylamino)-acetic acid methyl ester;

3-(3-hydroxypiperidin-1-ylsulfonyl)-4-(methylamino)-N-((1S,4R)-1,3,3-trimethylbicyclo[2.2.1]heptan-2-yl)benzamide; and 3-((S)-3-hydroxypyrrolidin-1-ylsulfonyl)-4-(methylamino)-N-((1S,4R)-1,3,3-trimethylbicyclo[2.2.1]heptan-2-yl)benzamide;

or a pharmaceutically acceptable salt thereof.

In some preferred embodiments, the compounds of formula I are selected from the group consisting of:

3-(N,N-dimethylsulfamoyl)-4-(methylamino)-N-(1,3,3-trimethylbicyclo[2.2.1]heptan-2-yl)benzamide; and N-adamantan-1-yl-4-methylamino-3-(morpholine-4-sulfonyl)-benzamide;

or a pharmaceutically acceptable salt thereof.

In other preferred embodiments, the compounds of formula I are selected from the group consisting of:

3-(N,N-dimethylsulfamoyl)-4-(methylamino)-N-((1S,4R)-1,3,3-trimethylbicyclo[2.2.1]heptan-2-yl)benzamide; and N-adamantan-1-yl-4-methylamino-3-(morpholine-4-sulfonyl)-benzamide;

or a pharmaceutically acceptable salt thereof.

In another embodiment, the present invention provides compounds of formula II:

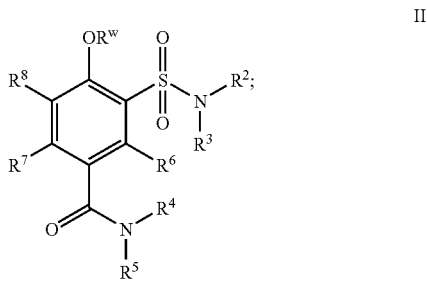

wherein:

$R^w$ is H, alkyl, cycloalkyl, cycloalkylalkyl, aryl, aralkyl, heterocycloalkyl, heterocycloalkylalkyl, heteroaryl, or heteroaralkyl;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^4$ is H or alkyl;

$R^5$ is:

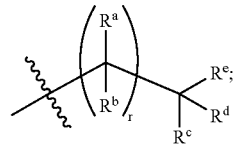

each $R^a$, $R^b$, $R^c$, $R^d$, and $R^e$ is independently H or alkyl, provided that at least two of $R^c$, $R^d$, and $R^e$ are other than H; or $R^d$ and $R^e$, taken together with the carbon atom to which they are attached, form a carbocyclic ring; or $R^c$, $R^d$, and $R^e$, taken together with the carbon atom to which they are attached, form a bicycloalkyl or tricycloalkyl ring;

$R^6$, $R^7$, and $R^8$ are each independently H, F, Cl, Br, or alkyl;

each $R^9$ is independently H, alkyl, aryl, —C(=O)—$R^{11}$, —C(=O)—O$R^{11}$, —[C($R^{11}$)($R^{11}$)]$_s$—C(=O)—O$R^{11}$, —SO$_2R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

or a pharmaceutically acceptable salt thereof.

In certain preferred embodiments, the compounds of the invention have the formula II described hereinabove with the provisos that:

(1) when $R^w$ is methyl, $R^4$, $R^6$, $R^7$, and $R^8$ are each H, r is 0, $R^2$ is methyl, and $R^3$ is benzyl, or $R^2$ and $R^3$, taken together with the nitrogen atom to which they are attached, form a pyrrolidinyl or morpholinyl ring, then $R^c$, $R^d$, and $R^e$ are each independently alkyl in which at least one of $R^c$, $R^d$, and $R^e$ is other than methyl or ethyl;

(2) when $R^w$ is methyl or ethyl, $R^4$, $R^6$, $R^7$, and $R^8$ are each H, r is 0, $R^2$ and $R^3$ are each independently methyl, ethyl, or benzyl, or $R^2$ and $R^3$, taken together with the nitrogen atom to which they are attached, form a 2-methylpiperidinyl, 2-ethylpiperidinyl, 4-methylpiperidinyl, morpholinyl, pyrrolidinyl, azepanyl, 4-phenylpyrrolidinonyl, 1,2,3,4-tetrahydroquinolinyl, or 4-(pyridin-2-yl) piperazinyl ring, and $R^d$ and $R^e$, taken together with the carbon atom to which they are attached, form a carbocyclic ring, wherein when said carbocyclic ring is other than bicycloalkyl or tricycloalkyl, then $R^c$ is alkyl;

(3) when $R^w$ is methyl, $R^4$, $R^6$, $R^7$, $R^8$, and $R^a$ are each H, r is 1, 2, or 3, and $R^2$ and $R^3$ are each independently methyl, ethyl, or benzyl, then $R^c$, $R^d$, and $R^e$ are each independently alkyl;

(4) when $R^w$ is methyl, $R^4$, $R^6$, $R^7$, $R^8$, and $R^a$ are each H, r is 1, 2, or 3, $R^2$ and $R^3$, taken together with the nitrogen atom to which they are attached, form a morpholinyl or pyrrolidinyl ring, and $R^d$ and $R^e$, taken together with the carbon atom to which they are attached, form a carbocyclic ring, wherein when said carbocyclic ring is other than bicycloalkyl or tricycloalkyl, then $R^c$ is alkyl;

(5) when $R^w$ is methyl, $R^4$, $R^6$, $R^7$, $R^8$, and $R^a$ are each H, r is 1, and $R^c$, $R^d$, and $R^e$, taken together with the carbon atom to which they are attached form an adamantan-1-yl, then $R^2$ and $R^3$, when taken together with the nitrogen atom to which they are attached, form other than pyrrolidinyl, morpholinyl, or 4-(3-chlorophenyl)-piperazin-1-yl;

(6) when $R^w$ is methyl or ethyl, $R^2$, $R^4$, $R^6$, $R^7$, and $R^8$ are each H, and $R^3$ is methyl, then $R^5$ is other than sec-butyl, tert-pentyl, or 1,3-dimethylbutyl;

(7) when $R^w$ is $CH_3$, $R^2$, $R^4$, $R^6$, $R^7$, and $R^8$ are each H, r is 0, and $R^5$ is indan-1-yl, then $R^3$ is other than unsubstituted alkyl or unsubstituted cycloalkyl; and (8) that the compound of formula II is other than 3-(5-chloro-2,4-dimethoxy-phenylsulfamoyl)-N-cycloheptyl-4-methoxy-benzamide, 3-(4-bromo-phenylsulfamoyl)-N-cycloheptyl-4-methoxy-benzamide, or N-cyclohexyl-4-methoxy-N-methyl-3-(morpholine-4-sulfonyl)-benzamide.

In certain preferred embodiments of formula II compounds, $R^w$ is alkyl, cycloalkyl, cycloalkylalkyl, aryl, aralkyl, heterocycloalkyl, heterocycloalkylalkyl, heteroaryl, or heteroaralkyl, more preferably H, alkyl, or aralkyl, still more preferably H or alkyl. When $R^w$ is alkyl, it is preferably $C_1$-$C_6$alkyl, with $C_1$-$C_3$alkyl being more preferred. When $R^w$ is aralkyl, it is preferably $C_6$aryl$C_1$-$C_3$alkyl, with benzyl being more preferred. In some preferred embodiments the alkyl is preferably $C_2$-$C_3$alkyl, more preferably ethyl, n-propyl, or isopropyl, each optionally substituted with amino, alkylamino, dialkylamino, or alkoxy, wherein the alkyl moieties of said alkylamino, dialkylamino, or alkoxy, preferably dialkylamino or alkoxy, are each independently $C_1$-$C_6$alkyl, still more preferably $C_1$-$C_3$alkyl, yet more preferably methyl or ethyl.

In certain preferred embodiments of formula II compounds, $R^2$ and $R^3$ are each independently alkyl, cycloalkyl, cycloalkylalkyl, aryl, aralkyl, heterocycloalkyl, heterocycloalkylalkyl, heteroaryl, or heteroaralkyl. In other preferred embodiments, $R^2$ and $R^3$ are each independently H or alkyl, even more preferably alkyl. In certain embodiments where $R^2$ or $R^3$ is alkyl, it is more preferably $C_1$-$C_6$alkyl, still more preferably $C_1$-$C_3$alkyl, yet more preferably optionally substituted methyl. In some preferred embodiments, the alkyl is optionally substituted with —C(=O)O-alkyl, wherein the alkyl moiety of said —C(=O)O-alkyl, is $C_1$-$C_6$alkyl, still more preferably $C_1$-$C_3$alkyl, yet more preferably methyl. In other preferred embodiments, $R^2$ or $R^3$ are each independently alkyl or aralkyl. When $R^2$ or $R^3$ is aralkyl it is preferably $C_6$aryl$C_1$alkyl, with benzyl being more preferred.

In certain preferred embodiments of formula II compounds, $R^2$ and $R^3$, when taken together with the nitrogen atom to which they are attached, form a 3- to 8-, more preferably a 4- to 6-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—. In certain embodiments, 1 of the heterocycloalkyl ring carbon atoms independently is replaced by —O—. In other preferred embodiments, the heterocycloalkyl ring is fused to a $C_6$aryl, more preferably phenyl, ring. In some preferred embodiments, $R^2$ and $R^3$ taken together with the nitrogen atom to which they are attached, form a piperidine, pyrrolidine, or morpholine ring, more preferably a piperidine or pyrrolidine ring, each optionally substituted, preferably with hydroxy. In certain other preferred embodiments, $R^2$ and $R^3$ taken together with the nitrogen atom to which they are attached, form a morpholine ring.

In other preferred embodiments of formula II compounds wherein $R^4$ is alkyl, it is preferably $C_1$-$C_6$alkyl, with $C_1$-$C_3$alkyl being more preferred. In certain preferred embodiments, $R^4$ is H.

In other preferred embodiments of formula II compounds, at least one of $R^a$ and $R^b$ is H, more preferably $R^a$ is H, yet more preferably $R^a$ and $R^b$ are each H. In embodiments where each $R^a$ or $R^b$ is alkyl; it is more preferably $C_1$-$C_6$alkyl, still more preferably $C_1$-$C_3$alkyl, yet more preferably optionally substituted methyl.

In some preferred embodiments of formula II compounds, $R^c$ is H or alkyl, more preferably alkyl. When $R^c$ is alkyl, it is more preferably $C_1$-$C_6$alkyl, still more preferably $C_1$-$C_3$alkyl, with optionally substituted methyl or ethyl being even more preferred.

In some preferred embodiments of formula II compounds, $R^d$ and $R^e$ are each H or $C_1$-$C_6$alkyl, still more preferably H or $C_1$-$C_3$alkyl. In other preferred embodiments, $R^d$ and $R^e$ are each alkyl, more preferably $C_1$-$C_6$alkyl, still more preferably $C_1$-$C_3$alkyl.

In other preferred embodiments of formula II compounds, $R^d$ and $R^e$, taken together with the carbon atom to which they are attached, form a carbocyclic ring, more preferably with the number of ring atoms of the carbocyclic ring being from about 3 to about 12, yet more preferably about 3 to about 10, with about 5 to about 10 ring atoms being even more preferred. In certain of these embodiments, $R^c$ is alkyl, more preferably, $C_1$-$C_6$alkyl, still more preferably $C_1$-$C_3$alkyl. In certain preferred embodiments, $R^d$ and $R^e$, taken together with the carbon atom to which they are attached, form a monocycloalkyl or bicycloalkyl ring. In other embodiments, $R^d$ and $R^e$, taken together with the carbon atom to which they are attached, form a bicycloalkyl or tricycloalkyl ring, more preferably wherein the bicycloalkyl or tricycloalkyl ring is substituted with 1-3 alkyl groups.

In certain preferred embodiments of formula II compounds, $R^c$, $R^d$, and $R^e$, taken together with the carbon atom to which they are attached, form a bicycloalkyl or tricycloalkyl ring, more preferably with the number of ring atoms of the bicycloalkyl or tricycloalkyl ring being from about 5 to about 12, yet more preferably about 6 to about 10, with about 7 to about 10 ring atoms being even more preferred. In certain preferred embodiments, when $R^c$, $R^d$, and $R^e$, taken together with the carbon atom to which they are attached form a bicycloalkyl or tricycloalkyl ring, wherein the bicycloalkyl or tricycloalkyl ring is substituted with 1-3 alkyl groups.

In certain more preferred embodiments of formula II compounds, $R^5$ is:

[structures]

or an enantiomeric or diastereomeric form thereof;
wherein:
===== represents a single or double bond between the two bonded carbon atom termini.

In other preferred embodiments of formula II compounds, $R^5$ is:

[structure]

or an enantiomeric or diastereomeric form thereof;
wherein:
A, B, and C are each independently $C(R^{12})(R^{12})$, a bond, or —O—, provided that no more than one of A, B, and C is a bond and provided that no more than one of A, B, and C is —O—;

D and E are each independently $C(R^{12})(R^{12})$ or —O—, provided that at least three of A, B, C, D, and E are other than —O—; and
each $R^{12}$ is independently H or $C_1$-$C_3$ alkyl.

In certain preferred embodiments of formula II compounds, $R^6$, $R^7$, and $R^8$ are each H.

In some preferred embodiments of formula II compounds, r is 0, 1, or 2, more preferably 0 or 1, with 0 being even more preferred.

In some preferred embodiments the formula II compounds are selected from the group consisting of:
4-(benzyloxy)-3-(morpholinosulfonyl)-N-(-1,3,3-trimethylbicyclo[2.2.1]heptan-2-yl)benzamide;
4-hydroxy-3-(morpholinosulfonyl)-N-(-1,3,3-trimethylbicyclo[2.2.1]-heptan-2-yl)benzamide; and
4-methoxy-3-(morpholinosulfonyl)-N-(-1,3,3-trimethylbicyclo[2.2.1]heptan-2-yl)benzamide;
or a pharmaceutically acceptable salt thereof.

In certain preferred embodiments the formula II compounds are selected from the group consisting of:
4-(benzyloxy)-3-(morpholinosulfonyl)-N-((1S,4R)-1,3,3-trimethylbicyclo[2.2.1]heptan-2-yl)benzamide;
4-hydroxy-3-(morpholinosulfonyl)-N-((1S,4R)-1,3,3-trimethylbicyclo[2.2.1]-heptan-2-yl)benzamide; and
4-methoxy-3-(morpholinosulfonyl)-N-((1S,4R)-1,3,3-trimethylbicyclo[2.2.1]heptan-2-yl)benzamide;
or a pharmaceutically acceptable salt thereof.

In some preferred embodiments the formula II compounds are selected from the group consisting of:
4-(benzyloxy)-3-(morpholinosulfonyl)-N-(1,3,3-trimethylbicyclo[2.2.1]heptan-2-yl)benzamide;
4-hydroxy-3-(morpholino-sulfonyl)-N-(1,3,3-trimethylbicyclo[2.2.1]-heptan-2-yl)benzamide;
4-methoxy-3-(morpholinosulfonyl)-N-(1,3,3-trimethybicyclo[2.2.1]heptan-2-yl)benzamide; and
4-(2-methoxyethoxy)-3-(morpholinosulfonyl)-N-(1,3,3-trimethylbicyclo[2.2.1]heptan-2-yl)benzamide;
or a pharmaceutically acceptable salt thereof.

In certain preferred embodiments the formula II compounds are selected from the group consisting of:
4-(benzyloxy)-3-(morpholinosulfonyl)-N-((1S,4R)-1,3,3-trimethylbicyclo[2.2.1]heptan-2-yl)benzamide;
4-hydroxy-3-(morpholino-sulfonyl)-N-((1S,4R)-1,3,3-trimethylbicyclo[2.2.1]-heptan-2-yl)benzamide;
4-methoxy-3-(morpholinosulfonyl)-N-((1S,4R)-1,3,3-trimethybicyclo[2.2.1]heptan-2-yl)benzamide; and
4-(2-methoxyethoxy)-3-(morpholinosulfonyl)-N-((1S,4R)-1,3,3-trimethylbicyclo[2.2.1]heptan-2-yl)benzamide;
or a pharmaceutically acceptable salt thereof.

The compounds employed in the methods of the present invention may exist in prodrug form. As used herein, "prodrug" is intended to include any covalently bonded carriers which release the active parent drug, for example, as according to Formula I or II, or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example Formula I or II, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxy groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl groups. Preferred hydroxyl protecting groups include the benzyl and the tertiary-butyldimethylsilyl groups. Other preferred protecting groups that may be employed in accordance with the present invention may be described in Greene, T. W. and Wuts, P. G. M., *Protective Groups in Organic Synthesis* 3d. Ed., Wiley & Sons, 1991.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosure of which is hereby incorporated herein by reference, in its entirety.

Although the compounds of the present invention may be administered as the pure chemicals, it is preferable to present the active ingredient as a pharmaceutical composition. The invention thus further provides pharmaceutical compositions comprising one or more of the cannabinoid receptor modulator compounds of the present invention, for example compounds of Formula I or II, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

In accordance with certain embodiments of the present invention, the compositions and methods of the invention may further comprise at least one cannabinoid. A variety of cannabinoids are available that may be suitable for use in the present methods and compositions. Generally speaking, it is only necessary that the cannabinoid provide the desired effect (for example, pain alleviation), and be capable of being incorporated into the present combination products and methods (discussed in detail below). In preferred embodiments, the present methods and compositions may involve a cannabinoid that is selected from $\Delta^9$-tetrahydrocannabinol and cannabidiol, and mixtures thereof, more preferably, $\Delta^9$-tetrahydrocannabinol.

Alternatively, in accordance with certain embodiments of the present invention, the compositions and methods of the invention may further comprise at least one opioid. A wide variety of opioids are available that may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid that is selected from alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and/or tramadol. More preferably, the opioid is selected from morphine, codeine, oxycodone, hydrocodone, dihydrocodeine, propoxyphene, fentanyl, tramadol, and mixtures thereof.

The opioid component of the present methods and compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference*, 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J., et al., *Pain*, 1996, 67, 361), L-364,718 and other CCK antagonists (Dourish, C. T., et al., *Eur. J. Pharmacol.*, 1988, 147, 469), NOS inhibitors (Bhargava, H. N., et al., *Neuropeptides*, 1996, 30, 219), PKC inhibitors (Bilsky, E. J., et al., *J. Pharmacol. Exp. Ther.*, 1996, 277, 484), and dynorphin antagonists or antisera (Nichols, M. L., et al., *Pain*, 1997, 69, 317). The disclosures of each of the foregoing documents are hereby incorporated herein by reference, in their entireties.

Alternatively, in accordance with certain other embodiments of the present invention, the compositions of the invention may further comprise at least one analgesic, such as for example, COX2 inhibitors, aspirin, acetaminophen, ibuprophen, naproxen, and the like, and mixtures thereof. Generally speaking, it is only necessary that the analgesic provide the desired effect (for example, pain alleviation), and be capable of being incorporated into the present combination products and methods (discussed in detail below).

In accordance with still other embodiments of the present invention, the compositions of the invention may further comprise at least one therapeutic agent selected from the group consisting of anti-seizure agents, such as for example, carbamazepine, gabapentin, lamotrigine, and phenyloin, anti-depressants such as, for example, amitryptiline, NMDA receptor antagonists, ion channel antagonists, nicotinic receptor agonists, and anti-Parkinson's agents, such as for example, Deprenyl, Amantadine, Levodopa, and Carbidopa. Generally speaking, it is only necessary that the anti seizure agent, anti-depressant, NMDA receptor antagonist, ion channel antagonist, nicotinic receptor agonist, or antiParkinson's agent provide the desired effect (for example, inhibition of seizures, alleviation of depression, and the like), and be capable of being incorporated into the present combination products and methods (discussed in detail below).

The compounds of the invention may be administered in an effective amount by any of the conventional techniques well-established in the medical field. The compounds employed in the methods of the present invention including, for example, the compounds of Formula I or II, may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages. Although the proper dosage of the products of this invention will be readily ascertainable by one skilled in the art, once armed with the present disclosure, by way of general guidance, for example, typically a daily dosage of the compound of the invention, preferably a compound as described herein, may range from about 0.001 to about 100 milligrams of the compound of the invention, preferably a compound as described herein, (and all combinations and subcombinations of ranges and specific dosage amounts therein), per kilogram of patient body weight. Preferably, the daily dosage may be about 0.01 to about 10 milligrams of the compound of the invention, preferably a compound as described herein per kilogram of patient body weight. Even more preferably, the daily dosage may be about 0.1 milligrams of the compound of the invention, preferably a compound as described herein per kilogram of patient body weight. With regard to a typical dosage form of this type, such as a tablet, the compounds of the invention, preferably a compound as described herein, generally may be present in an amount of about 0.1 to about 4 milligrams.

The combination products of this invention, such as pharmaceutical compositions comprising cannabinoids and/or opioids in combination with the compounds of Formula I or II, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the cannabinoid and/or opioid compounds and the compounds of Formula I or II may be administered at the same time (that is, together), or in any order. When not administered at the same time, preferably the administration of a cannabinoid and/or opioid and the compounds of Formula I or II occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the cannabinoids and/or opioids and the compounds of Formula I or II are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where a cannabinoid and/or opioid compound is combined with the compounds of Formula I or II, for example, typically a daily dosage may range from about 0.01 to about 100 milligrams of the cannabinoid and/or opioid (and all combinations and subcombinations of ranges therein) and about 0.001 to about 100 milligrams of the compounds of Formula I or II (and all combinations and subcombinations of ranges therein), per kilogram of patient body weight. Preferably, the a daily dosage may be about 0.1 to about 10 milligrams of the cannabinoid and/or opioid and about 0.01 to about 10 milligrams of the compounds of Formula I or II per kilogram of patient body weight. Even more preferably, the daily dosage may be about 1.0 milligrams of the cannabinoid and/or opioid and about 0.1 milligrams of the compounds of Formula I or II per kilogram of patient body weight. With regard to a typical dosage form of this type of combination product, such as a tablet, the cannabinoid compounds (e.g. $\Delta^9$-tetrahydrocannabinol or cannabidiol) and/or the opioid compounds (e.g., morphine) and generally may be present in an amount of about 15 to about 200 milligrams, and the compounds of Formula I or II in an amount of about 0.1 to about 4 milligrams.

Particularly when provided as a single dosage form, the potential exists for a chemical interaction between the combined active ingredients (for example, a cannabinoid and the compounds of Formula I or II). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

Pharmaceutical kits useful in, for example, the treatment of pain, which comprise a therapeutically effective amount of a cannabinoid and/or opioid along with a therapeutically effective amount of a sulfamoyl benzamide compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid or cannabinoid compound and the compound of Formula I or II may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

In certain preferred embodiments, the compounds, pharmaceutical compositions and methods of the present invention may involve a peripheral cannabinoid receptor agonist compound. The term "peripheral" designates that the compound acts primarily on physiological systems and components external to the central nervous system. In preferred form, the peripheral receptor agonist compounds employed in the methods of the present invention exhibit high levels of activity with respect to peripheral tissue, such as, gastrointestinal tissue, while exhibiting reduced, and preferably substantially no CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5%, and most preferably 0%, of the pharmacological activity of the compounds employed in the present methods is exhibited in the CNS.

Furthermore, it is preferred in certain embodiments of the invention where the compound is administered to agonize the peripheral cannabinoid receptors that the compound of the invention administered does not substantially cross the blood-brain barrier and thereby reduces the classical central side effects as observed for blood-brain penetrating cannabinoid agonists such as $\Delta^9$-tetrahydrocannabinol ($\Delta^9$-THC). The central side effects of blood brain penetrating cannabinoid agonists limits their clinical utility, such as their use in the relief of pain. The phrase "does not substantially cross," as used herein, means that less than about 30% by weight of the compound employed in the present methods crosses the blood-brain barrier, preferably less than about 15% by weight, more preferably less than about 10% by weight, even more preferable less than about 5% by weight and most preferably 0% by weight of the compound crosses the blood-brain barrier. Selected compounds can be evaluated for CNS penetration by determining plasma and brain levels following i.v. administration.

The compounds of the present invention may be used in methods to bind cannabinoid receptors, more preferably CB1 or CB2 cannabinoid receptors. Such binding may be accomplished by contacting the receptor with an effective amount of a compound of formula I or II. The cannabinoid receptors may be located in the central nervous system or located peripherally to the central nervous system or in both locations. Preferably, the contacting step conducted in an aqueous medium, preferably at physiologically relevant ionic strength, pH, and the like.

In yet another aspect, the invention is directed to methods of binding cannabinoid receptors, preferably CB1 and/or CB2 receptors, comprising the step of administering to a patient in need thereof, an effective amount of a compound of the invention including, for example, a compound of formula I or II, or any combination thereof.

In certain preferred aspects, the methods are directed to the treatment of a disease or disorder selected from the group consisting of a gastrointestinal disorder, inflammation, an autoimmune disease, an immune related disorder, pain, hypertension, a neurodegenerative disease, and a neurological disorder, or any combination thereof and comprise the step of administering to said patient an effective amount of a compound of formula I or II, or any combination thereof.

In other preferred aspects, the methods are directed to providing cardioprotection against ischemic or reperfusion effects, inhibiting mechanical hyperalgesia associated with nerve injury, inducing apoptosis in malignant cells, modulating appetite, or a combination thereof, and comprise the step of administering to said patient an effective amount of a compound of formula I or II, or any combination thereof.

In some preferred embodiments, the cannabinoid receptors are CB1 and/or CB2 cannabinoid receptors. In certain more preferred embodiments, the compound selectively binds the CB2 cannabinoid receptors relative to the CB1 receptors, even more preferably peripheral CB2 receptors. In certain preferred embodiments, the cannabinoid receptors are located in the central nervous system. In other preferred embodiments, the cannabinoid receptors are located peripherally to the central nervous system. In some other preferred embodiments, the compound exhibits activity toward the cannabinoid receptors. In certain preferred embodiments, the binding agonizes the activity of the cannabinoid receptors. In other preferred embodiments, the binding antagonizes the activity of the cannabinoid receptors.

In certain embodiments, the present invention is directed to methods of treating a gastrointestinal disorder, comprising the step of administering to a patient in need thereof, an effective amount of a compound of formula I or II, or any combination thereof.

In certain preferred embodiments, the gastrointestinal disorders which may be treated with the present compounds and methods include, for example, nausea, vomiting, loss of appetite, cachexia, diarrhoea, inflammatory bowel disease, or irritable bowel syndrome, or any combination thereof.

In some embodiments, the present invention is directed to methods of treating inflammation, comprising the step of administering to a patient in need thereof, an effective amount of a compound of formula I or II, or any combination thereof.

In certain embodiments, the present invention is directed to methods of treating autoimmune diseases, comprising the step of administering to a patient in need thereof, an effective amount of a compound of formula I or II, or any combination thereof.

In some preferred embodiments, the autoimmune disease is multiple sclerosis, rheumatoid arthritis, psoriasis, Crohn's disease, systemic lupus erythematosus, myasthenia gravis, diabetes mellitus type I, cancer, glaucoma, osteoporosis, renal ischemia, cerebral stroke, cerebral ischemia, inflammatory bowel disease or irritable bowel syndrome, or nephritis, or any combination thereof.

In some embodiments, the present invention is directed to methods of inhibiting mechanical hyperalgesia associated with nerve injury, comprising the step of administering to a patient in need thereof, an effective amount of a compound of formula I or II, or any combination thereof.

In some embodiments, the present invention is directed to methods of treating an immune related disorder, comprising the step of administering to a patient in need thereof, an effective amount of a compound of formula I of II, or any combination thereof.

In certain preferred embodiments, the immune related disorder is asthma, chronic pulmonary obstructive disorder, emphysema, bronchitis, allergy, tissue rejection in organ transplants, celiac disease, or Sjögren's syndrome, or any combination thereof.

In certain embodiments, the present invention is directed to methods of treating pain, comprising the step of administering to a patient in need thereof, an effective amount of a compound of formula I of II, or any combination thereof.

In embodiments involving the treatment of pain, the pain may be inflammatory pain, neuropathic pain, visceral pain, surgical pain, including pain which occurs during surgery or pain which occurs after surgery (i.e., postsurgical pain), or cancer related pain. In certain more preferred embodiments, the present pain ameliorating methods may further comprise the administration to the patient of at least one opioid in the form of combination products and/or combination therapy. Suitable opioids include, for example, alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil or tramadol, and mixtures thereof. In embodiments involving the treatment or prevention of neuropathic pain, the present methods may further comprise administering to a patient codeine, carbamazepine, gabapentin, lamotrigine, phenyloin, amitryptiline, an NMDA receptor antagonist, an ion channel antagonist, or a nicotinic receptor agonist, or a mixture thereof, in the form of combination products and/or combination therapy.

In some preferred embodiments, the methods for treating pain may further comprise the administration to the patient of at least one cannabinoid.

In some embodiments, the present invention is directed to methods of treating hypertension, comprising the step of administering to a patient in need thereof, an effective amount of a compound of formula I of II, or any combination thereof.

In other embodiments, the present invention is directed to methods of providing cardioprotection against ischemic and reperfusion effects, comprising the step of administering to a patient in need thereof, an effective amount of a compound of formula I of II, or any combination thereof.

In certain preferred embodiments, the ischemic or reperfusion effect is arrhythmia or hypertension, or a combination thereof.

In some embodiments, the present invention is directed to methods of treating neurodegenerative diseases, comprising the step of administering to a patient in need thereof, an effective amount of a compound of formula I of II, or any combination thereof.

In some preferred embodiments, the neurodegenerative disease is Parkinson's disease, Alzheimer's disease, Huntington's disease, or amyotrophic lateral sclerosis. In certain more preferred embodiments, these methods may further comprise the administration to the patient of deprenyl, amantadine, levodopa, or carbidopa, in the form of combination products and/or combination therapy.

In other embodiments, the present invention is directed to methods of treating neurological disorders, comprising the step of administering to a patient in need thereof, an effective amount of a compound of formula I of II, or any combination thereof.

In certain preferred embodiments, the neurological disorder is stroke, migraine, or cluster headache, or any combination thereof.

In other embodiments, the present invention is directed to methods of inducing apoptosis in malignant cells, comprising the step of contacting said cells with an effective amount of a compound of formula I or II, or any combination thereof.

In some preferred embodiments, the apoptosis occurs in vitro. In other preferred embodiments, the apoptosis occurs in vivo.

In other embodiments, the present invention is directed to methods for modulating appetite, comprising the step of administering to a patient in need thereof, an effective amount of a compound of formula I or II, or any combination thereof. In some preferred embodiments, the modulating decreases appetite. In other preferred embodiments, the modulating enhances appetite.

Methods of Preparation

Employing the methodology herein described or cited, sulfamoyl benzamide compounds of Formula I or II can be readily prepared. The invention is further described in the following examples. Example 5 is actual in part (through intermediate 5.5) and prophetic in part (conversion of 5.5 to 5.6). Example 6 is prophetic. All other examples are actual examples. The examples herein provided are for illustrative purposes only and are not to be construed as limiting the appended claims. Certain of these examples provide a series of sulfamoyl benzamide derivatives of Formulae I and II, prepared as outlined in Schemes 1-3, shown below in examples 1A-2R.

Commercially available benzoic acid 1.1 was converted to the corresponding sulfonyl chloride 1.2 by heating in neat chlorosulfonic acid to 100° C. for 24 hours. The sulfonyl chloride 1.2 was reacted with 3 equivalents of the appropriate amine from the group Amine A in ethyl acetate to yield sulfonamide 1.3. Sulfonamide 1.3 was reacted with a second amine from the group Amine B and a suitable coupling reagent (e.g. DCC, Method 1a or TBTU, Method 1b) to afford sulfamoyl benzamide 1, or the sulfonamide 1.3 was converted to the acid chloride 1.4 and coupled with a second amine from the group Amine B to afford sulfamoyl benzamide 1. Compounds 1A-1AJ were prepared in this fashion (Scheme 1).

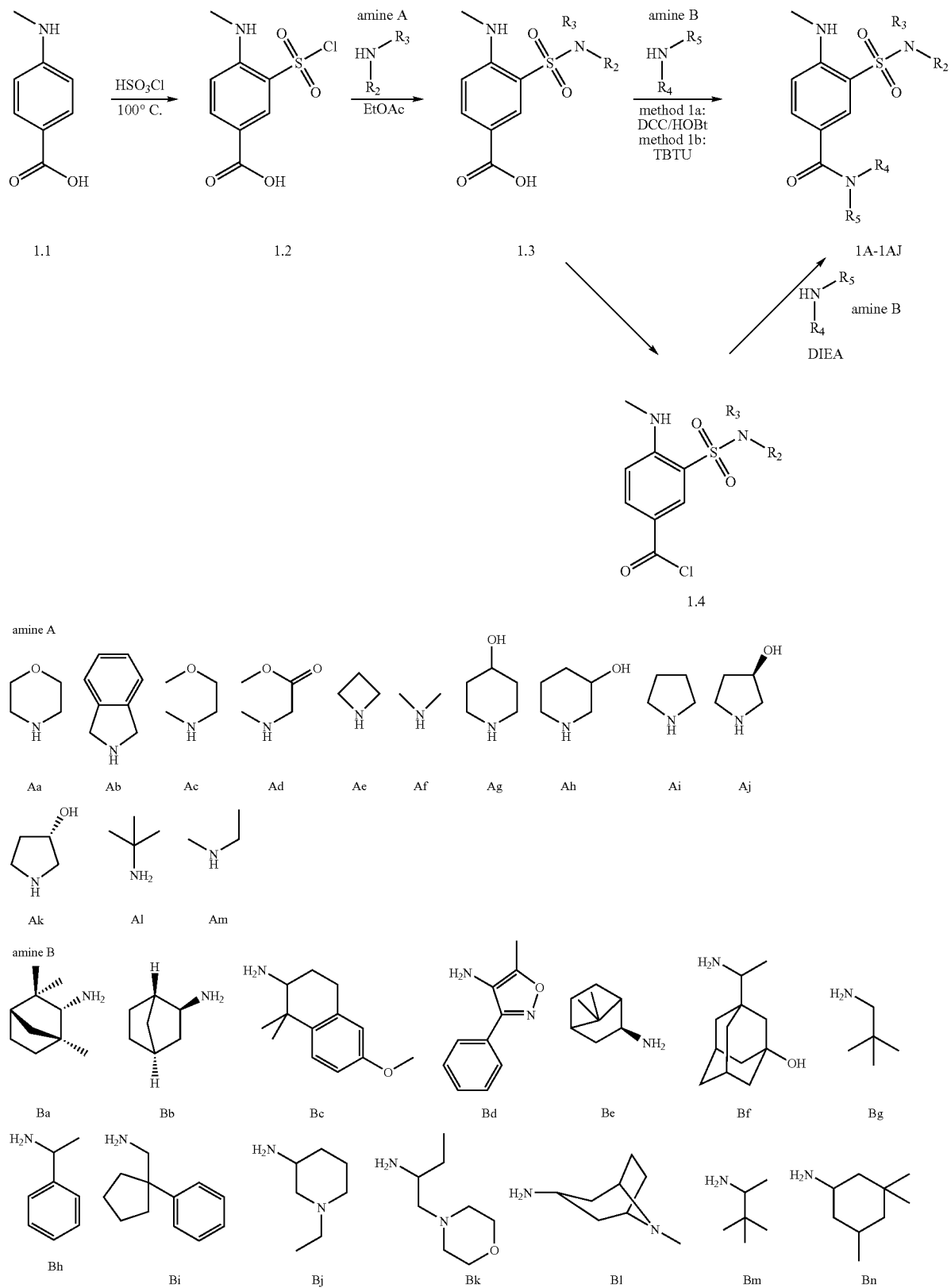
Scheme 1: Compounds 1A-1AJ

Bo

Commercially available benzoic acid 2.1 was converted to sulfonyl chloride 2.2 by heating in neat chlorosulfonic acid to 100° C. for 24 hours. The sulfonyl chloride 2.2 was reacted with 3 equivalents of the appropriate amine from the group Amine A in ethyl acetate to yield sulfonamide 2.3. Sulfonamide 2.3 was reacted with a second amine from the group Amine B and the coupling reagent TBTU to afford sulfamoyl benzamide 2.4. Replacement of the bromo-substituent with an amine from the group Amine C was accomplished by heating sulfamoyl benzamide 2.4 with the appropriate amine from the group Amine C neat or in dimethylformamide or toluene as solvent to 80-100° C. and addition of a Pd catalyst, providing compounds 2A-2H, 2I'-2L', and 2M-2R, as outlined in Scheme 2.

Scheme 2: Examples 2A-2H, 2I'-2L', and 2M-2R

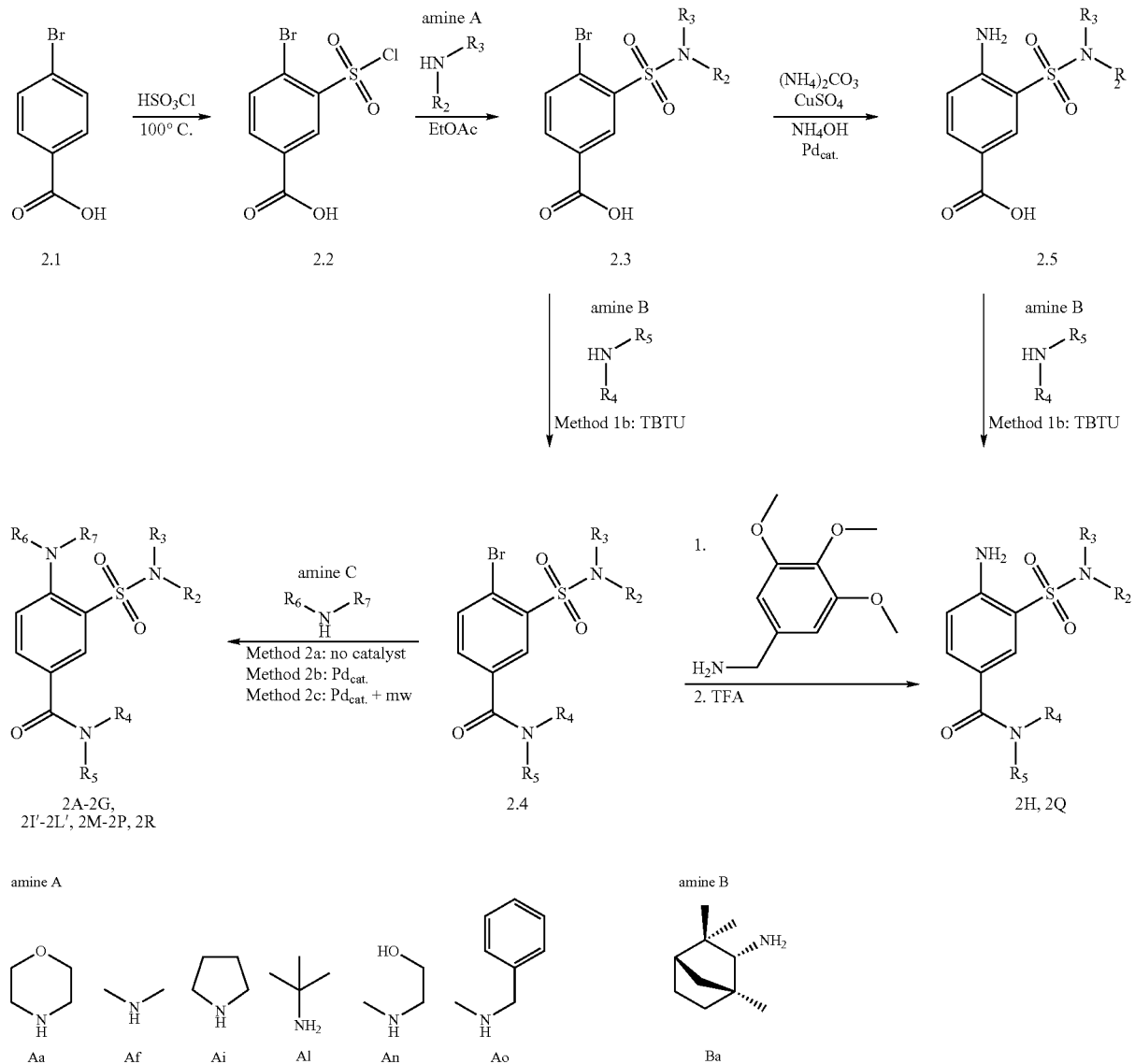

amine C
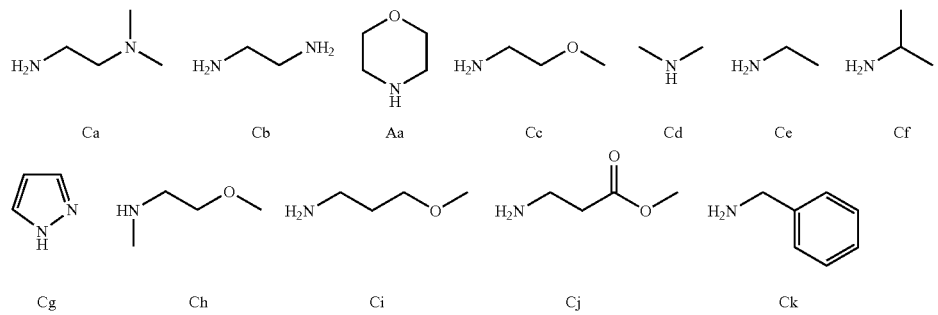
| Ca | Cb | Aa | Cc | Cd | Ce | Cf |
| Cg | Ch | Ci | Cj | Ck |
Compound 2I was obtained through heating 2.4 in benzyl alcohol directly. Compound 2J was obtained through hydrogenation of 2I. Compound 2K was formed through heating of 2.4 in methanol with a Pd catalyst. Compound 2L was obtained through heating 2.4 in methoxyethanol 3.3 directly (see Scheme 3).
Scheme 3: Examples 2I-2L
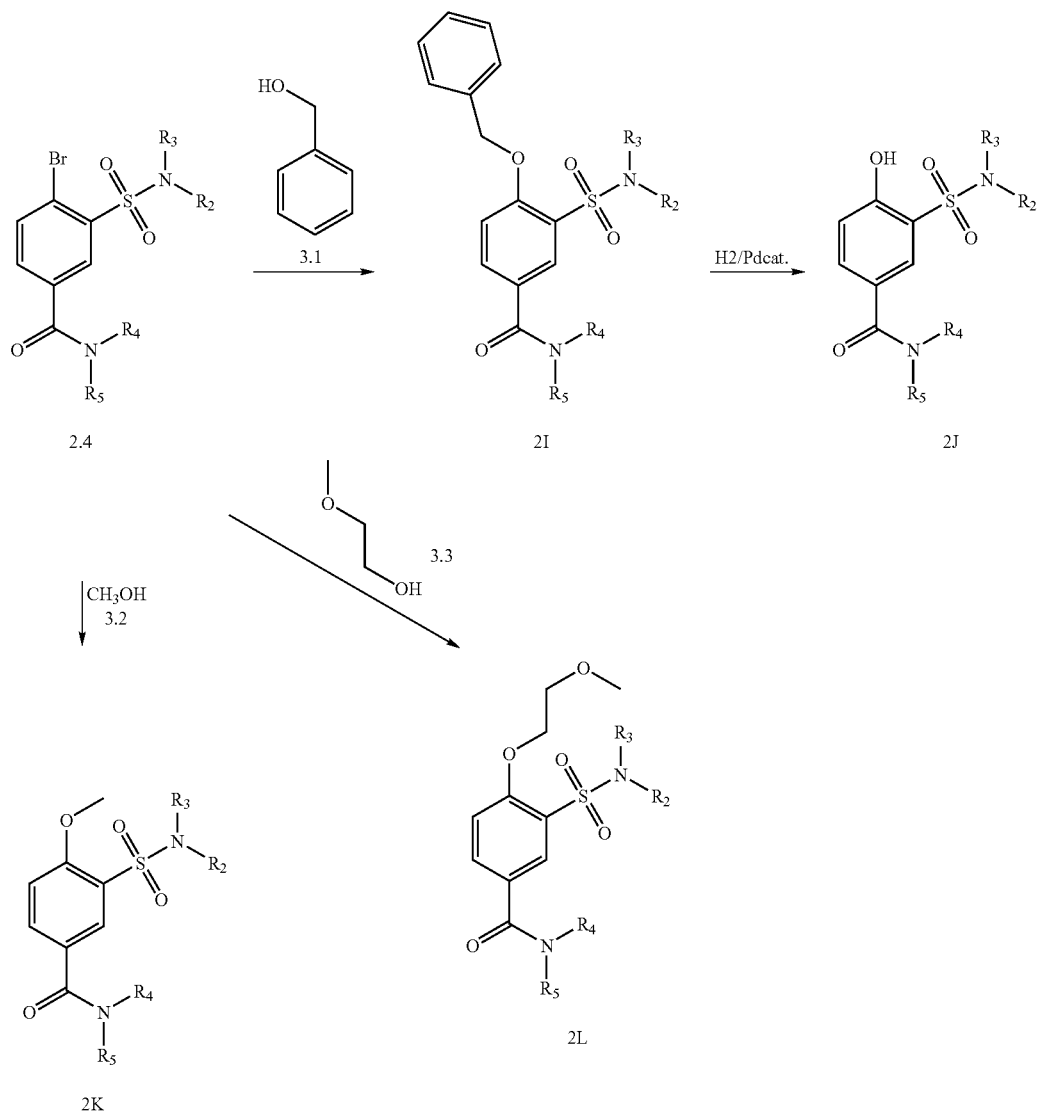

Other features of the invention will become apparent in the course of the following description of exemplary embodiments which are given for illustration of the invention and are not intended to be limiting thereof. Those skilled in the art of organic synthesis may be aware of still other synthetic routes to the invention compounds. The reagents and intermediates used herein are either commercially available or prepared according to standard literature procedures, unless otherwise described.

EXPERIMENTAL PROCEDURES

Materials: All chemicals were reagent grade, purchased from Sigma-Aldrich (Milwaukee, Wis.), and used without further purification. LC-MS data were obtained using a Thermo-Finnigan Surveyor HPLC and a Thermo-Finnigan AQA MS using positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

EXAMPLE 1A

Preparation of 3-(chlorosulfonyl)-4-(methylamino)benzoic acid (1.2)

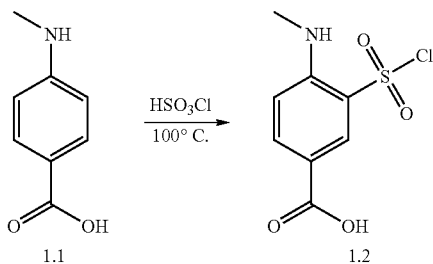

4-(Methylamino)benzoic acid (1.1, 3 g) was dissolved in 20 mL HSO₃Cl and heated to 100° C. for 48 hours. The mixture was cooled to room temperature and carefully poured on ice. A white precipitate formed, was collected and dried to yield 3-(chlorosulfonyl)-4-(methylamino)-benzoic acid (1.2) as an off-white powder (1.96 g, 39% yield). MS analysis (m+1)=248.

Preparation of 4-(methylamino)-3-(morpholinosulfonyl)benzoic acid (1.3.Aa)

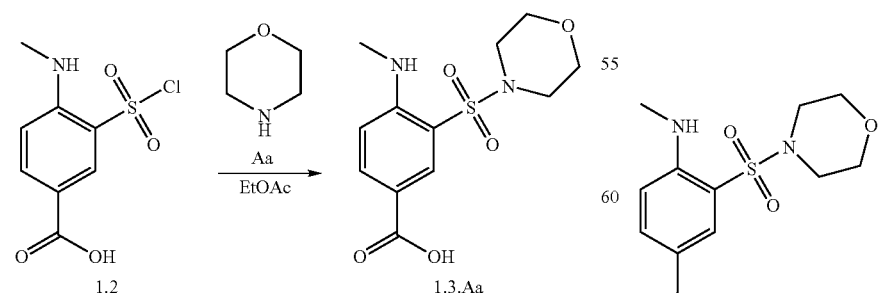

3-(Chlorosulfonyl)-4-(methylamino)benzoic acid (1.2, 1.0 g) was dissolved in 20 mL of ethyl acetate and morpholine (Aa, 1.0 mL, 3 eq) was added. The mixture was stirred at room temperature for 2 hours, then extracted with 15 mL of 0.5M HCl. The organic layer was washed with H₂O and brine, and the solvent evaporated to yield 4-(methylamino)-3-(morpholino-sulfonyl)-benzoic acid (1.3.Aa) as an off-white powder (0.30 g, 30% yield). MS analysis (m−1)=299.

Preparation of 4-(methylamino)-3-(morpholinosulfonyl)benzoyl chloride (1.4.Aa)

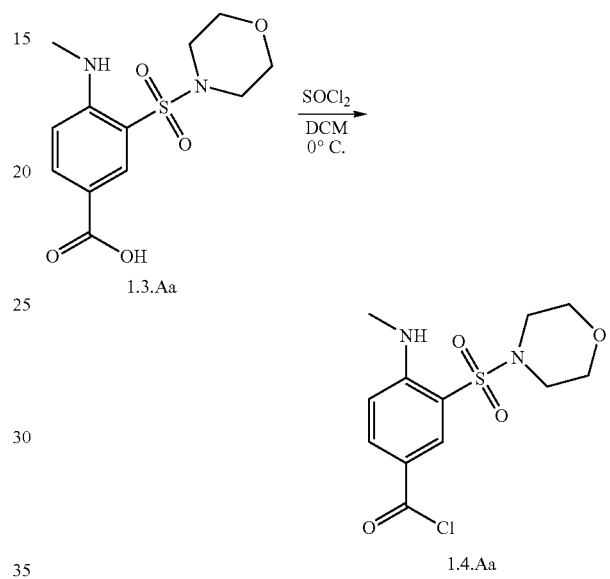

4-(Methylamino)-3-(morpholinosulfonyl)benzoic acid (1.3.Aa, 100 mg, 1 eq) was dissolved in 15 mL of dichloromethane under nitrogen. The mixture was put into an ice water bath and allowed to cool to 0° C. Thionyl chloride (0.4 mL, 1.2 eq) was then added. The reaction was left to stir for 72 hours. After a standard aqueous work-up, 286 mg of a sticky foam-like product was obtained (88.3% yield). MS analysis (m+1)=319.

Preparation of 4-(methylamino)-3-(morpholinosulfonyl)-N-((1S,4R)-1,3,3-trimethylbicyclo[2.2.1]heptan-2-yl)benzamide (1A)

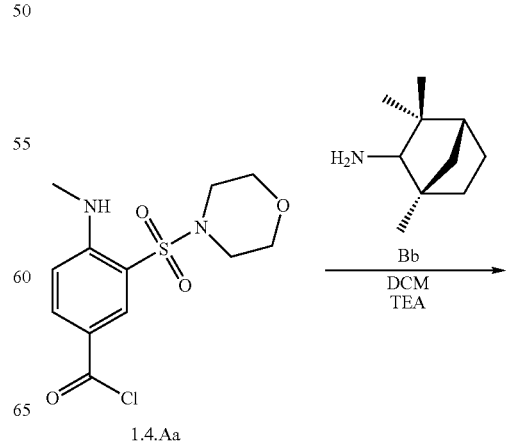

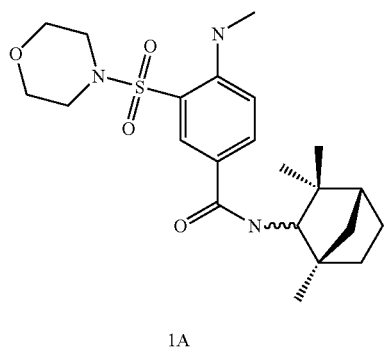

1A 4-(Methylamino)-3-(morpholinosulfonyl)benzoyl chloride (1.4.Aa, 100 mg, 1.5 eq) was dissolved in 8 mL of dry dichloromethane. Next, S-fenchyl amine (prepared as reported in FR96/01953) (Bb, 0.032 mL, 1 eq) was added. Triethylamine (0.030 mL, 1 eq) was then added. The progress of the reaction was monitored by TLC in 85% ethyl acetate: hexane. After 45 minutes the product was washed with $H_2O$, 1.0 M HCl, and brine. The dichloromethane was evaporated and crystals were obtained. The crude product 1A was purified on a silica gel column using hexane/ethyl acetate [66 mg of purified product was obtained (72% yield)]. MS analysis (m+1)=436.6. $^1$H NMR (CDCl$_3$), δ 0.84 (s, 3H), 1.10 (s, 3H), 1.18 (s, 3H), 1.26 (m, 3H), 1.51 (m, 1H), 1.61 (s, 2H), 1.72 (d, 2H), 1.81 (m, 1H), 2.91 (d, J=5 Hz, 3H), 3.08 (t, J=5 Hz, 4H), 3.72 (t, J=5 Hz, 4H), 3.81 (dd, J=9 Hz and 2 Hz, 1H), 5.93 (d, J=9 Hz, 1H), 6.63 (d, J=5 Hz, 1H), 6.75 (d, J=9 Hz, 1H), 7.83 (q, J=8 Hz and 2 Hz, 1H), 8.02 (d, J=2 Hz, 1H).

EXAMPLES 1B-1D

Compounds 1B-1D were prepared from 4-(methylamino)-3-(morpholinosulfonyl)-benzoyl chloride 1.4.Aa with N-((1R,2R,4S)-bicyclo-[2.2.1]heptanyl amine Bb (compound 1B), 6-methoxy-1,1-dimethyl-1,2,3,4-tetrahydronaphthalen-2-amine Bc (compound 1C) and 5-methyl-3-phenylisoxazol-4-amine Bd (compound 1D) respectively following the procedure described in Example 1A.

Compound 1B: $^1$H NMR (CDCl$_3$), δ 1.26 (m, 5H), 1.58 (m, 5H), 1.89 (m, 1H), 2.33 (d, J=1 Hz, 2H), 2.91 (d, J=5 Hz, 3H), 3.07 (t, J=5 Hz, 4H), 3.72 (t, J=5 Hz, 4H), 3.89 (q, J=3 Hz, 1H), 5.78 (d, J=4 Hz, 1H), 6.58 (d, J=4 Hz, 1H), 6.74 (d, J=9 Hz, 1H), 7.87 (dd, J=9 Hz and 2 Hz, 1H), 7.92 (d, J=2 Hz, 1H).

Compound 1C: $^1$H NMR (CDCl$_3$), δ 1.34 (s, 3H), 1.37 (s, 3H), 1.96 (m, 1H), 2.09 (m, 1H), 2.90 (d, J=5 Hz, 3H), 3.06 (t, J=5 Hz, 4H), 3.72 (t, J=5 Hz, 4H), 3.81 (s, 3H), 4.38 (m, 1H), 5.93 (d, J=9 Hz, 1H), 6.62 (m, 1H), 6.73 (m, J=9 Hz and 3 Hz, 2H), 6.89 (d, J=3 Hz, 1H), 7.03 (d, J=8 Hz, 1H), 7.76 (m, 1H), 7.97 (d, J=2 Hz, 1H).

Compound 1D: $^1$H NMR (CDCl$_3$), δ 2.47 (s, 3H), 2.94 (d, J=5 Hz, 3H), 3.07 (t, J=4 Hz, 4H), 3.73 (t, J=5 Hz, 4H), 6.74 (d, J=5 Hz, 1H), 6.79 (d, J=9 Hz, 1H), 7.09 (s, 1H), 7.44 (m, 3H), 7.66 (m, 2H), 7.95 (d, J=9 Hz, 1H), 8.07 (s, 1H).

EXAMPLE 1E

Preparation of 3-(isoindolin-2-ylsulfonyl)-4-(methylamino)benzoic acid (1.3.Ab)

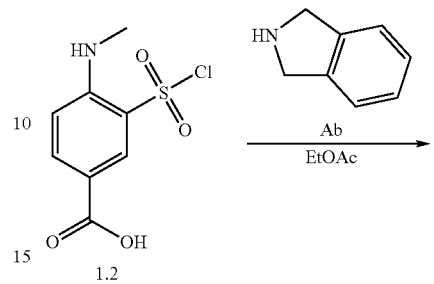

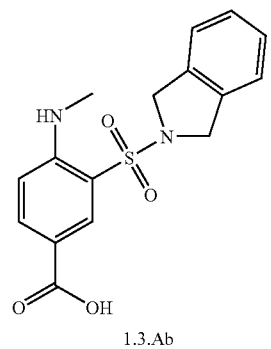

1.3.Ab 3-(Chlorosulfonyl)-4-(methylamino)benzoic acid 1.2 was reacted with isoindoline Ab following the procedure described in Example 1A. MS analysis (m−1)=331.

Preparation of 3-(isoindolin-2-ylsulfonyl)-4-(methylamino)-N-((1S,4R)-1,3,3-trimethylbicyclo[2.2.1]heptan-2-yl)-benzamide (1E)

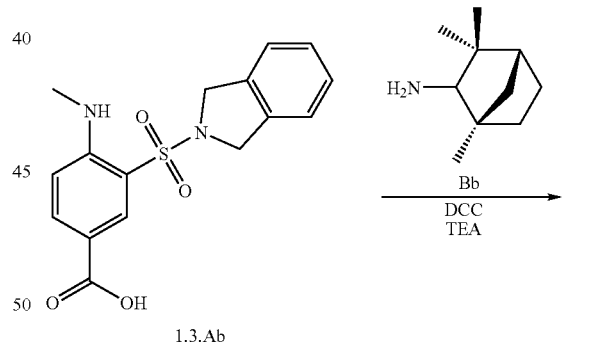

1.3.Ab

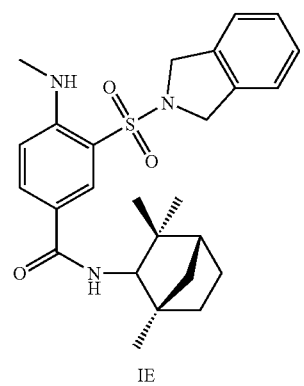

1E

Method 1a 3-(Isoindolin-2-ylsulfonyl)-4-(methylamino)benzoic acid (1.3.Ab, 4 mg, 0.012 mmol) in 300 μl N,N-dimethylformamide and PS—N,N'-dicyclohexylcarbodiimide resin (15 mg, loading ca. 1.27 mmol/g) were combined with 1-hydroxybenzotriazole (2 mg, 0.015 mmol) and fenchyl amine (Bb, 1.5 mg, 0.010 mmol). The reaction was shaken for 24 hours, then PS-trisamine resin (9 mg, loading ca. 4.36 mmol/g) was added and shaken overnight. The reaction was filtered and the N,N-dimethylformamide evaporated. 3-(isoindolin-2-ylsulfonyl)-4-(methylamino)-N-((1S,4R)-1,3,3-trimethyl-bicyclo[2.2.1]heptan-2-yl)-benzamide (1E) was obtained in 85% purity. MS analysis (m+1)=468.6. The abbreviation PS means polystyrene.

EXAMPLES 1F-1M

Compounds 1F-1M were prepared from 3-(isoindolin-2-ylsulfonyl)-4-(methyl-amino)benzoic acid (1.3.Ab), and an amine from group Amine B {N-((1R,2R,4S)-bicyclo-[2.2.1]heptanyl amine Bb (for compound 1F), N-((1R,2S,4R)-7,7-dimethylbicyclo[2.2.1]heptan-2-yl)-amine Be (for compound 1G), 3-(1,3-dihydro-isoindole-2-sulfonyl)-N-[1-(3-hydroxy-adamantan-1-yl-amine Bf (for compound 1H), neopentylamine Bg (for compound 1I), 1-phenylethyl amine Bh (for compound 1J), (1-phenylcyclopentyl)methan-amine Bi (for compound 1K), 1-ethylpiperidin-3-amine Bj (for compound 1L) or 1-morpholinobutan-2-amine Bk (for compound 1M)} respectively following the procedure outlined in Example 1E.

EXAMPLE 1N

Preparation of 3-(N-(2-methoxyethyl)-N-methylsulfamoyl)-4-(methylamino)benzoic acid (1.3.Ac)

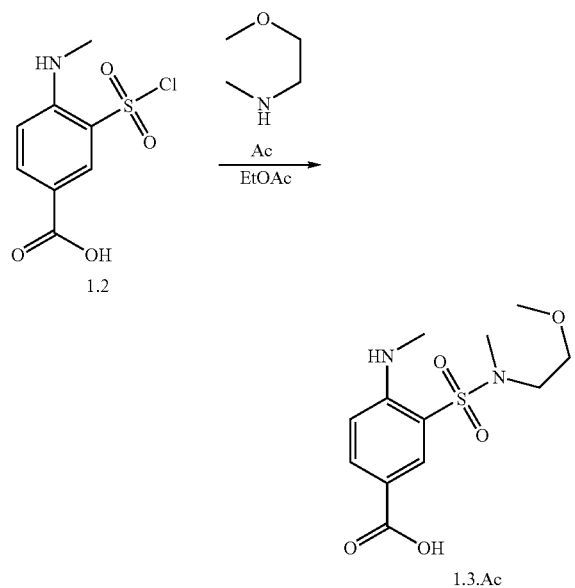

3-(Chlorosulfonyl)-4-(methylamino)benzoic acid 1.2 was reacted with 2-methoxy-N-methylethanamine Ac following the procedure described in Example 1A to provide 1.3.Ac. MS analysis (m−1)=301.

Preparation of 3-(N-(2-methoxyethyl)-N-methylsulfamoyl)-4-(methylamino)-N-((1S,4R)-1,3,3-trimethylbicyclo-[2.2.1]heptan-2-yl)benzamide (1N)

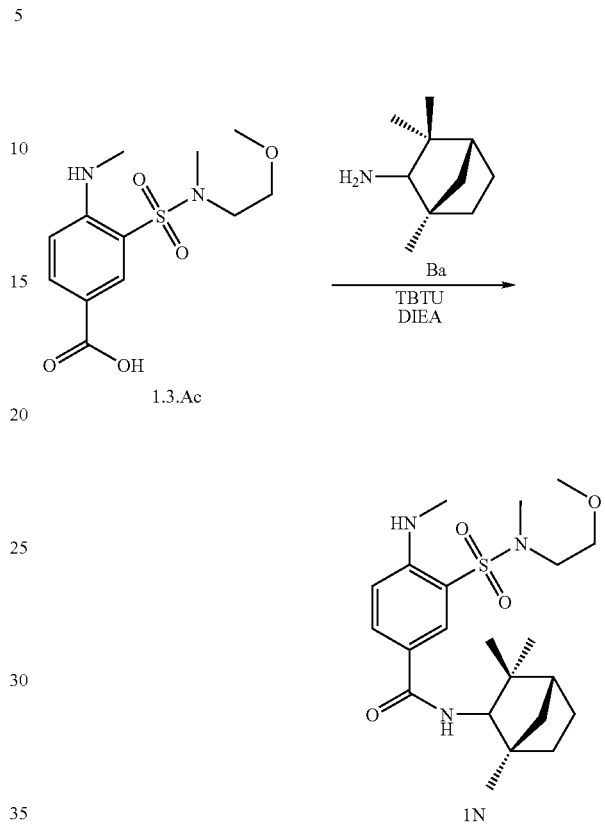

Method 1b 3-(N-(2-Methoxyethyl)-N-methylsulfamoyl)-4-(methylamino)benzoic acid (1.3.Ac, 0.133 g, 0.440 mmol), fenchyl amine (Ba, 0.1 mL, 0.9 mmol), and O-(benzotriazol-1-yl)-1,1,3,3-tetramethyluronium tetrafluoroborate (0.21 g, 0.66 mmol) were dissolved in dry acetonitrile (10 mL) under an atmosphere of nitrogen. The reaction was cooled to 0° C. in an ice water bath. Next, N,N-Diisopropylethylamine (0.3 mL, 2 mmol) was added. The reaction was left to stir for 48 hours at room temperature. The acetonitrile was then evaporated and ethyl acetate added. The product was extracted with saturated sodium bicarbonate (20 mL), and the organic layer was dried over magnesium sulfate. The product was purified by silica gel chromatography using a hexane/ethyl acetate eluent (10-50%) to yield 3-(N-(2-methoxyethyl)-N-methylsulfamoyl)-4-(methylamino)-N-((1S,4R)-1,3,3-trimethylbicyclo-[2.2.1]heptan-2-yl)benzamide (1N, 0.065 g, 34%). MS analysis (m+1)=438.6. Compound 1N: $^1$H NMR (CDCl$_3$), δ 0.84 (s, 3H), 1.09 (s, 3H), 1.17 (s, 3H), 1.27 (m, 3H), 1.50 (m, 1H), 1.61 (s, 2H), 1.71 (m, 1H), 1.80 (d, J=4 Hz, 1H), 2.17 (s, 2H), 2.83 (s, 3H), 2.92 (d, J=5 Hz, 3H), 3.37 (t, 2H), 3.54 (t, J=5 Hz, 2H), 3.81 (dd, J=9 Hz and 2 Hz, 1H), 5.96 (d, J=9 Hz, 1H), 6.57 (q, J=5 Hz, 1H), 6.73 (d, J=9 Hz, 1H), 7.85 (q, J=9 Hz and 2 Hz, 1H), 8.05 (d, J=2 Hz, 1H).

EXAMPLE 1O

Preparation of 3-(N-(2-methoxy-2-oxoethyl)-N-methylsulfamoyl)-4-(methylamino)-benzoic acid (1.3.Ad)

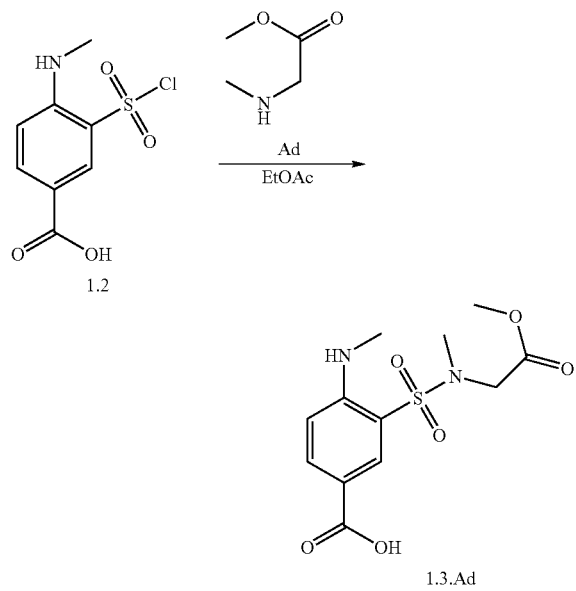

3-(Chlorosulfonyl)-4-(methylamino)benzoic acid 1.2 was reacted with methyl 2-(methylamino)acetate Ad following the procedure described in Example 1A.

MS analysis (m−1)=315.

Preparation of methyl 2-(N-methyl-2-(methylamino)-5-((1S,4R)-1,3,3-trimethyl-bicyclo-[2.2.1]heptan-2-ylcarbamoyl)phenylsulfonamido)-acetate (1O)

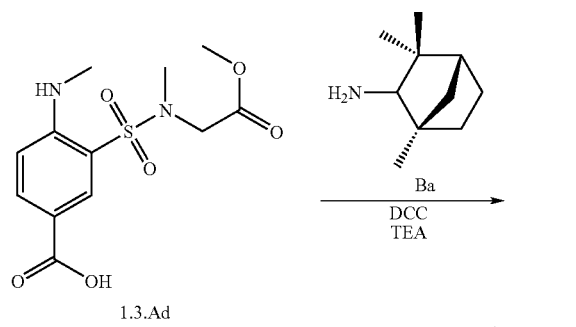

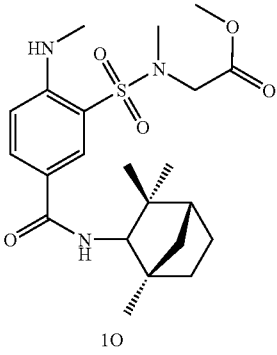

3-(N-(2-Methoxy-2-oxoethyl)-N-methylsulfamoyl)-4-(methylamino)-benzoic acid 1.3.Ad was reacted with fenchyl amine Ba following the procedure described in Example 1E (Method 1a). Methyl 2-(N-methyl-2-(methylamino)-5-((1S,4R)-1,3,3-trimethyl-bicyclo-[2.2.1]heptan-2-ylcarbamoyl)phenylsulfonamido)-acetate (1O) was obtained in 83% purity. MS analysis (m+1)=452.6.

EXAMPLES 1P–1V

Compounds 1P-1V were prepared from 3-(N-(2-methoxy-2-oxoethyl)-N-methylsulfamoyl)-4-(methylamino)-benzoic acid 1.3.Ad and amine B {N-((1R,2R,4S)-bicyclo-[2.2.1]heptanyl amine Bb (for compound 1P), N-((1R,2S,4R)-7,7-dimethylbicyclo[2.2.1]heptan-2-yl)-amine Be (for compound 1Q), 3-(1,3-Dihydro-isoindole-2-sulfonyl)-N-[1-(3-hydroxy-adamantan-1-yl-amine Bf (for compound 1R), neopentylamine Bg (for compound 1S), 1-phenylethyl amine Bh (for compound 1T), (1-phenylcyclopentyl)-methylamine Bi (for compound 1U) or 8-methyl-8-aza-bicyclo[3.2.1]octan-3-amine Bl (for compound 1V)} respectively following the procedure outlined in Example 1E.

EXAMPLE 1W

Preparation of 3-(azetidin-1-ylsulfonyl)-4-(methylamino)benzoic acid (1.3.Ae)

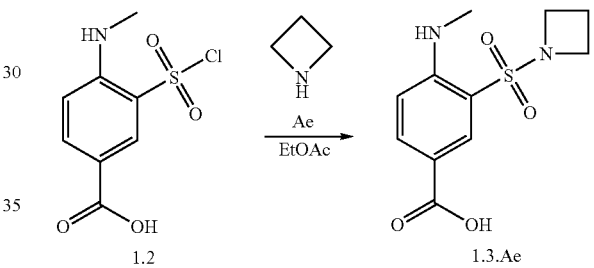

Azetidine Ae (HCl salt) (0.2 g, 2 mmol) was dissolved in ethyl acetate (8 mL). Triethylamine (0.3 mL, 2 mmol) and 3-(chlorosulfonyl)-4-(methylamino)benzoic acid (1.2, 0.1 g, 0.5 mmol) were added. The reaction was left to stir for 4 hours, then extracted with 0.5 M HCl, washed with water and brine, and dried over magnesium sulfate. The ethyl acetate was evaporated and 3-(azetidin-1-ylsulfonyl)-4-(methylamino)-benzoic acid (1.3.Ae) was obtained (0.08 g, 60% yield). MS analysis (m−1)=269.

Preparation of 3-(azetidin-1-ylsulfonyl)-4-(methylamino)-N-((1S,4R)-1,3,3-trimethylbicyclo-[2.2.1]heptan-2-yl)benzamide (1W)

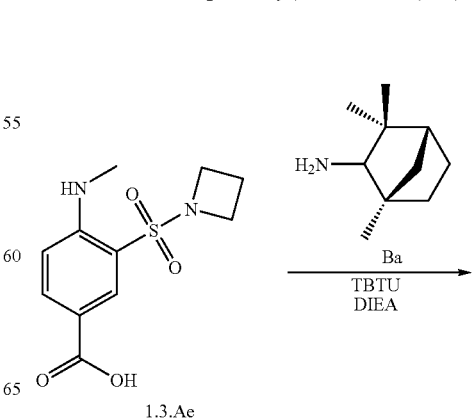

-continued

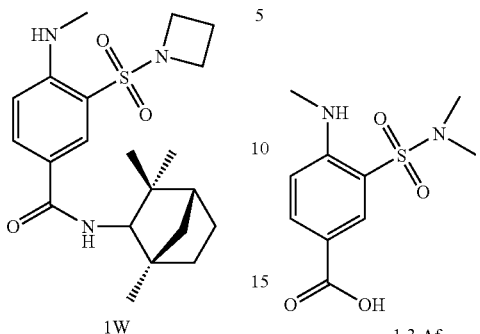

1W 3-(Azetidin-1-ylsulfonyl)-4-(methylamino)benzoic acid (1.3.Ae, 0.2 g, 0.7 mmol), fenchyl amine (Ba, 0.2 mL, 1 mmol), and O-(benzotriazol-1-yl)-1,1,3,3-tetramethyluronium tetrafluoroborate (0.33 g, 1 mmol) were dissolved in dry acetonitrile (15 mL) under an atmosphere of nitrogen. The reaction was cooled to 0° C. in an ice water bath and N,N-diisopropylethylamine (0.5 mL, 3 mmol) was added. After work-up and purification as described in Example 1N (method 1b), 3-(azetidin-1-ylsulfonyl)-4-(methylamino)-N-((1S,4R)-1,3,3-trimethylbicyclo-[2.2.1]heptan-2-yl)benzamide (1W) was obtained as an off-white solid (0.03 g, 10% yield). MS analysis (m+1)=406.6.

EXAMPLE 1X

Preparation of 3-(N,N-dimethylsulfamoyl)-4-(methylamino)benzoic acid (1.3.Af)

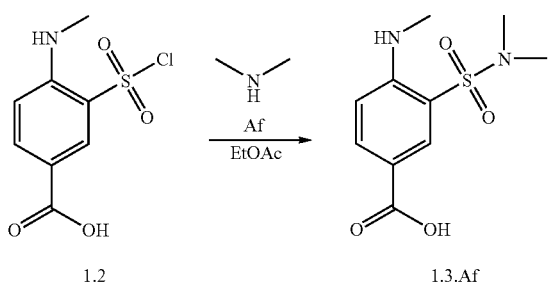

3-(Chlorosulfonyl)-4-(methylamino)benzoic acid (1.2, 0.515 g, 2.06 mmol) was dissolved in ethyl acetate (8 mL, 0.08 mol). Dimethylamine (0.4 mL, 0.008 mol) was added next. The reaction was left to stir for 4 hours. The reaction was extracted with 0.5 M HCl, washed with water and brine, and the organic layer dried over magnesium sulfate. The ethyl acetate was evaporated and the crude product 1.3.Af was obtained in 92% yield. MS analysis (m−1)=257.

Preparation of 3-(N,N-dimethylsulfamoyl)-4-(methylamino)-N-((1S,2S,4R)-1,3,3-trimethylbicyclo[2.2.1]heptan-2-yl)benzamide (1X)

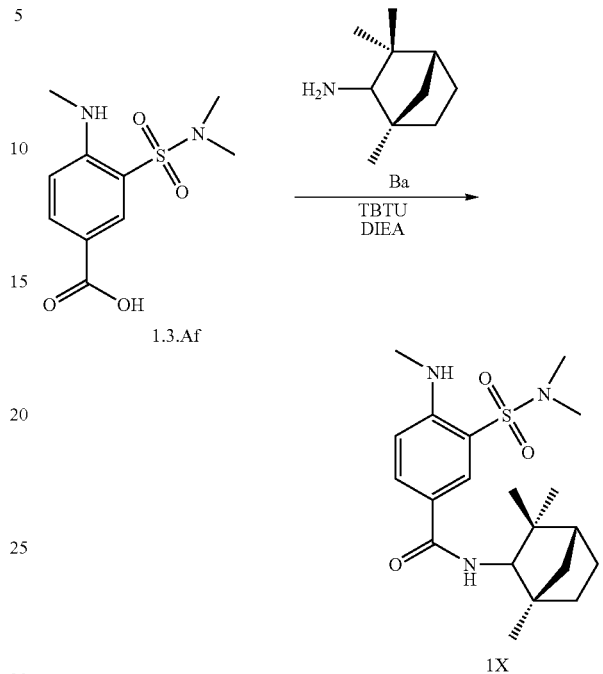

3-(N,N-Dimethylsulfamoyl)-4-(methylamino)benzoic acid (1.3.Af, 0.2000 g, 0.7743 mmol), fenchyl amine (Ba, 0.2373 mL, 1.549 mmol), and O-(benzotriazol-1-yl)-1,1,3,3-tetreamethyluronium tetrafluoroborate (TBTU, 0.3729 g, 1.161 mmol) were dissolved in 10 mL of dry acetonitrile under nitrogen. The reaction was cooled to 0° C. in an ice water bath. N,N-Diisopropylethylamine (0.5395 mL, 3.097 mmol) was then added. The reaction was left to stir for 24 hours. The acetonitrile was evaporated off and ethyl acetate was added. The solution was then washed with sodium hydrogen carbonate and the organic layer was dried over magnesium sulfate. After the ethyl acetate was evaporated off, the compound was purified by silica gel column chromatography using an ethyl acetate/hexane gradient. The product 1X was obtained in 13% yield. MS analysis (m+1)=394.2. Compound 1X: $^1$H NMR (CDCl$_3$), δ 0.84 (s, 3H), 1.09 (s, 3H), 1.17 (s, 3H), 1.27 (m, 3H), 1.51 (m, 1H), 1.61 (s, 2H), 1.71 (m, 2H), 1.80 (t, J=2 Hz, 1H), 2.76 (s, 6H), 2.92 (d, J=5 Hz, 3H), 3.81 (q, J=9 Hz and 2 Hz, 1H), 5.95 (d, J=10 Hz, 1H), 6.65 (d, J=5 Hz, 1H), 6.75 (d, J=9 Hz, 1H), 7.85 (q, J=9 Hz and 2 Hz, 1H), 7.99 (d, J=2 Hz, 1H).

EXAMPLE 1Y

Preparation of N-((1R,2R,4S)-bicyclo-[2.2.1]heptan-2-yl)-3-(N,N-dimethylsulfamoyl)-4-(methylamino)benzamide (1Y)

Compound 1Y was prepared from 3-(chlorosulfonyl)-4-(methylamino)benzoic acid (1.2) and amine Af according to the procedure described in Example 1A, followed by an amide formation with amine Bb according to Method 1b. Compound 1Y: $^1$H NMR (CDCl$_3$), δ 1.28 (m, 5H), 1.53 (m, 2H), 1.89 (m, 2H), 1.99 (br s, 5H), 2.33 (br s, 2H), 2.75 (s, 6H), 2.91 (s, 2H), 3.89 (m, 4H), 5.85 (d, 1H), 6.62 (br s, 1H), 6.74 (d, J=9 Hz, 1H), 7.87 (d, J=9 Hz, 1H), 7.90 (s, 1H).

EXAMPLE 1Z

Preparation of 3-(4-hydroxypiperidin-1-ylsulfonyl)-4-(methylamino)-N-((1S,4R)-1,3,3-trimethylbicyclo[2.2.1]heptan-2-yl)benzamide (1Z)

Compound 1Z was prepared from 3-(chlorosulfonyl)-4-(methylamino)benzoic acid (1.2) and amine Ag according to the procedure described in Example 1A, followed by an amide formation with amine Ba according to Method 1b.

Compound 1Z: $^1$H NMR (CDCl$_3$), δ 0.84 (s, 3H), 1.09 (s, 3H), 1.17 (s, 3H), 1.27 (m, 3H), 1.45 (d, J=4 Hz, 1H), 1.58 (s, 5H), 1.63 (m, 2H), 1.71 (m, 2H), 1.80 (t, J=2 Hz, 1H), 1.92 (m, 2H), 2.91 (d, J=5 Hz, 3H), 2.94 (m, 1H), 3.42 (m, 2H), 3.81 (m, 2H), 5.94 (d, J=9 Hz, 1H), 6.62 (d, J=5 Hz, 1H), 6.73 (d, J=9 Hz, 1H), 7.82 (dd, J=9 Hz and 2 Hz, 1H), 8.01 (d, J=2 Hz, 1H).

EXAMPLE 1AA

Preparation of 3-(3-hydroxypiperidin-1-ylsulfonyl)-4-(methylamino)-N-((1S,4R)-1,3,3-trimethylbicyclo[2.2.1]heptan-2-yl)benzamide (1AA)

Compound 1AA was prepared from 3-(chlorosulfonyl)-4-(methylamino)benzoic acid (1.2) and amine Ah according to the procedure described in Example 1A, followed by an amide formation with amine Ba according to Method 1b.

Compound 1AA: $^1$H NMR (CDCl$_3$), δ 0.84 (s, 3H), 1.10 (s, 3H), 1.17 (s, 3H), 1.27 (m, 3H), 1.54 (m, 6H), 1.71 (m, 3H), 1.80 (m, 2H), 2.92 (d, J=5 Hz, 3H), 3.01 (m, 2H), 3.13 (m, 1H), 3.31 (dd, J=13 Hz and 3 Hz, 1H), 3.49 (s, 3H), 3.81 (d, J=9 Hz, 1H), 3.86 (m, 1H), 5.95 (d, J=9 Hz, 1H), 6.57 (m, 1H), 6.75 (d, J=9 Hz, 1H), 7.84 (q, J=9 Hz and 2 Hz, 1H), 8.03 (d, J=2 Hz, 1H).

EXAMPLES 1AB-1AD

Preparations of 4-(methylamino)-3-(pyrrolidin-1-ylsulfonyl)-N-((1S,4R)-1,3,3-trimethyl-bicyclo[2.2.1]heptan-2-yl)benzamide (1AB), N-((1R,2R,4S)-bicyclo-[2.2.1]heptan-2-yl)-4-(methylamino)-3-(pyrrolidin-1-ylsulfonyl)-benzamide (1AC) and N-(3,3-dimethylbutan-2-yl)-4-(methylamino)-3-(pyrrolidin-1-ylsulfonyl)-benzamide (1AD)

Compounds 1AB-1AD were prepared from 3-(chlorosulfonyl)-4-(methylamino)benzoic acid (1.2) and amine Ai according to the procedure described in Example 1A, followed by an amide formation according to Method 1b with amines Ba for compound 1AB, with amine Bb for compound 1AC and with amine Bm for compound 1AD respectively.

Compound 1AB: $^1$H NMR (CDCl$_3$), δ 0.84 (s, 3H), 1.09 (s, 3H), 1.17 (s, 3H), 1.26 (m, 3H), 1.52 (m, 9H), 1.71 (m, 2H), 1.83 (m, 5H), 2.91 (d, J=5 Hz, 3H), 3.28 (m, 3H), 3.81 (q, J=9 Hz and 2 Hz, 1H), 5.95 (d, J=8 Hz, 1H), 6.69 (t, J=4 Hz, 1H), 6.74 (d, J=9 Hz, 1H), 7.84 (q, J=9 Hz and 2 Hz, 1H), 8.04 (d, J=2 Hz, 1H).

Compound 1AC: $^1$H NMR (CDCl$_3$), δ 1.25 (m, 4H), 1.39 (m, 1H), 1.50 (m, 2H), 1.57 (m, 5H), 1.83 (m, 5H), 2.32 (d, J=4 Hz, 2H), 2.91 (d, J=5 Hz, 3H), 3.27 (t, J=7 Hz, 4H), 3.89 (m, 1H), 5.80 (t, J=3 Hz, 1H), 6.64 (dd, J=8 Hz and 3 Hz, 1H), 6.73 (d, J=9 Hz, 1H), 7.88 (dd, J=8 Hz and 2 Hz, 1H), 7.95 (d, J=2 Hz, 1H).

Compound 1AD: $^1$H NMR (CDCl$_3$), δ 0.96 (s, 9H), 1.15 (d, J=7 Hz, 3H), 1.59 (s, 2H), 1.84 (t, J=7 Hz, 4H), 2.91 (d, J=5 Hz, 3H), 3.28 (t, J=7 Hz, 4H), 4.10 (m, 1H), 5.79 (d, J=10 Hz, 1H), 6.66 (t, J=5 Hz, 1H), 6.74 (d, J=9 Hz, 1H), 7.86 (dd, J=9 Hz and 2 Hz, 1H), 8.00 (d, J=2 Hz, 1H).

EXAMPLE 1AE

Preparation of 4-(methylamino)-3-(pyrrolidin-1-ylsulfonyl)-N-(3,3,5-trimethylcyclohexyl)-benzamide (1AE)

Compound 1AE was prepared from 3-(chlorosulfonyl)-4-(methylamino)benzoic acid (1.2) and amine Ai, followed by an amide formation with amine Bn according to the procedures described in Example 1A.

Compound 1AE: $^1$H NMR (CDCl$_3$), δ 0.91 (d, J=7 Hz, 3H), 0.96 (s, 3H), 1.00 (s, 3H), 1.39 (m, 1H), 1.58 (s, 6H), 1.74 (m, 2H), 1.83 (m, 4H), 2.08 (m, 1H), 2.91 (d, J=5 Hz, 3H), 3.27 (t, J=7 Hz, 4H), 4.14 (m, 1H), 5.74 (d, J=8 Hz, 1H), 6.63 (m, 1H), 6.73 (d, J=9 Hz, 1H), 7.90 (dd, J=9 Hz and 2 Hz, 1H), 7.95 (d, J=2 Hz, 1H).

EXAMPLE 1AF

Preparation of 3-((R)-3-hydroxypyrrolidin-1-ylsulfonyl)-4-(methylamino)-N-((1S,4R)-1,3,3-trimethylbicyclo[2.2.1]heptan-2-yl)benzamide (1AF)

Compound 1AF was prepared from 3-(chlorosulfonyl)-4-(methylamino)benzoic acid (1.2) and amine Aj according to the procedure described in Example 1A, followed by an amide formation with amine Ba according to Method 1b.

Compound 1AF: $^1$H NMR (CDCl$_3$), δ 0.83 (s, 3H), 0.88 (s, 2H), 1.02 (s, 2H), 1.09 (m, 4H), 1.17 (s, 3H), 1.25 (m, 2H), 1.45 (m, 2H), 1.71 (m, 3H), 1.80 (t, J=2 Hz, 1H), 1.92 (m, 6H), 2.92 (d, 3H), 3.42 (m, 4H), 3.80 (dd, J=9 Hz and 2 Hz, 1H), 4.43 (q, 1H), 5.97 (d, J=9 Hz, 1H), 6.66 (q, J=10 Hz and 5 Hz, 1H), 6.74 (d, J=9 Hz, 1H), 7.82 (dd, J=9 Hz and 2 Hz, 1H), 8.06 (d, J=2 Hz, 1H).

EXAMPLE 1AG

Preparation of 3-((S)-3-hydroxypyrrolidin-1-ylsulfonyl)-4-(methylamino)-N-((1S,4R)-1,3,3-trimethylbicyclo[2.2.1]heptan-2-yl)benzamide (1AG)

Compound 1AG was prepared from 3-(chlorosulfonyl)-4-(methylamino)benzoic acid (1.2) and amine Ak according to the procedure described in Example 1A, followed by an amide formation with amine Ba according to Method 1b.

Compound 1AG: $^1$H NMR (CDCl$_3$), δ 0.84 (s, 3H), 0.88 (m, 1H), 0.97 (m, 1H), 1.09 (s, 3H), 1.17 (s, 3H), 1.26 (t, J=7 Hz, 3H), 1.71 (m, 2H), 1.80 (t, J=2 Hz, 1H), 1.92 (m, 1H), 2.00 (m, 1H), 2.92 (d, J=5 Hz, 2H), 3.42 (m, 3H), 3.49 (m, 3H), 3.81 (dd, J=9 Hz and 2 Hz, 1H), 4.43 (m, 1H), 5.97 (m, 1H), 6.66 (m, 1H), 6.74 (d, J=9 Hz, 1H), 7.82 (dd, J=8 Hz and 2 Hz, 1H), 8.07 (d, J=2 Hz, 1H).

EXAMPLE 1AH

Preparation of N-adamantan-1-yl-4-methylamino-3-(morpholine-4-sulfonyl)-benzamide (1AH)

Compound 1AH was prepared from 3-(chlorosulfonyl)-4-(methylamino)benzoic acid (1.2) and amine Aa according to the procedure described in Example 1A, followed by an amide formation with amine Bo according to Method 1b.

Compound 1AH: $^1$H NMR (CDCl$_3$), δ 1.57 (s, 3H), 1.72 (s, 6H), 2.12 (s, 9H), 2.90 (d, J=5 Hz, 3H), 3.08 (t, J=5 Hz, 4H), 3.72 (t, J=5 Hz, 4H), 5.64 (s, 1H), 6.56 (q, J=5 Hz, 1H), 6.73 (d, J=9 Hz, 1H), 7.82 (dd, J=9 Hz and 2 Hz, 1H), 7.92 (d, J=2 Hz, 1H).

EXAMPLE 1AI

Preparation of 3-(N-tert-butylsulfamoyl)-4-(methylamino)-N-((1S,4R)-1,3,3-trimethylbicyclo-[2.2.1]heptan-2-yl)benzamide (1AI)

Compound 1AI was prepared from 3-(chlorosulfonyl)-4-(methylamino)benzoic acid (1.2) and amine Al according to the procedure described in Example 1A, followed by an amide formation with amine Ba according to Method 1b.

Compound 1AI: $^1$H NMR (CDCl$_3$), δ 0.83 (s, 3H), 1.09 (s, 3H), 1.17 (s, 3H), 1.21 (s, 9H), 1.26 (m, 4H), 1.50 (m, 1H), 1.57 (s, 6H), 1.71 (dd, J=12 Hz and 4 Hz, 2H), 1.80 (t, J=2 Hz, 1H), 2.17 (s, 1H), 2.96 (d, J=5 Hz, 3H), 3.82 (dd, J=9 Hz and 2 Hz, 1H), 4.58 (s, 1H), 5.97 (d, J=9 Hz, 1H), 6.15 (t, J=4 Hz, 1H), 6.77 (d, J=9 Hz, 1H), 7.90 (dd, J=9 Hz and 2 Hz, 1H), 8.13 (d, J=2 Hz, 1H).

EXAMPLE 1AJ

Preparation of 3-(N-ethyl-N-methylsulfamoyl)-4-(methylamino)-N-((1S,4R)-1,3,3-trimethylbicyclo[2.2.1]heptan-2-yl)benzamide (1AJ)

Compound 1AJ was prepared from 3-(chlorosulfonyl)-4-(methylamino)benzoic acid (1.2) and amine Am, followed by an amide formation with amine Ba according to the procedures described in Example 1A.

Compound 1AJ: $^1$H NMR (CDCl$_3$), δ 0.84 (s, 3H), 1.09 (s, 3H), 1.15 (q, 7H), 1.26 (m, 3H), 1.51 (m, 1H), 1.71 (m, 2H), 1.80 (t, J=2 Hz, 1H), 2.17 (s, 1H), 2.78 (s, 3H), 2.92 (d, J=5 Hz, 3H), 3.19 (q, J=7 Hz, 2H), 3.81 (dd, J=9 Hz and 2 Hz, 1H), 5.95 (d, J=9 Hz, 1H), 6.57 (d, J=4 Hz, 1H), 6.73 (d, J=9 Hz, 1H), 7.82 (dd, J=9 Hz and 2 Hz, 1H), 8.01 (d, J=2 Hz, 1H).

EXAMPLE 2A

Preparation of 4-Bromo-3-chlorosulfonyl-benzoic acid (2.2)

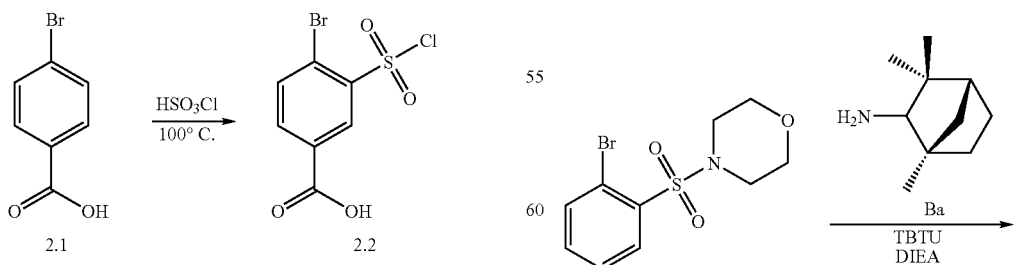

4-Bromobenzoic acid (2.1, 10 g) was dissolved in 60 mL HSO$_3$Cl and heated to 100° C. for 24 hours. The mixture was cooled to room temperature and carefully poured on ice. A white precipitate formed, was collected and dried to yield 4-bromo-3-chlorosulfonyl-benzoic acid (2.2) as a white powder (13.75 g, 97% yield). See EP0659748 for further details. MS analysis (m−1)=296.

Preparation of 4-Bromo-3-(morpholinosulfonyl)-benzoic acid (2.3.Aa)

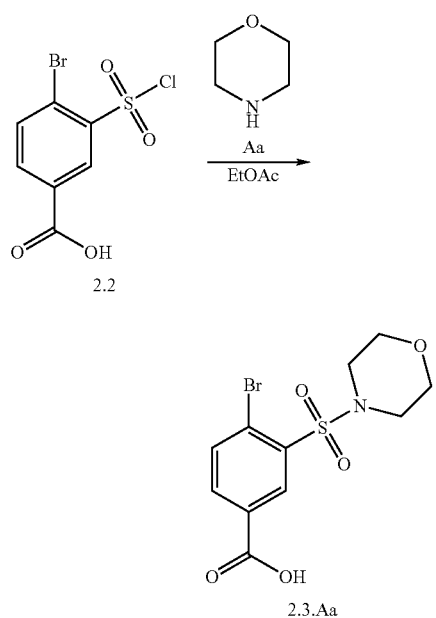

4-Bromo-3-chlorosulfonyl-benzoic acid (2.2, 1.1 g) was dissolved in 20 mL of ethyl acetate and morpholine (Aa, 1.48 mL, 3 eq) was added. The mixture was stirred at room temperature for 2 hours, then extracted with 15 mL of 0.5M HCl. The organic layer was washed with H$_2$O and brine and the solvent evaporated to yield 4-bromo-3-(morpholinosulfonyl)-benzoic acid (2.3.Aa) as an off-white powder (1.13 mg, 88% yield). MS analysis (m−1)=348.

Preparation of 4-bromo-3-(morpholinosulfonyl)-N-((1S,4R)-1,3,3-trimethylbicyclo-[2.2.1]heptan-2-yl)benzamide (2.4.AaBa)

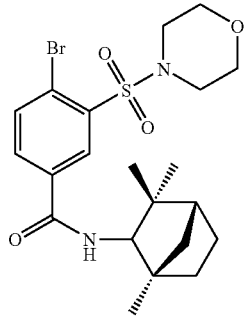

2.4.AaBa

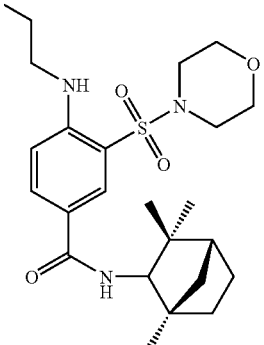

2A

In a round bottom flask, 2.70 g 4-bromo-3-(morpholinosulfonyl)-benzoic acid (2.3.Aa, 7.7 mmol), 2.92 g S-fenchyl amine hydrochloride Ba (prepared as reported in FR96/01953) (15.4 mmol, 2 eq) and 3.71 mg O-(benzotriazol-1-yl)-1,1,3,3-tetramethyluronium tetrafluoroborate (11.55 mmol, 1.5 eq) were stirred in 10 ml dry acetonitrile. The mixture was cooled to 0° C. and 5.37 mL diisopropylethylamine (30.8 mmol, 4 eq) were added dropwise. The mixture was stirred overnight. The solvent was evaporated, ethyl acetate added, and the mixture was extracted with sat. NaHCO$_3$, dried over Mg$_2$SO$_4$ and purified via SiO$_2$ chromatography (5-20% ethyl acetate/hexane) to provide 4-bromo-3-(morpholinosulfonyl)-N-((1S,4R)-1,3,3-trimethylbicyclo-[2.2.1]heptan-2-yl)benzamide (2.4.AaBa) as an off-white solid. (1.61 g, 43% yield). MS analysis (m+1)=485.

Preparation of 4-(2-(dimethylamino)ethylamino)-3-(morpholinosulfonyl)-N-((1S,4R)-1,3,3-trimethylbicyclo[2.2.1]heptan-2-yl)benzamide (2A)

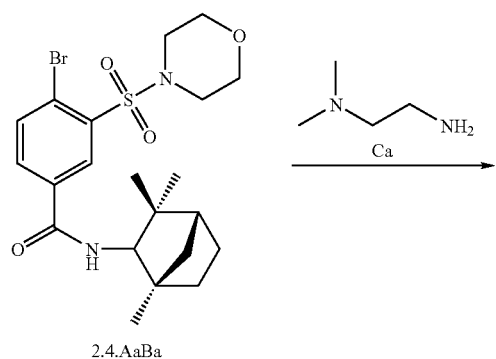

2.4.AaBa

Method 2a

4-Bromo-3-(morpholinosulfonyl)-N-((1S,4R)-1,3,3-trimethylbicyclo-[2.2.1]heptan-2-yl)benzamide (2.4.AaBa, 0.675 g, 1.39 mmol)) was dissolved in 1.5 mL N$^1$,N$^1$-dimethyl-ethane-1,2-diamine Ca and heated to 100° C. overnight. After cooling to room temperature, ethyl acetate (10 mL) was added and the solution was washed with 1M HCl, water, brine, dried over Mg$_2$SO$_4$, and purified via SiO$_2$ chromatography (5-20% ethyl acetate/hexane) to provide 4-(2-(dimethylamino)ethylamino)-3-(morpholinosulfonyl)-N-((1S,4R)-1,3,3-trimethylbicyclo[2.2.1]heptan-2-yl)benzamide (2A) as an off-white solid (0.21 mg, 31% yield). MS analysis (m+1)=493.7.

Compound 2A: $^1$H NMR (DMSO), δ 0.79 (s, 3H), 1.00 (s, 3H), 1.07 (s, 3H), 1.19 (d, J=9 Hz, 1H), 1.42 (m, 1H), 1.63 (d, J=11 Hz, 1H), 1.71 (d, J=4 Hz, 1H), 1.86 (m, 1H), 2.18 (s, 6H), 2.96 (t, J=5 Hz, 4H), 3.25 (q, J=5 Hz, 2H), 3.62 (t, J=5 Hz, 4H), 3.74 (dd, J=9 Hz and 2 Hz, 1H), 6.77 (t, J=5 Hz, 1H), 6.85 (d, J=9 Hz, 1H), 7.33 (d, J=9 Hz, 1H), 7.99 (d, J=2 Hz, 1H), 8.04 (q, J=9 Hz and 2 Hz, 1H).

EXAMPLES 2B-2D

Preparations of 4-(2-aminoethylamino)-3-(morpholinosulfonyl)-N-((1S,4R)-1,3,3-trimethylbicyclo [2.2.1]heptan-2-yl)benzamide (2B), 4-morpholino-3-(morpholinosulfonyl)-N-((1S,4R)-1,3,3-trimethylbicyclo-[2.2.1]heptan-2-yl)benzamide (2C), and 4-(2-methoxyethylamino)-3-(morpholinosulfonyl)-N-((1S,4R)-1,3,3-trimethylbicyclo[2.2.1]heptan-2-yl)benzamide (2D)

Compounds 2B-2D were prepared from 4-bromo-3-(morpholinosulfonyl)-N-((1S,4R)-1,3,3-trimethylbicyclo-[2.2.1]heptan-2-yl)benzamide (2.4.AaBa) and ethylene diamine Cb (compound 2B), morpholine Aa (compound 2C), or 2-methoxy-ethylamine Cc (compound 2D) respectively following the procedure outlined in Example 2A.

Compound 2B: $^1$H NMR (DMSO), δ 0.80 (s, 3H), 1.02 (s, 3H), 1.08 (s, 3H), 1.22 (d, J=10 Hz, 1H), 1.43 (m, 1H), 1.63 (m, 2H), 1.71 (t, J=2 Hz, 1H), 2.83 (t, J=7 Hz, 2H), 3.01 (t, J=5 Hz, 4H), 3.31 (t, 3H), 3.61 (t, J=5 Hz, 4H), 3.74 (d, J=2 Hz, 1H), 6.88 (d, J=9 Hz, 1H), 7.84 (dd, J=9 Hz and 2 Hz, 1H), 7.98 (d, J=2 Hz, 1H).

Compound 2C: $^1$H NMR (DMSO), δ 0.90 (s, 3H), 1.10 (s, 3H), 1.17 (m, 4H), 1.28 (dd, J=10 Hz and 1 Hz, 2H), 1.48 (m, 1H), 1.75 (m, 5H), 2.05 (m, 8H), 3.09 (m, 8H), 3.65 (t, J=5 Hz, 4H), 3.80 (t, J=5 Hz, 4H), 3.87 (dd, J=9 Hz and 2 Hz, 1H), 7.18 (m, 1H), 7.53 (d, J=8 Hz, 1H), 8.11 (dd, J=8 Hz and 2 Hz, 1H), 8.34 (d, J=2 Hz, 1H).

Compound 2D: ¹H NMR (CDCl₃), δ 0.84 (s, 3H), 1.09 (s, 3H), 1.17 (s, 3H), 1.27 (m, 2H), 1.50 (m, 1H), 1.59 (s, 6H), 1.70 (m, 2H), 1.80 (t, J=2 Hz, 1H), 3.10 (t, J=5 Hz, 4H), 3.39 (m, 5H), 3.63 (t, J=5 Hz, 2H), 3.72 (t, J=5 Hz, 4H), 3.81 (dd, J=9 Hz and 2 Hz, 1H), 5.92 (q, J=9 Hz, 1H), 6.77 (m, 2H), 7.82 (q, J=9 Hz and 2 Hz, 1H), 8.03 (d, J=2 Hz, 1H).

EXAMPLE 2E

Preparation of 4-(dimethylamino)-3-(morpholinosulfonyl)-N-((1S,4R)-1,3,3-trimethylbicyclo[2.2.1]heptan-2-yl)benzamide (2E)

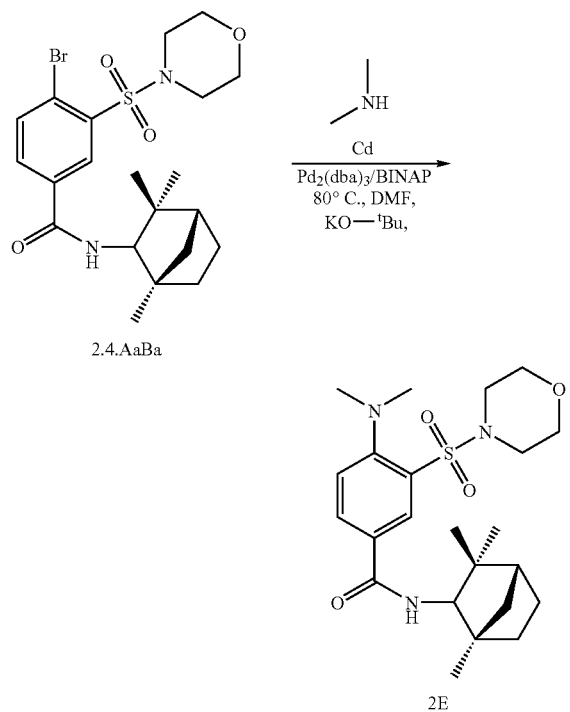

Method 2b

4-Bromo-3-(morpholinosulfonyl)-N-((1S,4R)-1,3,3-trimethylbicyclo[2.2.1]heptan-2-yl)benzamide (2.4.AaBa, 0.400 g, 0.824 mmol), dimethylamine (Cd, 2 mL 2M in THF), and 3 mL N,N-dimethylformamide were mixed. Tris(dibenzylideneacetone)dipalladium(0) (0.08 g, 0.08 mmol), (R)-(+)-2,2'-bis(diphenylphosphino)-1,1'-binaphthyl (0.05 g, 0.08 mmol), and potassium tert-butoxide (0.9 g, 8 mmol) were then added. The reaction was heated to at 100° C. for 24 hours. After aqueous workup and acidic extraction, the organic layer was evaporated to yield a yellow solid. The product was then purified by SiO₂ chromatography (5-20% ethyl acetate/hexane) to yield 4-(dimethylamino)-3-(morpholinosulfonyl)-N-((1S,4R)-1,3,3-trimethylbicyclo[2.2.1] heptan-2-yl)benzamide (2E) as an off-white solid (180 mg, 49% yield). MS analysis (m+1)=450.6.

Compound 2E: ¹H NMR (DMSO), δ 0.90 (s, 3H), 1.10 (s, 3H), 1.17 (m, 4H), 1.27 (dd, J=10 Hz and 1 Hz, 1H), 1.49 (m, 1H), 1.75 (m, 4H), 2.81 (m, 7H), 3.12 (t, J=5 Hz, 4H), 3.64 (t, J=5 Hz, 4H), 3.87 (q, J=9 Hz and 2 Hz, 1H), 7.14 (m, 1H), 7.50 (d, J=8 Hz, 1H), 8.05 (q, J=8 Hz and 2 Hz, 1H), 8.34 (d, J=2 Hz, 1H).

EXAMPLES 2F-2G

Preparations of 4-(ethylamino)-3-(morpholinosulfonyl)-N-((1S,4R)-1,3,3-trimethylbicyclo-[2.2.1]heptan-2-yl)benzamide (2F) and 4-(isopropylamino)-3-(morpholinosulfonyl)-N-((1S,4R)-1,3,3-trimethylbicyclo[2.2.1]-heptan-2-yl)benzamide (2G)

Compounds 2F-2G were prepared from 4-bromo-3-(morpholinosulfonyl)-N-((1S,4R)-1,3,3-trimethylbicyclo[2.2.1] heptan-2-yl)benzamide (2.4.AaBa) and ethylamine Ce (2M solution in THF, compound 2F) or isopropylamine Cf (compound 2G) respectively.

EXAMPLE 2H

Preparation of 3-(morpholinosulfonyl)-4-(3,4,5-trimethoxybenzylamino)-N-((1S,4R)-1,3,3-trimethylbicyclo[2.2.1]heptan-2-yl)benzamide (2.5.AaBa)

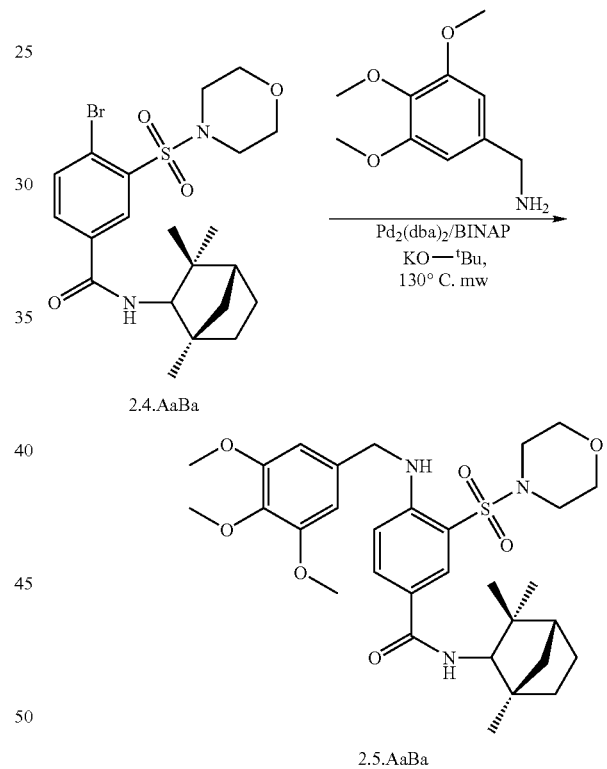

Method 2c

Into a microwave flask, 4-bromo-3-(morpholinosulfonyl)-N-((1S,4R)-1,3,3-trimethylbicyclo[2.2.1]heptan-2-yl)benzamide (2.4.AaBa, 0.3 g, 0.0006 mol) was dissolved in (3,4,5-trimethoxyphenyl)methanamine (2 mL, 0.01 mol). Bis (dibenzylideneacetone)-palladium(0) (0.02 g, 0.00003 mol), (R)-(+)-2,2'-bis(diphenylphosphino)-1,1'-binaphthyl (0.02 g, 0.00003 mol), and potassium tert-butoxide (0.08 mL, 0.0006 mol) were then added. The microwave oven flask was sealed and the reaction was heated at 130° C. for 1 h. The reaction underwent aqueous workup. The product was obtained in 80% yield and used crude for the next step. MS analysis (m+1)=602.

Preparation of 4-amino-3-(morpholinosulfonyl)-N-((1S,4R)-1,3,3-trimethylbicyclo-[2.2.1]heptan-2-yl)benzamide (2H)

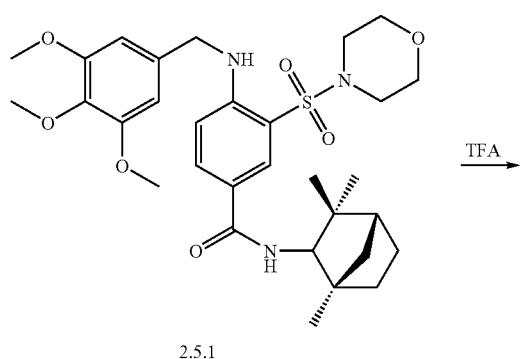

2.5.1

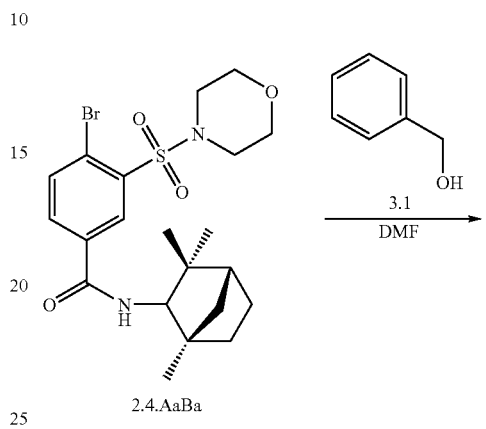

2H 3-(Morpholinosulfonyl)-4-(3,4,5-trimethoxybenzylamino)-N-((1S,4R)-1,3,3-trimethylbicyclo[2.2.1]heptan-2-yl)benzamide (2.5.AaBa, 0.36 g, 0.00060 mol) was dissolved in trifluoroacetic acid (7 mL, 0.09 mol). The reaction was stirred overnight at room temperature. The reaction was evaporated to dryness and the residue underwent aqueous workup. Prep-HPLC was performed to isolate the desired product, a white, crystalline solid 2H in 40% yield. MS analysis (m+1)=422.6.

Compound 2H: $^1$H NMR (CDCl$_3$), δ 0.84 (s, 3H), 1.10 (s, 3H), 1.17 (s, 3H), 1.26 (m, 3H), 1.53 (m, 1H), 1.72 (dd, J=10 Hz and 2 Hz, 2H), 1.81 (t, J=2 Hz, 1H), 3.12 (t, J=5 Hz, 4H), 3.73 (t, J=5 Hz, 4H), 3.80 (dd, J=9 Hz and 2 Hz, 1H), 5.96 (d, J=10 Hz, 1H), 6.77 (d, J=9 Hz, 1H), 7.71 (dd, J=9 Hz and 2 Hz, 1H), 7.99 (d, J=2 Hz, 1H).

EXAMPLE 2I

Preparation of 4-(benzyloxy)-3-(morpholinosulfonyl)-N-((1S,4R)-1,3,3-trimethylbicyclo[2.2.1]heptan-2-yl)benzamide (2I)

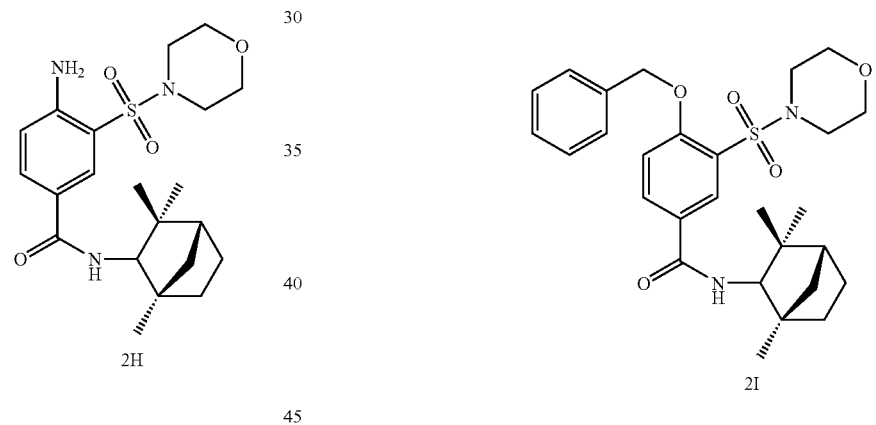

4-Bromo-3-(morpholinosulfonyl)-N-((1S,4R)-1,3,3-trimethylbicyclo[2.2.1]heptan-2-yl)benzamide (2.4.AaBa, 1.00 g, 2.06 mmol) benzyl alcohol (3.1, 0.256 mL, 0.00247 mol) were dissolved in 10 mL dimethylformamide. The reaction was heated to 100° C. for 18 hours. Ethyl acetate (20 mL) was added and aqueous workup was performed. The organic layer was dried over magnesium sulfate evaporated and purified via SiO$_2$ chromatography (16%-33% ethyl acetate/hexane) to yield 4-(benzyloxy)-3-(morpholinosulfonyl)-N-((1S,4R)-1,3,3-trimethylbicyclo[2.2.1]heptan-2-yl)benzamide (2I) as a white solid. MS analysis (m+1)=513.7.

Compound 2I: $^1$H NMR (CDCl$_3$), δ 0.84 (s, 3H), 1.10 (s, 3H), 1.18 (s, 3H), 1.28 (m, 4H), 1.50 (m, 2H), 1.71 (m, 2H), 1.81 (t, J=2 Hz, 1H), 2.01 (s, 2H), 3.14 (t, J=5 Hz, 4H), 3.56 (t, J=5 Hz, 4H), 3.82 (dd, J=9 Hz and 2 Hz, 1H), 5.25 (s, 2H), 6.03 (d, J=9 Hz, 1H), 7.14 (d, J=9 Hz, 1H), 7.40 (m, 3H), 7.51 (d, J=8 Hz, 2H), 8.02 (dd, J=9 Hz and 2 Hz, 1H), 8.24 (d, J=2 Hz, 1H).

EXAMPLE 2J

Preparation of 4-hydroxy-3-(morpholinosulfonyl)-N-((1S,4R)-1,3,3-trimethylbicyclo[2.2.1]heptan-2-yl)benzamide (2J)

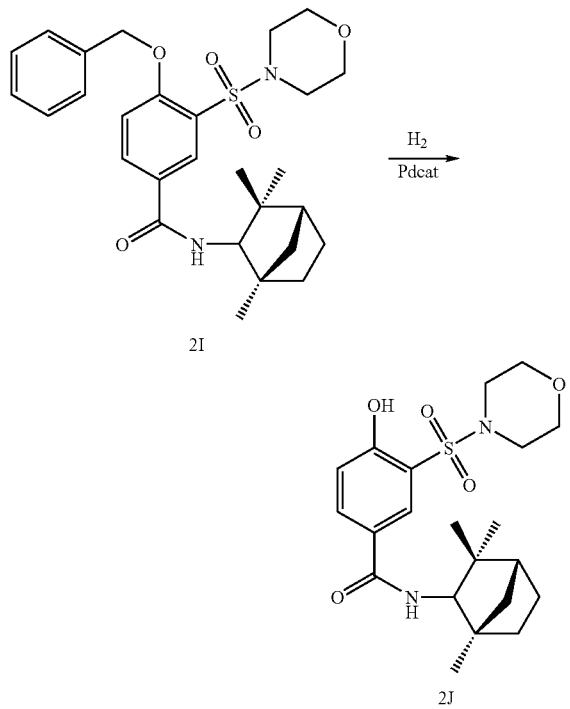

4-(Benzyloxy)-3-(morpholinosulfonyl)-N-((1S,4R)-1,3,3-trimethylbicyclo[2.2.1]heptan-2-yl)benzamide (2I) was hydrogenated under standard conditions to yield 4-hydroxy-3-(morpholinosulfonyl)-N-((1S,4R)-1,3,3-trimethylbicyclo[2.2.1]heptan-2-yl)benzamide (2J) quantitatively. MS analysis (m+1)=423.2.

Compound 2J: $^1$H NMR (CDCl$_3$), δ 0.85 (s, 3H), 1.11 (s, 3H), 1.18 (s, 3H), 1.29 (m, 3H), 1.41 (m, 1H), 1.53 (m, 1H), 1.72 (m, 2H), 1.82 (d, J=4 Hz, 1H), 3.09 (t, J=5 Hz, 4H), 3.76 (t, J=5 Hz, 4H), 3.81 (q, J=9 Hz and 1 Hz, 1H), 6.05 (d, J=9 Hz, 1H), 7.13 (d, J=9 Hz, 1H), 7.82 (dd, J=9 Hz and 2 Hz, 1H), 8.02 (d, J=2 Hz, 1H), 9.14 (br s, 1H).

EXAMPLE 2K

Preparation of 4-methoxy-3-(morpholinosulfonyl)-N-((1S,4R)-1,3,3-trimethylbicyclo[2.2.1]heptan-2-yl)benzamide (2K)

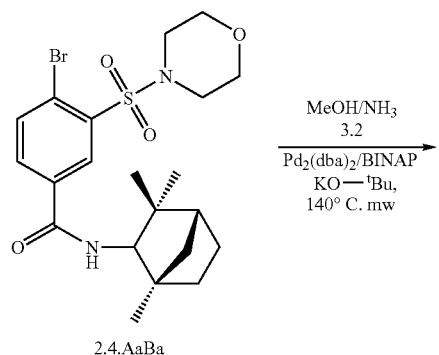

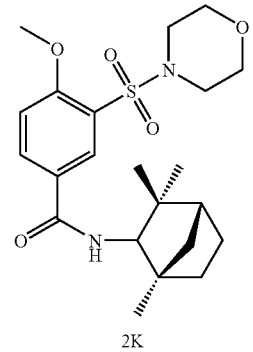

Into a 5 mL microwave flask 4-bromo-3-(morpholinosulfonyl)-N-((1S,4R)-1,3,3-trimethylbicyclo[2.2.1]heptan-2-yl)benzamide (2.4.AaBa, 0.3 g, 0.6 mmol) was dissolved in methanol (2 mL, 0.05 mol). Bis(dibenzylideneacetone)palladium(0) (0.02 g, 0.03 mmol), (R)-(+)-2,2'-bis(diphenylphosphino)-1,1'-binaphthyl (0.02 g, 0.03 mmol), and potassium tert-butoxide (0.5 mL, 4 mmol) were then added. The reaction was heated in the microwave oven at 140° C. for 1 h. The solvent was evaporated and prep-HPLC was performed to yield product 2K in 20% yield as a white, crystalline solid. MS analysis (m+1)=437.6.

Compound 2K: $^1$H NMR (CDCl$_3$), δ 0.78 (s, 3H), 1.03 (s, 3H), 1.11 (s, 3H), 1.21 (m, 4H), 1.44 (m, 2H), 1.54 (s, 2H), 1.65 (m, 2H), 1.74 (t, J=2 Hz, 1H), 3.20 (t, J=5 Hz, 4H), 3.66 (t, J=5 Hz, 4H), 3.75 (dd, J=9 Hz and 2 Hz, 2H), 3.93 (s, 3H), 5.97 (d, J=10 Hz, 1H), 7.03 (d, J=9 Hz, 1H), 7.99 (q, J=9 Hz and 2 Hz, 1H), 8.14 (d, J=3 Hz, 1H).

EXAMPLE 2L

Preparation of 4-(2-methoxyethoxy)-3-(morpholinosulfonyl)-N-((1S,4R)-1,3,3-trimethylbicyclo[2.2.1]heptan-2-yl)benzamide (2L)

Compound 2L was prepared from 4-bromo-3-(morpholinosulfonyl)-N-((1S,4R)-1,3,3-trimethylbicyclo[2.2.1]heptan-2-yl)benzamide 2.4.AaBa and 2-methoxyethanol 3.3 following the procedure described in Example 2I.

Compound 2L: $^1$H NMR (CDCl$_3$), δ 0.85 (s, 3H), 1.10 (s, 3H), 1.18 (s, 3H), 1.28 (m, 3H), 1.52 (m, 1H), 1.71 (m, 2H), 1.81 (t, J=2 Hz, 1H), 3.30 (t, J=5 Hz, 4H), 3.41 (s, 3H), 3.72 (t, J=5 Hz, 4H), 3.81 (m, 3H), 4.28 (m, 2H), 6.02 (d, J=9 Hz, 1H), 7.10 (d, J=9 Hz, 1H), 8.02 (dd, J=9 Hz and 2 Hz, 1H), 8.22 (d, J=2 Hz, 1H).

EXAMPLES 2I'-2L'

Preparation of 3-(morpholinosulfonyl)-4-(1H-pyrazol-1-yl)-N-((1S,4R)-1,3,3-trimethylbicyclo[2.2.1]heptan-2-yl)benzamide (2I'), 4-((2-methoxyethyl)-(methyl)-amino)-3-(morpholinosulfonyl)-N-((1S,4R)-1,3,3-trimethylbicyclo-[2.2.1]heptan-2-yl)benzamide (2J') 4-((3-methoxypropyl)-amino)-3-(morpholinosulfonyl)-N-((1S,4R)-1,3,3-trimethylbicyclo-[2.2.1]heptan-2-yl)benzamide (2K') and methyl 3-(2-(morpholinosulfonyl)-4-((1S,4R)-1,3,3-trimethyl-bicyclo[2.2.1]-heptan-2-ylcarbamoyl)-phenyl)amino)propanoate (2L')

Compounds 2I'-2L' were prepared from 4-bromo-3-(morpholinosulfonyl)-N-((1S,4R)-1,3,3-trimethylbicyclo[2.2.1]

heptan-2-yl)benzamide (2.4.AaBa) and amine Cg (for compound 2I'), amine Ch (for compound 2J'), amine Ci (for compound 2K') and Cj (for compound 2L') respectively, following Method 2c.

Compound 2I': $^1$H NMR (CDCl$_3$), δ 0.88 (s, 3H), 1.13 (s, 3H), 1.21 (s, 3H), 1.30 (m, 3H), 1.42 (m, 3H), 1.53 (m, 1H), 1.72 (m, 2H), 1.84 (d, J=3 Hz, 1H), 2.89 (t, J=5 Hz, 4H), 3.49 (t, J=5 Hz, 4H), 3.86 (dd, J=9 Hz and 1 Hz, 1H), 6.12 (d, J=9 Hz, 1H), 6.48 (t, J=2 Hz, 1H), 7.65 (d, J=8 Hz, 1H), 7.80 (d, J=2 Hz, 1H), 8.08 (m, 2H), 8.48 (d, J=2 Hz, 1H).

Compound 2J': $^1$H NMR (CDCl$_3$), δ 0.85 (s, 3H), 1.10 (s, 3H), 1.18 (s, 3H), 1.27 (m, 3H), 1.52 (m, 1H), 1.70 (m, 2H), 1.81 (t, J=2 Hz, 1H), 2.89 (s, 3H), 3.17 (t, J=5 Hz, 4H), 3.32 (m, 5H), 3.59 (t, J=6 Hz, 2H), 3.71 (t, J=5 Hz, 4H), 3.82 (q, J=9 Hz and 2 Hz, 1H), 6.05 (d, J=9 Hz, 1H), 7.40 (d, J=8 Hz, 1H), 7.96 (dd, J=8 Hz and 2 Hz, 1H), 8.27 (d, J=2 Hz, 1H).

Compound 2K': $^1$H NMR (CDCl$_3$), δ 0.84 (s, 3H), 1.09 (s, 3H), 1.17 (m, 4H), 1.27 (m, 3H), 1.51 (m, 1H), 1.71 (m, 2H), 1.80 (d, J=4 Hz, 1H), 1.92 (m, 2H), 3.10 (t, J=5 Hz, 4H), 3.31 (q, J=7 Hz, 2H), 3.36 (s, 3H), 3.51 (t, J=6 Hz, 2H), 3.72 (t, J=5 Hz, 4H), 3.81 (dd, J=9 Hz and 1 Hz, 1H), 5.94 (d, J=9 Hz, 1H), 6.78 (d, J=9 Hz, 1H), 6.82 (t, J=5 Hz, 1H), 7.80 (q, J=9 Hz and 2 Hz, 1H), 8.03 (d, J=2 Hz, 1H).

Compound 2L': $^1$H NMR (CDCl$_3$), δ 0.84 (s, 3H), 1.09 (s, 3H), 1.17 (s, 3H), 1.28 (m, 3H), 1.51 (m, 2H), 1.61 (s, 1H), 1.70 (m, 2H), 1.81 (t, J=2 Hz, 1H), 2.67 (t, J=6 Hz, 2H), 3.08 (t, J=5 Hz, 4H), 3.55 (q, J=6 Hz, 2H), 3.72 (m, 6H), 3.81 (dd, J=9 Hz and 2 Hz, 1H), 5.94 (d, J=9 Hz, 1H), 6.80 (m, 2H), 7.82 (dd, J=9 Hz and 2 Hz, 1H), 8.04 (d, J=2 Hz, 1H).

EXAMPLE 2M

Preparation of 4-(2-methoxyethylamino)-3-(pyrrolidin-1-ylsulfonyl)-N-((1S,4R)-1,3,3-trimethylbicyclo[2.2.1]heptan-2-yl)benzamide (2M)

Compound 2M was prepared from 4-bromo-3-chlorosulfonyl-benzoic acid (2.2) through reaction with amine Ai, amide formation with amine Ba, yielding compound 2.4.AiBa, followed by reaction with amine Cc, according to procedures described in Example 2A.

Compound 2M: $^1$H NMR (CDCl$_3$), δ 0.84 (s, 3H), 1.09 (s, 3H), 1.17 (s, 3H), 1.26 (m, 4H), 1.51 (m, 2H), 1.71 (m, 2H), 1.82 (m, 6H), 3.29 (m, 5H), 3.38 (m, 6H), 3.63 (t, J=5 Hz, 3H), 3.81 (dd, J=9 Hz and 2 Hz, 1H), 5.95 (d, J=9 Hz, 1H), 6.75 (d, J=9 Hz, 1H), 6.84 (t, J=5 Hz, 1H), 7.83 (dd, J=9 Hz and 2 Hz, 1H), 8.06 (d, J=2 Hz, 1H).

EXAMPLE 2N

Preparation of 4-(benzylamino)-3-(pyrrolidin-1-ylsulfonyl)-N-((1S,4R)-1,3,3-trimethylbicyclo[2.2.1]heptan-2-yl)benzamide (2N)

Compound 2N was prepared from 4-bromo-3-(pyrrolidin-1-ylsulfonyl)-N-((1S,4R)-1,3,3-trimethylbicyclo[2.2.1]heptan-2-yl)benzamide 2.4.AiBa and benzylamine Ck following method 2c.

Compound 2N: $^1$H NMR (CDCl$_3$), δ 0.82 (s, 3H), 1.08 (s, 3H), 1.16 (s, 3H), 1.25 (m, 3H), 1.59 (s, 3H), 1.69 (m, 3H), 1.79 (t, J=2 Hz, 1H), 1.85 (m, 4H), 3.30 (m, 4H), 3.78 (m, 1H), 4.46 (d, J=6 Hz, 1H), 5.92 (m, 1H), 6.71 (d, J=9 Hz, 1H), 7.16 (m, 1H), 7.32 (m, 7H), 7.73 (m, 1H), 8.09 (d, J=2 Hz, 1H).

EXAMPLE 2O

Preparation of 3-(N,N-dimethylsulfamoyl)-4-(2-methoxyethylamino)-N-((1S,4R)-1,3,3-trimethylbicyclo[2.2.1]heptan-2-yl)benzamide (2O)

Compound 2O was prepared from 4-bromo-3-chlorosulfonyl-benzoic acid (2.2) through reaction with amine Af, amide formation with amine Ba, yielding compound 2.4.AfBa, according to procedures described in Example 2A, followed by reaction with amine Cc, according to Method 2c.

Compound 2O: $^1$H NMR (CDCl$_3$), δ 0.84 (s, 3H), 1.09 (s, 3H), 1.17 (s, 3H), 1.28 (m, 3H), 1.51 (m, 1H), 1.70 (d, J=10 Hz, 2H), 1.80 (t, J=2 Hz, 1H), 2.76 (s, 6H), 3.38 (m, 5H), 3.63 (t, J=5 Hz, 2H), 3.81 (dd, J=9 Hz and 2 Hz, 1H), 5.97 (d, J=9 Hz, 1H), 6.76 (d, J=9 Hz, 1H), 6.84 (s, 1H), 7.82 (dd, J=9 Hz and 2 Hz, 1H), 8.01 (d, J=2 Hz, 1H).

EXAMPLE 2P

Preparation of 3-(N-(2-hydroxyethyl)-N-methylsulfamoyl)-4-(2-methoxyethylamino)-N-((1S,4R)-1,3,3-trimethyl-bicyclo[2.2.1]heptan-2-yl)benzamide (2P)

Compound 2P was prepared from 4-bromo-3-chlorosulfonyl-benzoic acid (2.2) through reaction with amine An, amide formation with amine Ba, yielding compound 2.4.AnBa, according to procedures described in Example 2A, followed by reaction with amine Cc, according to Method 2c.

Compound 2P: $^1$H NMR (CDCl$_3$), δ 0.84 (s, 3H), 1.09 (s, 3H), 1.17 (s, 3H), 1.28 (m, 3H), 1.51 (m, 2H), 1.71 (m, 2H), 1.80 (t, J=2 Hz, 1H), 2.85 (s, 3H), 3.32 (t, J=5 Hz, 2H), 3.41 (m, 5H), 3.66 (t, J=5 Hz, 2H), 3.71 (t, J=5 Hz, 2H), 3.81 (dd, J=9 Hz and 2 Hz, 1H), 5.98 (d, J=9 Hz, 1H), 6.62 (t, J=5 Hz, 1H), 6.76 (d, J=9 Hz, 1H), 7.84 (dd, J=9 Hz and 2 Hz, 1H), 8.11 (d, J=2 Hz, 1H).

EXAMPLE 2Q

Preparation of 4-amino-3-(N-tert-butylsulfamoyl)benzoic acid (2.6.Al)

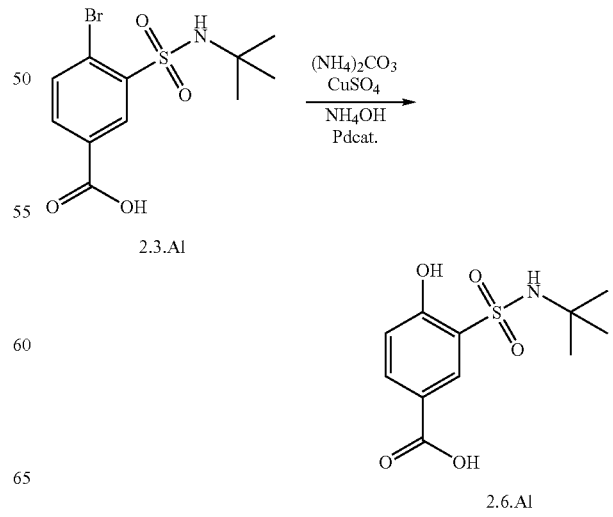

A solution of 4-bromo-3-tert-butylsulfamoyl-benzoic acid (2.3.Al, 1.00 g, 2.97 mmol, obtained from 2.2 and amine Al according to Example 2A), ammonium carbonate (0.857 g, 8.92 mmol) and copper(II) sulfate (47 mg, 0.30 mmol) in ammonium hydroxide (6 mL, 0.1 mol) was heated at 135° C. overnight. LCMS indicated no reaction. Tetrakis(triphenylphosphine)palladium(0) (10 mg, 0.009 mmol) was added and heating continued at 135° C. overnight. The reaction mixture was acidified with 1M HCl and extracted with EtOAc. The organic layer was washed with brine, dried over $Na_2SO_4$, filtered and evaporated to give the product as an orange solid (800 mg, 100% yield). MS analysis (m−1)=271.

Compound 2Q was prepared from 4-amino-3-(N-tert-butylsulfamoyl)benzoic acid (2.6.Al) and amine Ba according to method 1b.

Compound 2Q: $^1$H NMR (CDCl$_3$), δ 0.84 (s, 3H), 1.09 (s, 3H), 1.17 (s, 3H), 1.22 (s, 9H), 1.38 (m, 3H), 1.67 (m, 3H), 1.81 (m, 1H), 3.81 (dd, J=9 Hz and 2 Hz, 1H), 4.62 (m, 1H), 5.97 (m, 1H), 6.77 (dd, J=8 Hz and 3 Hz, 1H), 7.79 (dd, J=9 Hz and 2 Hz, 1H), 8.10 (d, J=2 Hz, 1H), 8.48 (d, J=2 Hz, 1H)

EXAMPLE 2R

Preparation of 3-(N-benzyl-N-methyl-sulfamoyl)-4-(2-(dimethyl-amino)ethylamino)-N-((1S,4R)-1,3,3-trimethyl-bicyclo[2.2.1]heptan-2-yl)-benzamide (2R)

Compound 2R was prepared from 4-bromo-3-(chlorosulfonyl)benzoic acid 2.2 and methyl benzylamine Ao, amide formation with amine Ba, followed by reaction with amine Ca according to the procedures outlined in Example 2A.

Compound 2R: $^1$H NMR (CDCl$_3$), δ 0.84 (s, 3H), 1.09 (s, 3H), 1.17 (s, 3H), 1.28 (m, 2H), 1.34 (m, 1H), 1.51 (m, 1H), 1.73 (m, 2H), 1.81 (t, J=2 Hz, 1H), 2.63 (s, 5H), 2.67 (s, 3H), 2.86 (d, J=5 Hz, 6H), 3.18 (q, J=6 Hz, 2H), 3.65 (m, 1H), 3.77 (m, 1H), 3.81 (dd, J=9 Hz and 1 Hz, 1H), 3.98 (t, J=7 Hz, 2H), 4.25 (s, 2H), 6.06 (d, J=9 Hz, 1H), 7.26 (m, 4H), 7.32 (m, 3H), 7.83 (dd, J=9 Hz and 2 Hz, 1H), 8.20 (d, J=2 Hz, 1H), 12.91 (br s, 1H)

EXAMPLE 4

Preparation of (2R)-7-oxa-bicyclo[2.2.1]heptan-2-amine (4.6)

Scheme 4:

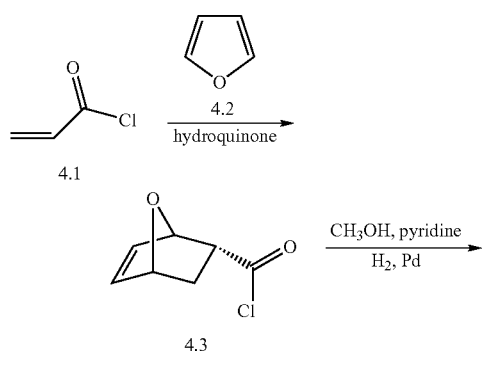

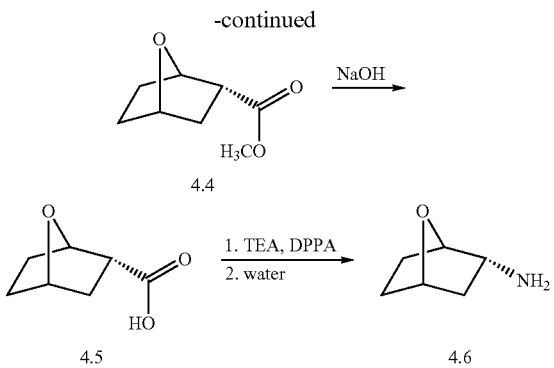

A 20 mL screw top scintillation vial was charged with the hydroquinone (0.20 g, 0.0018 mole), furan (4.2, 3.2 mL, 0.044 mole) and 2-propenoyl chloride (4.1, 2.2 mL, 0.027 mole) and allowed to stir overnight at room temperature. After stirring overnight, the NMR indicated significant amounts of product 4.3 had formed by comparison to published chemical shifts of the methyl ester analog. The reaction was allowed to stir for an additional 22 hours at room temperature and then taken forward to the next step as a crude material.

A 250 mL hydrogenation flask was charged with methanol (20 mL, 0.6 mole) and pyridine (3.2 gram, 0.041 mole). This reaction solution was cooled in an ice water bath and the acid chloride (4.3) formed in the preceding step (4.3 grams, 0.027 mole) was added dropwise over five minutes. After ten minutes the cooling bath was removed, the reaction was aged for 30 minutes, deoxygenated with a nitrogen sweep for five minutes, charged with 0.5 gram of 10% Pd on carbon, and hydrogenated at 50-60 psi overnight. The final reaction mixture was placed under vacuum to remove hydrogen and then filtered through celite to remove catalyst. The methanol was concentrated under vacuum and the concentrate was partitioned between 40 mL of water and a mixture of 30 mL of ethyl acetate and 30 mL of toluene. The organic layer was washed with 20 mL of saturated brine and concentrated under vacuum to yield a solid and a liquid. The solid was removed by trituration with 5 mL of toluene and concentrated under vacuum to yield a yellow oil.

The oil was dissolved in 2 mL of dichloromethane and vacuum chromatographed on silica gel using dichloromethane as the eluent. Baseline material was removed and 1.4 grams of a yellow liquid was isolated. The NMR was consistent with an assigned structure of an endo major product 4.4 in a mixture of endo and exo isomers.

A 20 mL scintillation was charged with 500 mg (0.003 mole) of the methyl ester 4.4 from the preceding step 2 mL of 1.0 N NaOH and 2 mL of ethanol and allowed to stir over the weekend at room temperature. Thin layer chromatography using dichloromethane and potassium permanganate stain indicated the reaction was complete. The ethanol was removed under vacuum and the concentrate was partitioned between 20 mL of ethyl acetate and 15 mL of water. The aqueous phase was made acidic with four mL of 6.0 N HCl and then extracted with two 25 mL portions of ethyl acetate. These organic extracts were combined and concentrated under vacuum. Then 10 mL of acetonitrile was added and removed under vacuum to yield 260 mg of a dark brown liquid. The NMR was consistent with the assigned structure 4.5. $^1$H NMR (400 MHz, CD$_3$CN) δ 4.70 (m, 1H), 2.70 (m, 3H), 1.5 (m, 5H).

A 50 mL RB single-necked flask was charged with acid 4.5 (1.0 gram, 0.0069 mole), 10 mL of toluene and triethylamine (0.73 g, 0.0072 mole). After 20 minutes stirring at room temperature, diphenylphosphonic azide (2.00 g, 0.0073 mole) was added dropwise over 10 minutes to the ice bath cooled reaction. After ten minutes of additional stirring the cooling bath was removed and the reaction was allowed to stir for one hour at room temperature. Then water (0.30 gram, 0.017 mole) was added and the reaction was heated to 70° C. overnight. After cooling to room temperature, an additional 5 mL of water was added and the organic phase was concentrated under vacuum to yield the crude amine 4.6, which was reacted without purification. $^1$H NMR (400 MHz, CD$_3$CN) δ 4.30 (m, 1H), 4.1 (m, 1H), 3.8 (m, 1H), 2.20 (m, 1H), 1.7 (m, 5H).

EXAMPLE 5

Preparation of (2R)-1,4-dimethyl-7-oxa-bicyclo [2.2.1]heptan-2-amine (5.6)

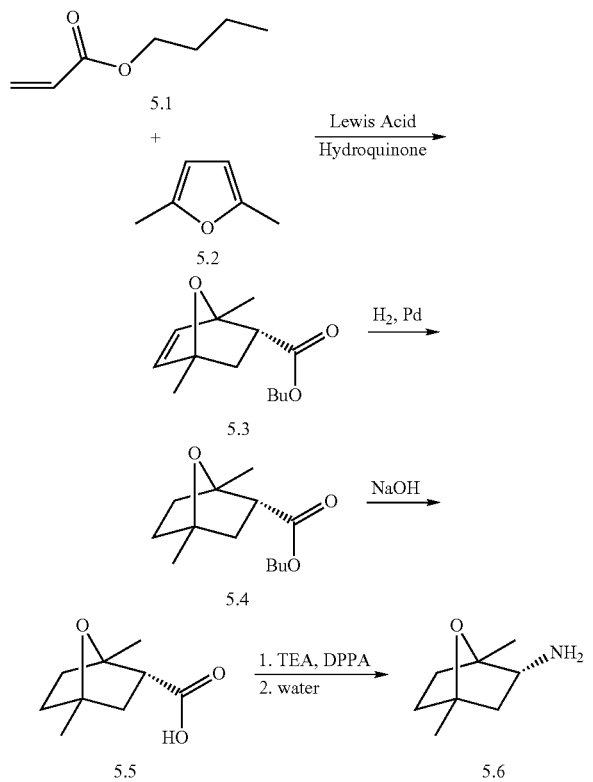

A 20 mL screw top scintillation vial was charged with hydroquinone (0.23 g, 0.0021 mole), 2,5-dimethyl furan (5.2, 5.0 mL 0.047 mole) and n-butyl acrylate (5.1, 4.2 mL, 0.029 mole) and allowed to stir at room temperature. After stirring for six weeks at room temperature NMR indicated some reaction had occurred. A reaction aliquot was concentrated under vacuum and indicated methyl signals at 1.4 ppm, which could not be 2,5-dimethylfuran. Since these product molecules are known to be prone to retro Diels-Alder upon heating it was decided to carry the crude reaction forward to the next step, the hydrogenation without workup or attempted purification.

A 250 mL hydrogenation flask was charged with 6.5 grams (0.029 mole) of the Diels Alder product 5.3 from the first step and 40 mL of methanol. After the solution was deoxygenated with nitrogen for 20 minutes, 1 gram of 10% Pd on carbon was added and the reaction was put through three hydrogen/vacuum cycles on a Parr hydrogenator. The reaction was shaken for six hours at 35-45 psi. Initial hydrogen uptake was very rapid. The reaction was purged with nitrogen and the catalyst removed by filtration thru Celite. The solution was concentrated under vacuum and dissolved in 30 mL of toluene (homogenous) and concentrated under vacuum. Yield was 1.84 grams of a yellow liquid. The NMR was consistent with the desired product 5.4 as the major product.

The reactor was charged with 1.8 grams of the butyl ester 5.4 (from the preceding step), 5 mL of ethanol, 4 mL of 1.0 N NaOH solution and 624 mg of solid NaOH pellets. The reaction was allowed to stir overnight at room temp. The reaction turned dark brown. The next day ethanol was removed under vacuum and the concentrate was partitioned between 20 mL of ethyl acetate and 15 mL of water. The aqueous phase was made strongly acidic with 5 mL of 6.0 N HCL and extracted with two 25 mL portions of ethyl acetate. The combined organic extracts were concentrated under vacuum and azeotropically dried with ethyl acetate that was removed under vacuum to yield a brown solid 5.5. LCMS indicated correct mass and NMR consistent with assigned structure. Suspect mostly endo isomer. Yield 1.22 grams. $^1$H NMR (400 MHz, CD$_3$CN) δ 2.4 (m, 1H), 1.6 (m, 4H), 1.4 (s, 3H), 1.3 (s, 3H).

Carboxylic acid 5.5 is then reacted with amine 5.6 via the procedure described for the preparation of 4.6.

EXAMPLE 6

Preparation of (6R)-3-oxa-bicyclo[3.2.1]octan-6-amine (6.5)

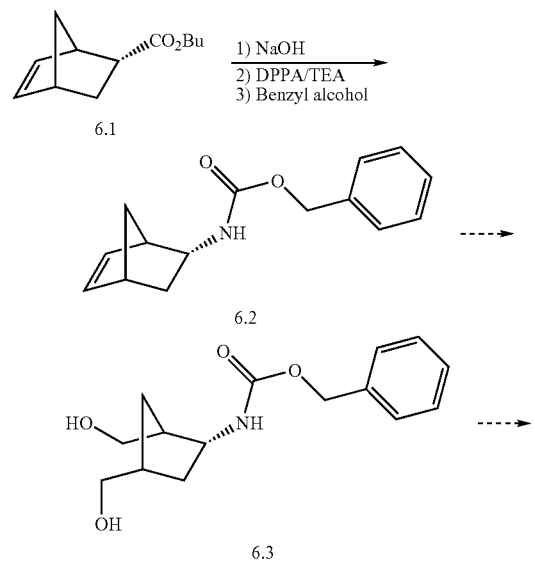

-continued

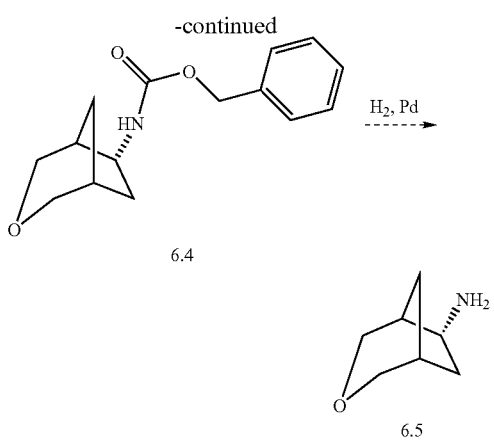

(2R)-Butyl bicyclo[2.2.1]hept-5-ene-2-carboxylate 6.1 is commercially available from Aldrich and is converted to the amine following procedures described previously. The reaction is quenched with benzyl alcohol, yielding carbamate 6.2. Oxidative cleavage of the double bond to 6.3 is accomplished via ozonolysis (Flippin, L. A. et al., *Journal of Organic Chemistry*, 1989, 54(6), 1430-2). The cyclic ether 6.4 is prepared via cyclodehydration over $AlPO_4$—$Al_2O_3$ (Costa, A. et al., *Synthetic Communications*, 1987, 17(11), 1373-1376) or with superacidic perfluorinated resinsulfonic acid Nafion-H catalyst (Olah, G. A., *Synthesis* 1981, 474-476). Hydrogenation yields the free amine 6.5.

Biological Assays:

In Vitro Methods $K_i$ values in receptor binding experiments were determined by Cheng-Prusoff correction of $IC_{50}$ values derived from automated nonlinear regression analysis of sigmoidal titration curves using a three-parameter modification (slope set to 1.0) of the four-parameter equation described in Cheng, Y.-C. and W. H. Prusoff, *Biochem. Pharmacol.* 22:3099-3108 (1973) and DeLean et al., *Am. J. Physiol.* 235:E97-E102 (1978).

$EC_{50}$ values in functional assays were also derived from automated nonlinear regression analysis of sigmoidal titration curves using the three-parameter modification of the four-parameter equation.

Preparation of Membranes for hCB1 and hCB2 Receptor Binding and Receptor-mediated Stimulation of [$^{35}$S]GTPγS Binding Chinese hamster ovary cells (CHO-K1), stably transfected with either hCB1 or hCB2, were washed two times with cold PBS, scraped from 500 $cm^2$ tissue culture plates, and pelleted by centrifugation at 1000×g for 10 min. The supernatant was discarded and the pellet was resuspended in Tris assay buffer (50 mM Tris HCl, pH 7.8, containing 1.0 mM EGTA, 5.0 mM $MgCl_2$, 10 mg/mL leupeptin, 10 mg/mL pepstatin A, 200 mg/mL bacitracin, and 0.5 mg/mL aprotinin), homogenized with a Polytron homogenizer (Brinkmann) at a setting of 1 for 20 sec and centrifuged at 38,000×g for 20 min at 4° C. The pellet was resuspended in Tris assay buffer and aliquots of 1 mg protein/mL were stored at −80° C. for further use.

Preparation of Rat Cerebellar Membranes for Cannabinoid Receptor-Mediated Stimulation of [$^{35}$S]GTPγS Binding Rat cerebella were excised and placed into homogenization buffer (50 mM Tris HCl, pH 7.4, containing 3 mM $MgCl_2$ and 1 mM EGTA) and homogenized for 20 sec using a Polytron homogenizer at a setting of 1 and centrifuged at 4° C. for 10 min at 48,000×g. The supernatant was removed and the pellet was resuspended in homogenization buffer and centrifuged at 4° C. for 10 min at 48,000×g. The supernatant was removed and the pellets were resuspended in 50 mM Tris HCl, pH 7.4, containing 3 mM $MgCl_2$ and 0.2 mM EGTA and stored as aliquots of 1 mg protein/mL at −80° C. for further use.

Inhibition of CB Receptor Binding by Test Compounds

Binding assays were performed by incubating 0.2-0.6 nM (34,000-100,000 dpm) [$^3$H]CP55940 with membranes prepared from cells expressing cloned human CB1 or CB2 receptors in buffer A (50 mM Tris HCl, pH 7.0, 5.0 mM $MgCl_2$, 1.0 mM EGTA and 1.0 mg/mL fatty acid free bovine serum albumin). After incubation for 60 min at room temperature for the hCB2 binding assay or 120 min at 30° C. for the hCB1 assay, the assays were filtered through GF/C filters that had been pre-soaked overnight in 0.5% (w/v) PEI and 0.1% BSA in water. The filters were rinsed 6 times with one mL of cold wash buffer (50 mM Tris HCl, pH 7.0, 5.0 mM $MgCl_2$, 1.0 mM EGTA and 0.75 mg/mL fatty acid free bovine serum albumin), 30 μL of MicroScint 20 was added to each filter and the radioactivity on the filters determined by scintillation spectroscopy. Nonspecific binding was determined in the presence of 10 μM WIN55212-2.

Cannabinoid receptor-mediated stimulation of [$^{35}$S]GTPγS binding hCB1-Mediated stimulation of [$^{35}$S]GTPγS binding was measured in a mixture containing 100-150 pM [$^{35}$S]GTPγS, 150 mM NaCl, 45 mM $MgCl_2$, 3 mM GDP, 0.4 mM DTT, 1 mM EGTA, 1 mg/mL fatty acid free BSA, 25 μg of membrane protein and agonist in a total volume of 250 μL of buffer A in 96 well Basic Flashplates (Perkin Elmer). After incubation at room temperature for 2 hours the plates were centrifuged at 800×g at 4° C. for 5 min and the radioactivity bound to the membranes was determined by scintillation spectrometry using the Topcount (Perkin Elmer).

hCB2-Mediated [35 S]GTPγS binding was measured in the same way except the assay mixture contained 10 mM GDP and the incubation time was 6 hours. [$^{35}$S]GTPγS binding in rat cerebellar homogenate was determined in a mixture containing 40-60 pM [$^{35}$S]GTPγS, homogenate assay buffer (50 mM Tris-HCl, 3 mM $MgCl_2$, 0.2 mM EGTA), 100 mM NaCl, 10 mM $MgCl_2$, 100 mM GDP, 20 μg homogenate protein/well and agonist in a total volume of 250 μL in 96 well Basic Flashplates (Perkin Elmer). After incubation at 30° C. for 2 hours, the plates were centrifuged at 800×g at 4° C. for 5 min and the radioactivity bound to the membrane was determined by scintillation spectrometry using the Topcount (Perkin Elmer).

In Vitro Results

Compounds 1A-2R and 2I'-2L', listed in Table 1, were tested for their affinity toward the human cloned CB1 and CB2 receptors. All ligands tested bound to the human CB1 and/or CB2 receptor with affinity ranging from 0.1-10000 nM. These ligands displayed various degrees of selectivity, CB2 vs. CB1. The functional potency of selected ligands was also evaluated in vitro. Some compounds were found to exhibit agonist activity at CB1 and/or CB2 receptors. For example, compound 1X ($K_i$(CB1)=1930 nM, $K_i$(CB2)=8.9 nM) was found to possess no in vitro CB1 receptor agonist activity but good in vitro CB2 receptor agonist potency ($EC_{50}$=18.6 nM). Some compounds were also found to exhibit antagonist activity towards the CB2 receptor. Compound 2D ($K_i$(CB1)=1309 nM, $K_i$(CB2)=1.6 nM) was found to possess potent in vitro CB2 receptor antagonist potency ($IC_{50}$=8.5 nM).

TABLE 1

List of compounds

| # | Name | Structure | M + 1 |
|---|------|-----------|-------|
| 1A | 4-(methylamino)-3-(morph-olinosulfonyl)-N-((1S,4R)-1,3,3-trimethylbicyclo[2.2.1]heptan-2-yl)benzamide | 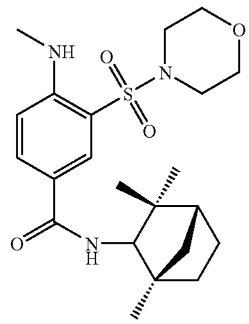 | 436.6 |
| 1B | N-((1R,2R,4S)-bicyclo-[2.2.1]heptan-2-yl)-4-(methylamino)-3-(morpholinosulfonyl)benzamide | 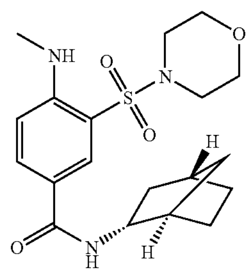 | 394.5 |
| 1C | N-(6-methoxy-1,1-dimethyl-1,2,3,4-tetrahydronaphthalen-2-yl)-4-(methylamino)-3-(morpholinesulfonyl)benzamide | 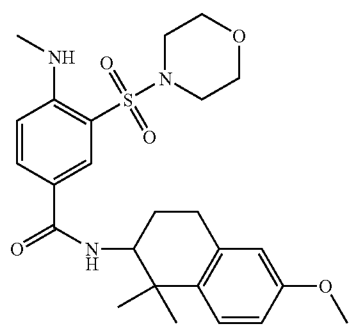 | 488.6 |
| 1D | N-(5-methyl-3-phenyl-isoxazol-4-yl)-4-(methylamino)-3-(morpholinosulfonyl)benzamide | 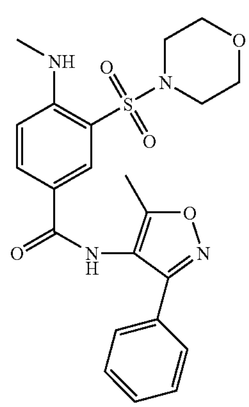 | 457.5 |

TABLE 1-continued

List of compounds

| # | Name | Structure | M + 1 |
|---|------|-----------|-------|
| 1E | 3-(isoindolin-2-ylsulfonyl)-4-(methylamino)-N-((1S,4R)-1,3,3-trimethyl-bicyclo[2.2.1]heptan-2-yl)-benzamide | 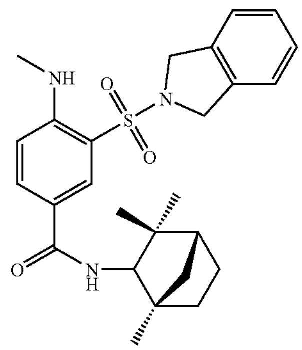 | 468.6 |
| 1F | N-((1R,2R,4S)-bicyclo[2.2.1]heptan-2-yl)-3-(isoindolin-2-ylsulfonyl)-4-(methylamino)benzamide | 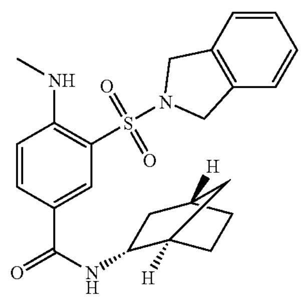 | 426.6 |
| 1G | N-((1R,2S,4R)-7,7-dimethylbicyclo[2.2.1]heptan-2-yl)-3-(isoindolin-2-ylsulfonyl)-4-(methyl-amino)benzamide | 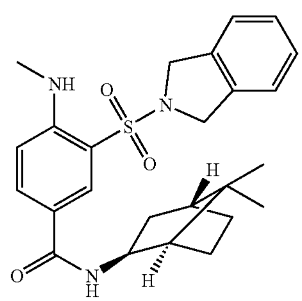 | 468.6 |
| 1H | 3-(1,3-Dihydro-isoindole-2-sulfonyl)-N-[1-(3-hydroxy-adamantan-1-yl)-ethyl]-4-methylamino-benzamide | 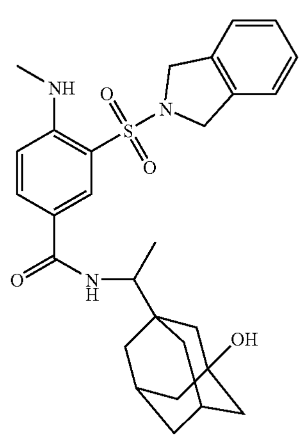 | 510.7 |

TABLE 1-continued

List of compounds

| # | Name | Structure | M + 1 |
|---|------|-----------|-------|
| 1I | 3-(isoindolin-2-ylsulfonyl)-4-(methylamino)-N-neopentylbenzamide | 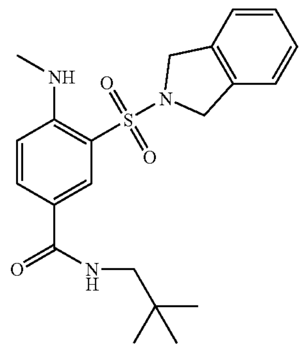 | 402.5 |
| 1J | 3-(isoindolin-2-ylsulfonyl)-4-(methylamino)-N-(1-phenylethyl)benzamide | 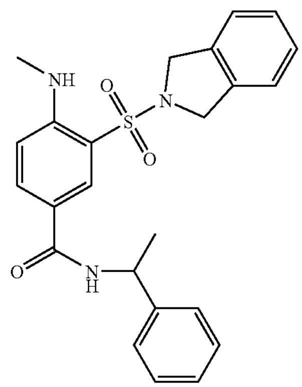 | 436.5 |
| 1K | 3-(isoindolin-2-ylsulfonyl)-4-(methylamino)-N-((1-phenylcyclopentyl)methyl)-benzamide | 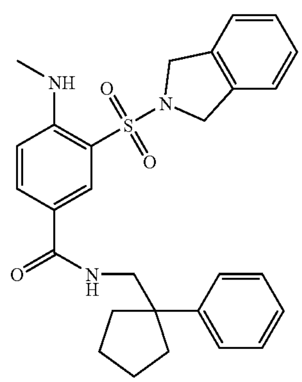 | 490.6 |
| 1L | N-(1-ethylpiperidin-3-yl)-3-(isoindolin-2-ylsulfonyl)-4-(methylamino)benzamide | 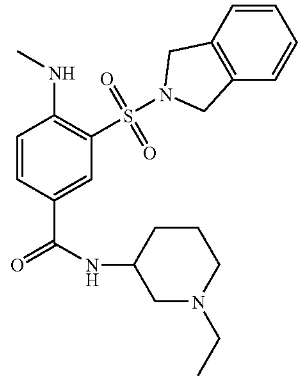 | 443.6 |

TABLE 1-continued

List of compounds

| # | Name | Structure | M + 1 |
|---|------|-----------|-------|
| 1M | 3-(isoindolin-2-ylsulfonyl)-4-(methylamino)-N-(1-morpholinobutan-2-yl)-benzamide | 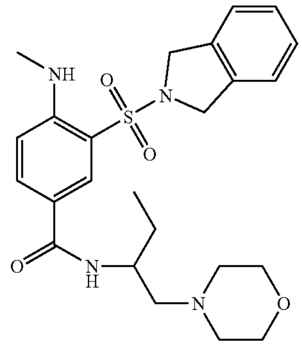 | 473.6 |
| 1N | 3-(N-(2-methoxyethyl)-N-methylsulfamoyl)-4-(methylamino)-N-((1S,4R)-1,3,3-trimethylbicyclo-[2.2.1]heptan-2-yl)benzamide | 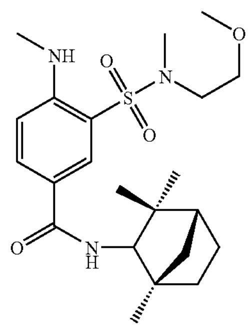 | 438.6 |
| 1O | methyl 2-(N-methyl-2-(methylamino)-5-((1S,4R)-1,3,3-trimethylbicyclo-[2.2.1]heptan-2-ylcarbamoyl)phenylsulfonamido)-acetate | 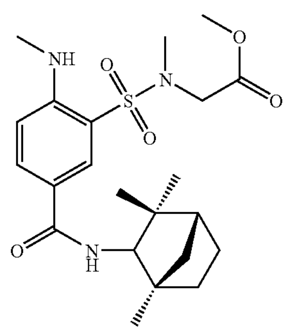 | 452.6 |
| 1P | methyl 2-(5-((1R,2R,4S)-bicyclo[2.2.1]heptan-2-ylcarbamoyl)-N-methyl-2-(methylamino)phenylsulfonamido)acetate | 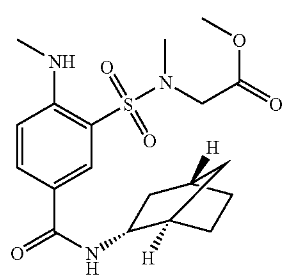 | 410.5 |
| 1Q | methyl 2-(5-((1R,2S,4R)-7,7-dimethylbicyclo-[2.2.1]heptan-2-ylcarbamoyl)-N-methyl-2-(methylamino)phenylsulfonamido)-acetate | 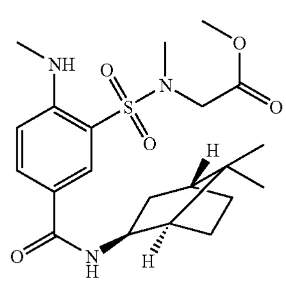 | 452.6 |

TABLE 1-continued

List of compounds

| # | Name | Structure | M + 1 |
|---|------|-----------|-------|
| 1R | ({5-[1-(3-Hydroxy-adamantan-1-yl)-ethyl-carbamoyl]-2-methylaminobenzenesulfonyl}-methyl-amino)-acetic acid methyl ester | 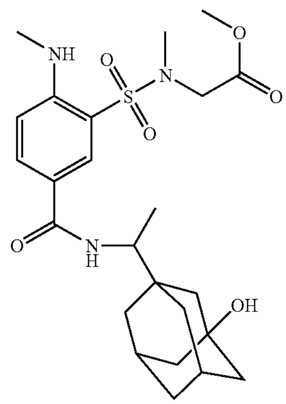 | 494.6 |
| 1S | methyl 2-(N-methyl-2-(methylamino)-5-(neopentylcarbamoyl)phenylsulfonamido)acetate | 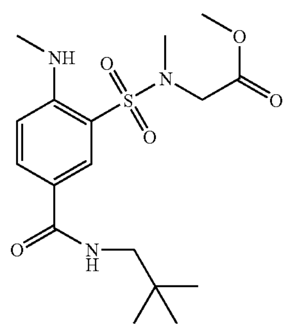 | 386.5 |
| 1T | methyl 2-(N-methyl-2-(methylamino)-5-(1-phenylethylcarbamoyl)phenylsulfonamido)acetate | 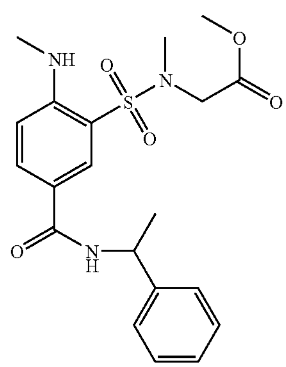 | 420.5 |
| 1U | methyl 2-(N-methyl-2-(methylamino)-5-((1-phenylcyclopentyl)methylcarbamoyl)phenylsulfonamido)acetate | 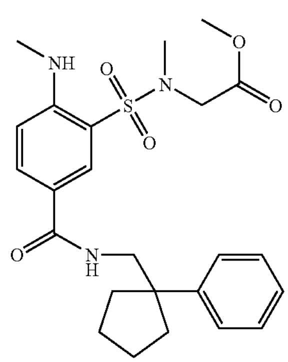 | 474.6 |

TABLE 1-continued

List of compounds

| # | Name | Structure | M + 1 |
|---|------|-----------|-------|
| 1V | methyl 2-(N-methyl-5-(8-methyl-8-aza-bicyclo-[3.2.1]octan-3-ylcarbamoyl)-2-(methylamino)-phenylsulfonamido)acetate | 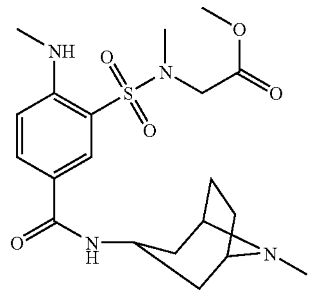 | 439.5 |
| 1W | 3-(azetidin-1-ylsulfonyl)-4-(methylamino)-N-((1S,4R)-1,3,3-trimethylbicyclo-[2.2.1]heptan-2-yl)benzamide | 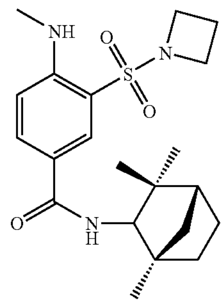 | 406.6 |
| 1X | 3-(N,N-dimethylsulfamoyl)-4-(methylamino)-N-((1S,4R)-1,3,3-trimethylbicyclo[2.2.1]heptan-2-yl)benzamide | 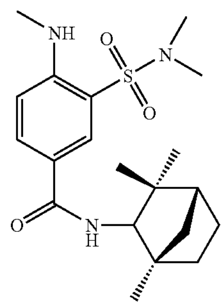 | 394.2 |
| 1Y | N-((1R,2R,4S)-bicyclo-[2.2.1]heptan-2-yl)-3-(N,N-dimethylsulfamoyl)-4-(methylamino)benzamide | 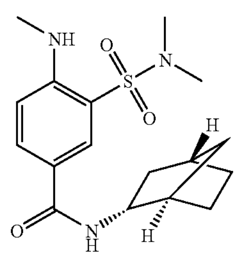 | 352.2 |
| 1Z | 3-(4-hydroxypiperidin-1-ylsulfonyl)-4-(methylamino)-N-((1S,4R)-1,3,3-trimethylbicyclo[2.2.1]heptan-2-yl)benzamide | 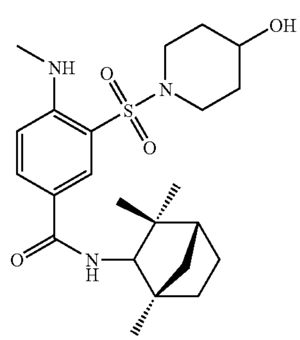 | 450.2 |

TABLE 1-continued

List of compounds

| # | Name | Structure | M + 1 |
|---|------|-----------|-------|
| 1AA | 3-(3-hydroxypiperidin-1-ylsulfonyl)-4-(methyl-amino)-N-((1S,4R)-1,3,3-trimethylbicyclo[2.2.1]heptan-2-yl)benzamide | 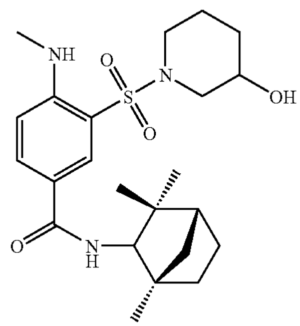 | 450.2 |
| 1AB | 4-(methylamino)-3-(pyrrolidin-1-ylsulfonyl)-N-((1S,4R)-1,3,3-trimethyl-bicyclo[2.2.1]heptan-2-yl)benzamide | 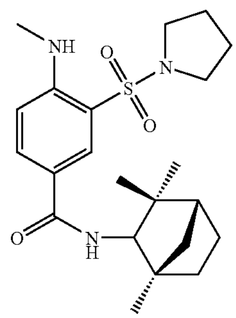 | 420.2 |
| 1AC | N-((1R,2R,4S)-bicyclo-[2.2.1]heptan-2-yl)-4-(methylamino)-3-(pyrrolidin-1-ylsulfonyl)-benzamide | 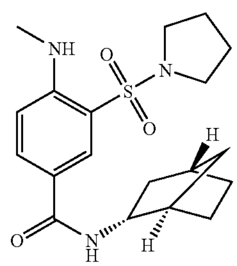 | 378.2 |
| 1AD | N-(3,3-dimethylbutan-2-yl)-4-(methylamino)-3-(pyrrolidin-1-ylsulfonyl)-benzamide | 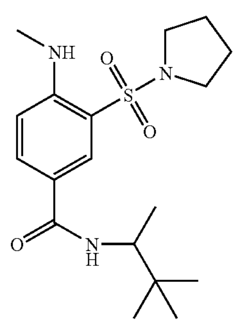 | 368.2 |
| 1AE | 4-(methylamino)-3-(pyrrolidin-1-ylsulfonyl)-N-(3,3,5-trimethylcyclohexyl)-benzamide | 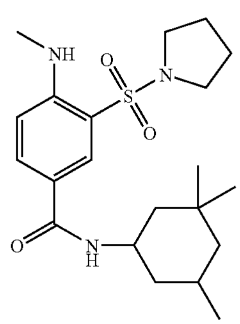 | 407.2 |

TABLE 1-continued

List of compounds

| # | Name | Structure | M + 1 |
|---|---|---|---|
| 1AF | 3-((R)-3-hydroxypyrrolidin-1-ylsulfonyl)-4-(methylamino)-N-((1S,4R)-1,3,3-trimethylbicyclo[2.2.1]heptan-2-yl)benzamide | 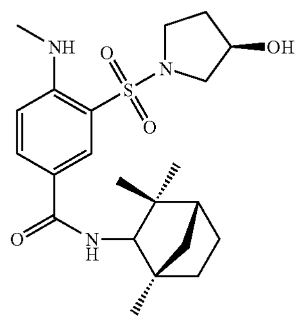 | 436.2 |
| 1AG | 3-((S)-3-hydroxypyrrolidin-1-ylsulfonyl)-4-(methylamino)-N-((1S,4R)-1,3,3-trimethylbicyclo[2.2.1]heptan-2-yl)benzamide | 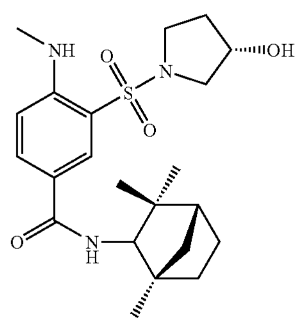 | 436.2 |
| 1AH | N-Adamantan-1-yl-4-methylamino-3-(morpholine-4-sulfonyl)-benzamide | 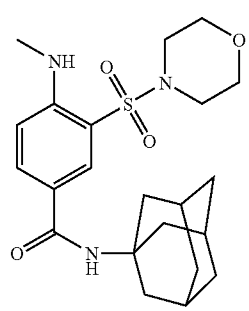 | 434.2 |
| 1AI | 3-(N-tert-butylsulfamoyl)-4-(methylamino)-N-((1S,4R)-1,3,3-trimethylbicyclo[2.2.1]heptan-2-yl)benzamide | 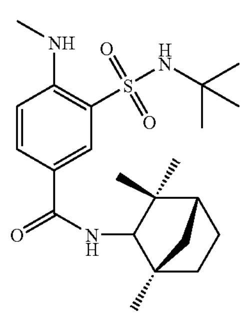 | 422.2 |

TABLE 1-continued

List of compounds

| # | Name | Structure | M + 1 |
|---|------|-----------|-------|
| 1AJ | 3-(N-ethyl-N-methyl-sulfamoyl)-4-(methyl-amino)-N-((1S,4R)-1,3,3-trimethylbicyclo[2.2.1]hep-tan-2-yl)benzamide | 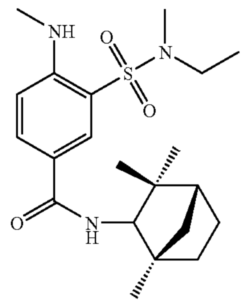 | 408.2 |
| 2A | 4-(2-(dimethylamino)-ethylamino)-3-(morpho-linosulfonyl)-N-((1S,4R)-1,3,3-trimethylbicyclo-[2.2.1]heptan-2-yl)benz-amide | 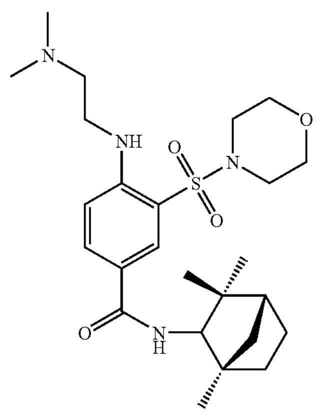 | 493.7 |
| 2B | 4-(2-aminoethylamino)-3-(morpholinosulfonyl)-N-((1S,4R)-1,3,3-trimethyl-bicyclo[2.2.1]heptan-2-yl)benzamide | 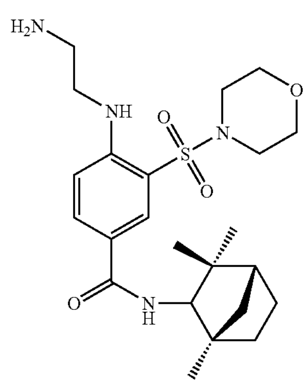 | 465.6 |
| 2C | 4-morpholino-3-(morpho-linosulfonyl)-N-((1S,4R)-1,3,3-trimethylbicyclo-[2.2.1]heptan-2-yl)benz-amide | 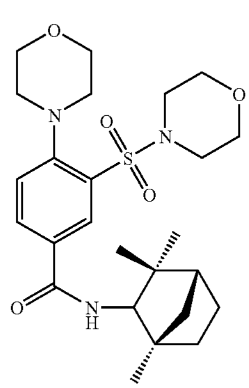 | 492.7 |

TABLE 1-continued

List of compounds

| # | Name | Structure | M + 1 |
|---|---|---|---|
| 2D | 4-(2-methoxyethylamino)-3-(morpholinosulfonyl)-N-((1S,4R)-1,3,3-trimethylbicyclo[2.2.1]heptan-2-yl)benzamide | 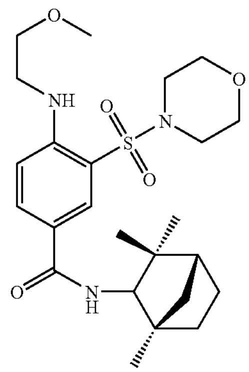 | 480.6 |
| 2E | 4-(dimethylamino)-3-(morpholinosulfonyl)-N-((1S,4R)-1,3,3-trimethylbicyclo[2.2.1]heptan-2-yl)-benzamide | 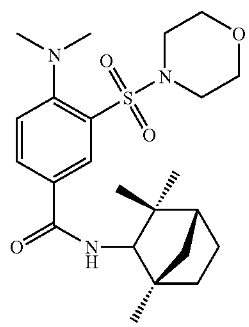 | 450.6 |
| 2F | 4-(ethylamino)-3-(morpholinosulfonyl)-N-((1S,4R)-1,3,3-trimethylbicyclo[2.2.1]heptan-2-yl)benzamide | 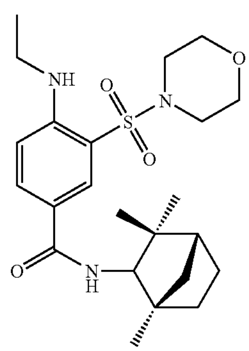 | 450.6 |
| 2G | 4-(isopropylamino)-3-(morpholinosulfonyl)-N-((1S,4R)-1,3,3-trimethylbicyclo[2.2.1]heptan-2-yl)benzamide | 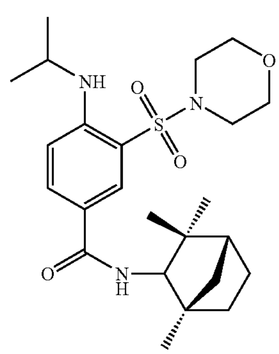 | 464.6 |

TABLE 1-continued

List of compounds

| # | Name | Structure | M + 1 |
|---|------|-----------|-------|
| 2H | 4-amino-3-(morpholine-sulfonyl)-N-((1S,4R)-1,3,3-trimethylbicyclo[2.2.1]heptan-2-yl)benzamide | 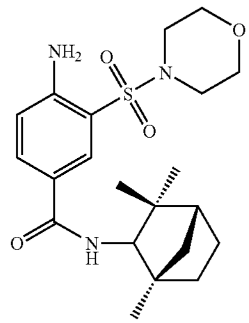 | 422.6 |
| 2I | 4-(benzyloxy)-3-(morpholinosulfonyl)-N-((1S,4R)-1,3,3-trimethylbicyclo[2.2.1]heptan-2-yl)benzamide | 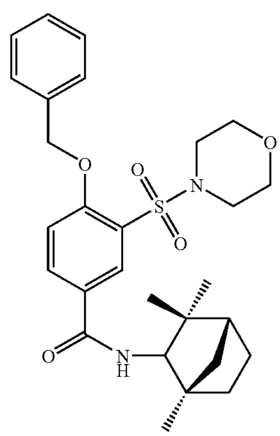 | 513.7 |
| 2J | 4-hydroxy-3-(morpholinosulfonyl)-N-((1S,4R)-1,3,3-trimethylbicyclo[2.2.1]heptan-2-yl)benzamide | 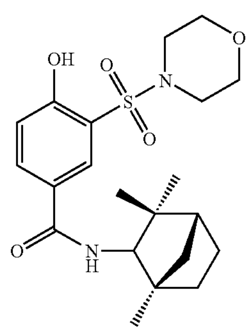 | 423.2 |
| 2K | 4-methoxy-3-(morpholinosulfonyl)-N-((1S,4R)-1,3,3-trimethybicyclo[2.2.1]heptan-2-yl)benzamide | 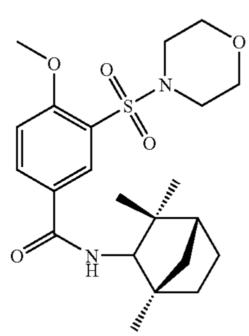 | 437.6 |

TABLE 1-continued

List of compounds

| # | Name | Structure | M + 1 |
|---|------|-----------|-------|
| 2L | 4-(2-methoxyethoxy)-3-(morpholinosulfonyl)-N-((1S,4R)-1,3,3-trimethyl-bicyclo[2.2.1]heptan-2-yl)benzamide | 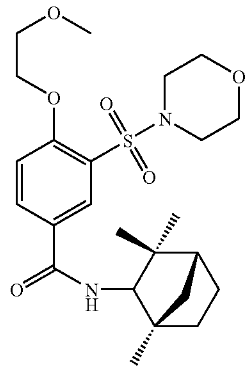 | 481.2 |
| 2I' | 3-(morpholinosulfonyl)-4-(1H-pyrazol-1-yl)-N-((1S,4R)-1,3,3-trimethyl-bicyclo[2.2.1]heptan-2-yl)benzamide | 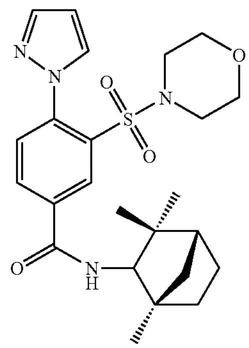 | 473.2 |
| 2J' | 4-((2-methoxyethyl)-(methyl)-amino)-3-(morpholinosulfonyl)-N-((1S,4R)-1,3,3-trimethylbicyclo-[2.2.1]heptan-2-yl)benzamide | 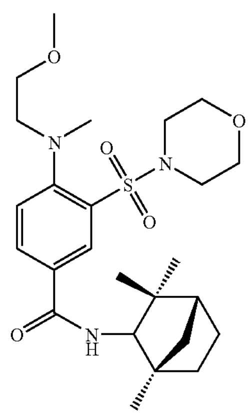 | 494.2 |
| 2K' | 4-((3-methoxypropyl)-amino)-3-morpholinosulfonyl)-N-((1S,4R)-1,3,3-trimethylbicyclo-[2.2.1]heptan-2-yl)benzamide | 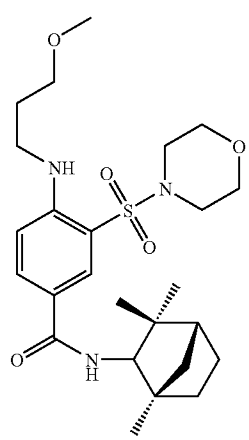 | 508.2 |

TABLE 1-continued

List of compounds

| # | Name | Structure | M + 1 |
|---|------|-----------|-------|
| 2L' | methyl 3-(2-(morpholino-sulfonyl)-4-((1S,4R)-1,3,3-trimethyl-bicyclo[2.2.1]-heptan-2-ylcarbamoyl)-phenyl)amino)propanoate | 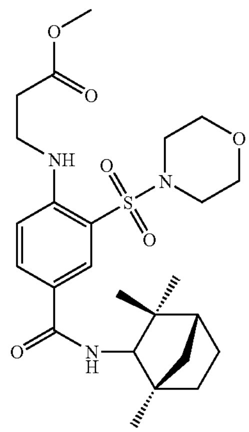 | 522.2 |
| 2M | 4-(2-methoxyethylamino)-3-(pyrrolidin-1-ylsulfonyl)-N-((1S,4R)-1,3,3-trimethyl-bicyclo[2.2.1]heptan-2-yl)benzamide | 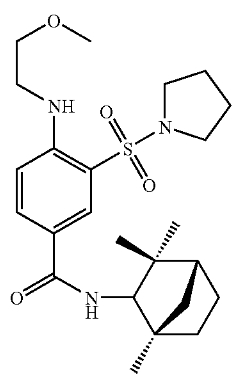 | 464.2 |
| 2N | 4-(benzylamino)-3-(pyrrolidin-1-ylsulfonyl)-N-((1S,4R)-1,3,3-trimethyl-bicyclo[2.2.1]heptan-2-yl)benzamide | 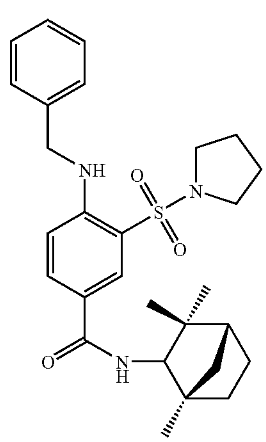 | 496.2 |

TABLE 1-continued

List of compounds

| # | Name | Structure | M + 1 |
|---|---|---|---|
| 2O | 3-(N,N-dimethylsulfamoyl)-4-(2-methoxyethylamino)-N-((1S,4R)-1,3,3-trimethyl-bicyclo[2.2.1]heptan-2-yl)benzamide | 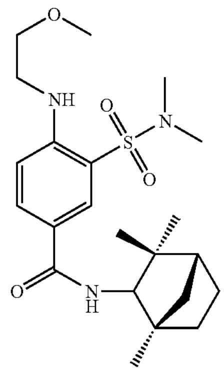 | 438.2 |
| 2P | 3-(N-(2-hydroxyethyl)-N-methylsulfamoyl)-4-(2-methoxyethylamino)-N-((1S,4R)-1,3,3-trimethyl-bicyclo[2.2.1]heptan-2-yl)benzamide | 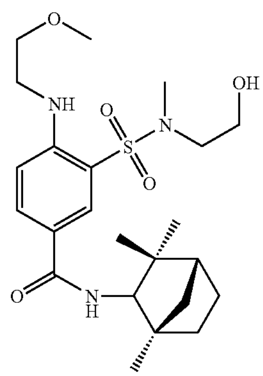 | 468.2 |
| 2Q | 4-amino-3-(N-tert-butyl-sulfamoyl)-N-((1S,4R)-1,3,3-trimethylbicyclo[2.2.1]heptan-2-yl)benzamide | 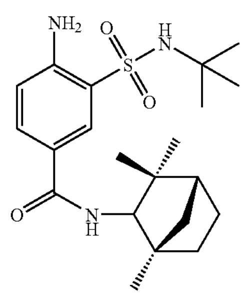 | 408.2 |
| 2R | 3-(N-benzyl-N-methyl-sulfamoyl)-4-(2-(dimethylamino)ethylamino)-N-((1S,4R)-1,3,3-trimethyl-bicyclo[2.2.1]heptan-2-yl)-benzamide | 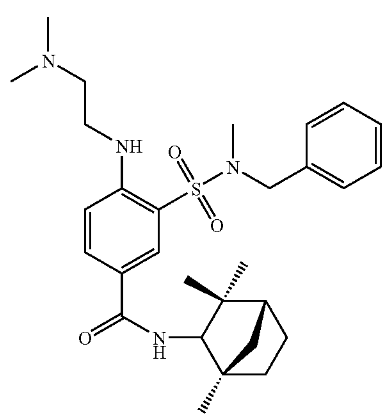 | 527.3 |

What is claimed is:

1. A compound of formula I:

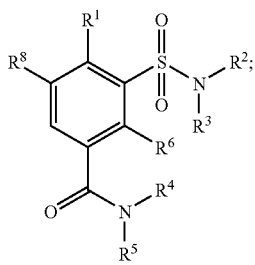

wherein:
R$^1$ is NR$^y$R$^z$;
each R$^x$, R$^y$ and R$^z$ is independently H, alkyl, cycloalkyl, cycloalkylalkyl, aryl, aralkyl, heterocycloalkyl, heterocycloalkylalkyl, heteroaryl, or heteroaralkyl; or R$^y$ and R$^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;

R$^2$ and R$^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of R$^2$ and R$^3$ is other than H; or R$^2$ and R$^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N(R$^9$)—, —N(R$^{10}$)—C(=O)—, or —C(=O)—N(R$^{10}$)—;

R$^4$ is H or alkyl;
R$^5$ is:

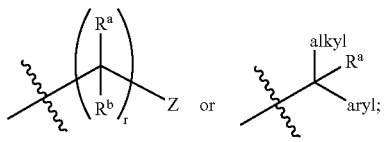

Z is

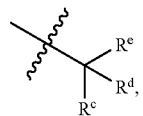

a 1 or 2 heteroatom containing heteroaryl, or a 1 or 2 heteroatom containing heterocycloalkyl, wherein each heteroatom of said heteroaryl or heterocycloalkyl group is independently selected from the group consisting of N, N(R$^{11}$), O, and S;
each R$^a$ and R$^b$ is independently H or alkyl;
R$^c$ is H, alkyl, or aryl;
R$^d$ and R$^e$ are each independently H or alkyl, with the proviso that at least two of R$^c$, R$^d$, and R$^e$ are other than H; or R$^d$ and R$^e$, taken together with the carbon atom to which they are attached, form a carbocyclic or heterocyclic ring; or R$^c$, R$^d$, and R$^e$, taken together with the carbon atom to which they are attached, form a bicycloalkyl, tricycloalkyl, heterobicyclic, or heterotricyclic ring;
R$^6$ and R$^8$ are each independently H or alkyl;
each R$^9$ is independently H, alkyl, aryl, —C(=O)—R$^{11}$, —C(=O)—OR$^{11}$, —[C(R$^{11}$)(R$^{11}$)]$_s$—C(=O)—OR$^{11}$, —SO$_2$R$^{11}$, or —C(=O)N(R$^{11}$)R$^{11}$;
each R$^{10}$ is independently H, alkyl, or aryl;
each R$^{11}$ is independently H or alkyl;
r is 0, 1, 2, or 3; and
s is 1, 2, 3, or 4;
with the provisos that:
(1) when R$^d$ and R$^e$ are each independently H or alkyl, then R$^c$ is H or alkyl;
(2) when R$^c$ is aryl, then R$^d$ and R$^e$, taken together with the carbon atom to which they are attached, form a carbocyclic or heterocyclic ring;
(3) NR$^y$R$^z$ is other than an optionally substituted piperazine ring; and
(4) when R$^4$ is H, R$^5$ is sec-butyl, and R$^6$, R$^8$, and one of R$^2$ and R$^3$ is H, then the other of R$^2$ and R$^3$ is other than;

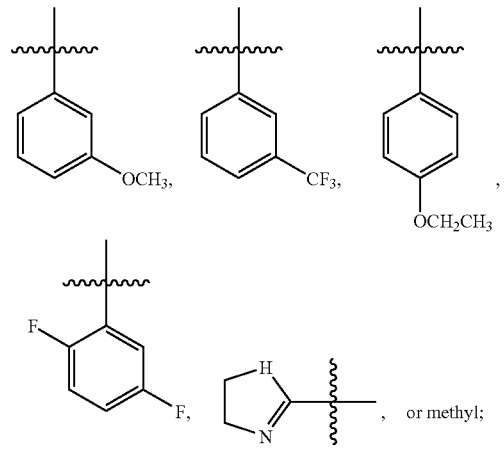

or a pharmaceutically acceptable salt thereof.

2. A compound of claim 1, wherein R$^6$ and R$^8$ are each H.

3. A compound according to claim 2, wherein R$^y$ and R$^z$ are each independently H or alkyl, or R$^y$ and R$^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—.

4. A compound according to claim 3, wherein $R^y$ and $R^z$ are each independently H or $C_1$-$C_3$alkyl.

5. A compound according to claim 2, wherein $R^y$ is H.

6. A compound according to claim 5, wherein $R^z$ is alkyl or aralkyl.

7. A compound according to claim 6, wherein $R^z$ is $C_1$-$C_3$alkyl.

8. A compound according to claim 7, wherein $R^z$ is $C_2$-$C_3$alkyl substituted with ($C_1$-$C_3$alkyl)($C_1$-$C_3$alkyl)amino or $C_1$-$C_3$alkoxy.

9. A compound according to claim 3, wherein $R^y$ and $R^z$, when taken together with the nitrogen atom to which they are attached, form a 4- to 6-membered heterocycloalkyl ring.

10. A compound according to claim 2, wherein $R^4$ is H or alkyl.

11. A compound according to claim 10, wherein $R^4$ is H.

12. A compound according to claim 2, wherein $R^6$ and $R^8$ are each H.

13. A compound according to claim 2, wherein $R^5$ is

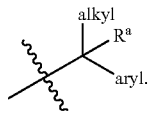

14. A compound according to claim 13, wherein $R^5$ is

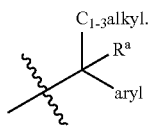

15. A compound according to claim 14, wherein $R^a$ is H.

16. A compound according to claim 15, wherein the aryl of said $R^5$ is phenyl.

17. A compound according to claim 2, wherein $R^5$ is

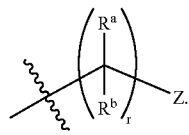

18. A compound according to claim 17, wherein r is 0, 1, or 2.

19. A compound according to claim 18, wherein r is 0.

20. A compound according to claim 17, wherein Z is

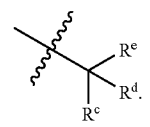

21. A compound according to claim 20, wherein $R^c$ is H or $C_1$-$C_3$alkyl.

22. A compound according to claim 20, wherein $R^c$ is phenyl.

23. A compound according to claim 20, wherein $R^d$ and $R^e$ are each independently H or $C_1$-$C_6$alkyl.

24. A compound according to claim 20, wherein $R^d$ and $R^e$, taken together with the carbon atom to which they are attached, form a monocyclic carbocyclic, bicyclic carbocyclic, monocyclic heterocyclic, or bicyclic heterocyclic ring.

25. A compound according to claim 24, wherein $R^c$ is $C_1$-$C_3$alkyl or phenyl.

26. A compound according to claim 20, wherein $R^d$ and $R^e$, taken together with the carbon atom to which they are attached, form a bicycloalkyl, tricycloalkyl, heterobicyclic, or heterotricyclic ring.

27. A compound according to claim 26, wherein $R^d$ and $R^e$, taken together with the carbon atom to which they are attached, form a bicycloalkyl or tricycloalkyl ring.

28. A compound according to claim 27, wherein the bicycloalkyl ring is substituted with 1-3 alkyl groups.

29. A compound according to claim 20, wherein $R^c$, $R^d$, and $R^e$, taken together with the carbon atom to which they are attached, form a bicycloalkyl, tricycloalkyl, heterobicyclic, or heterotricyclic ring.

30. A compound according to claim 29, wherein $R^c$, $R^d$, and $R^e$, taken together with the carbon atom to which they are attached, form a bicycloalkyl or tricycloalkyl ring.

31. A compound according to claim 30, wherein the bicycloalkyl ring is substituted with 1-3 alkyl groups.

32. A compound according to claim 17, wherein $R^5$ is:

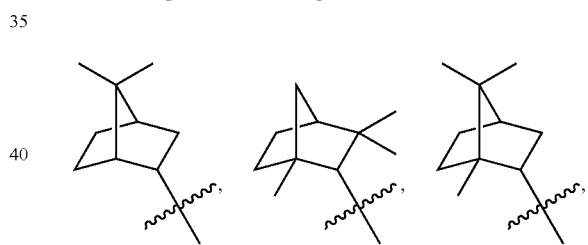

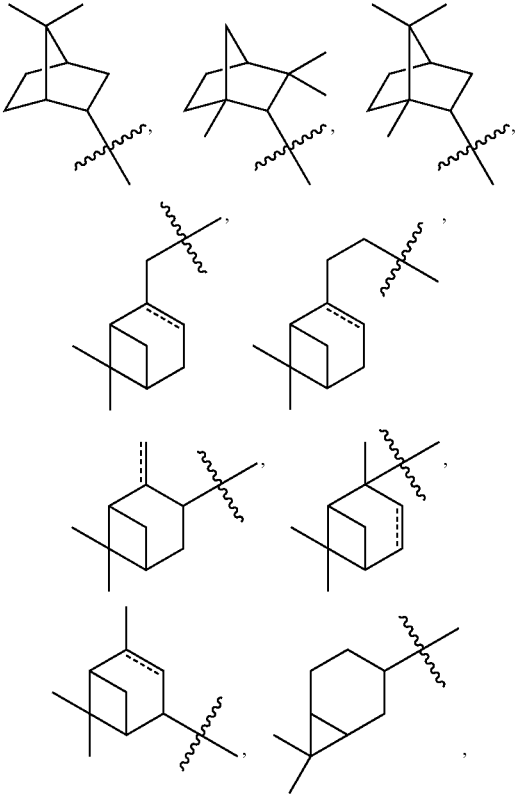

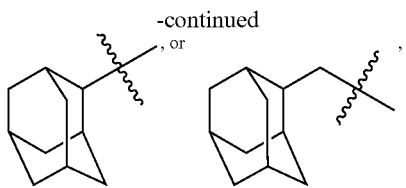

or an enantiomeric or diastereomeric form thereof;
wherein:
= represents a single or double bond between the two bonded carbon atom termini.

33. A compound according to claim 17, wherein $R^5$ is:

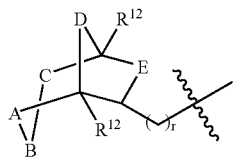

or an enantiomeric or diastereomeric form thereof;
wherein:
A, B, and C are each independently $C(R^{12})(R^{12})$, a bond, or —O—, provided that no more than one of A, B, and C is a bond and provided that no more than one of A, B, and C is —O—;
D and E are each independently $C(R^{12})(R^{12})$ or —O—, provided that at least three of A, B, C, D, and E are other than —O—; and
each $R^{12}$ is independently H or $C_1$-$C_3$alkyl.

34. A compound according to claim 17, wherein Z is a 1 or 2 heteroatom containing $C_5$-$C_6$heteroaryl, or a 1 or 2 heteroatom containing $C_5$-$C_6$heterocycloalkyl, wherein each heteroatom is independently —$N(R^{11})$, O, or S.

35. A compound according to claim 2, wherein each $R^a$ is H.

36. A compound according to claim 2, wherein each $R^b$ is independently H or $C_1$-$C_3$alkyl.

37. A compound according to claim 2, wherein $R^2$ and $R^3$ are each independently alkyl, cycloalkyl, cycloalkylalkyl, aryl, aralkyl, heterocycloalkyl, heterocycloalkylalkyl, heteroaryl, or heteroaralkyl.

38. A compound according to claim 37, wherein $R^2$ and $R^3$ are each independently alkyl or aralkyl.

39. A compound according to claim 38, wherein $R^2$ and $R^3$ are each independently $C_1$-$C_3$alkyl or $C_6$aryl$C_1$alkyl.

40. A compound according to claim 39, wherein $R^2$ and $R^3$ are each methyl.

41. A compound according to claim 39, wherein $R^2$ is methyl and $R^3$ is benzyl.

42. A compound according to claim 36, wherein $R^2$ and $R^3$, when taken together with the nitrogen atom to which they are attached, form a 3- to 8-membered heterocycloalkyl ring.

43. A compound according to claim 42, wherein $R^2$ and $R^3$, when taken together with the nitrogen atom to which they are attached, form a 4- to 6-membered heterocycloalkyl ring.

44. A compound according to claim 43, wherein $R^2$ and $R^3$ taken together with the nitrogen atom to which they are attached, form a piperidine, pyrrolidine, or morpholine ring, each optionally substituted.

45. A compound according to claim 44, wherein $R^2$ and $R^3$ taken together with the nitrogen atom to which they are attached, form a piperidine or pyrrolidine ring, each substituted with hydroxy.

46. A compound according to claim 44, wherein $R^2$ and $R^3$ taken together with the nitrogen atom to which they are attached, form a morpholine ring.

47. A compound according to claim 2, selected from the group consisting of:
4-(methylamino)-3-(morpholinosulfonyl)-N-(1,3,3-trimethylbicyclo[2.2.1]heptan-2-yl)benzamide;
3-(N,N-dimethylsulfamoyl)-4-(methylamino)-N-(1,3,3-trimethyl-bicyclo[2.2.1]-heptan-2-yl)benzamide;
N-(bicyclo-[2.2.1]heptan-2-yl)-4-(methylamino)-3-(morpholinosulfonyl)benzamide
N-(6-methoxy-1,1-dimethyl-1,2,3,4-tetrahydronaphthalen-2-yl)-4-(methylamino)-3-(morpholinosulfonyl)benzamide;
N-(5-methyl-3-phenylisoxazol-4-yl)-4-(methylamino)-3-(morpholinosulfonyl)benzamide;
3-(isoindolin-2-ylsulfonyl)-4-(methylamino)-N-(1,3,3-trimethyl-bicyclo[2.2.1]heptan-2-yl)benzamide;
N-(bicyclo[2.2.1]heptan-2-yl)-3-(isoindolin-2-ylsulfonyl)-4-(methylamino)benzamide;
N-(7,7-dimethylbicyclo[2.2.1]heptan-2-yl)-3-(isoindolin-2-ylsulfonyl)-4-(methylamino)benzamide;
3-(1,3-dihydroisoindole-2-sulfonyl)-N-[1-(3-hydroxy-adamantan-1-yl)-ethyl]-4-methylaminobenzamide;
3-(isoindolin-2-ylsulfonyl)-4-(methylamino)-N-neopentylbenzamide;
3-(isoindolin-2-ylsulfonyl)-4-(methylamino)-N-(1-phenylethyl)benzamide;
3-(isoindolin-2-ylsulfonyl)-4-(methylamino)-N-((1-phenylcyclopentyl)methyl)benzamide;
N-(1-ethylpiperidin-3-yl)-3-(isoindolin-2-ylsulfonyl)-4-(methylamino)benzamide
3-(isoindolin-2-ylsulfonyl)-4-(methylamino)-N-(1-morpholinobutan-2-yl)benzamide;
3-(N-(2-methoxyethyl)-N-methylsulfamoyl)-4-(methylamino)-N-(1,3,3-trimethylbicyclo[2.2.1]heptan-2-yl)benzamide;
methyl 2-(N-methyl-2-(methylamino)-5-(1,3,3-trimethylbicyclo[2.2.1 ]heptan-2-yl-carbamoyl)phenylsulfonamido)acetate;
methyl 2-(5-(bicyclo[2.2.1]heptan-2-ylcarbamoyl)-N-methyl-2-(methylamino)phenylsulfonamido)acetate;
methyl 2-(5-(7,7-dimethylbicyclo-[2.2.1]heptan-2-ylcarbamoyl)-N-methyl-2-(methylamino)phenylsulfonamido)acetate;
({5-[1-(3-hydroxyadamantan-1-yl)-ethylcarbamoyl]-2-methylaminobenzenesulfonyl}methylamino)acetic acid methyl ester;
methyl 2-(N-methyl-2-(methylamino)-5-(neopentylcarbamoyl)phenylsulfonamido)acetate;
methyl 2-(N-methyl-2-(methylamino)-5-(1-phenylethylcarbamoyl)phenylsulfonamido)acetate;
methyl 2-(N-methyl-2-(methylamino)-5-((1-phenylcyclopentyl)methylcarbamoyl)phenylsulfonamido)acetate;
methyl 2-(N-methyl-5-(8-methyl-8-azabicyclo[3.2.1]octan-3-ylcarbamoyl)-2-(methylamino)phenylsulfonamido)acetate;
3-(azetidin-1-ylsulfonyl)-4-(methylamino)-N-(1,3,3-trimethylbicyclo-[2.2.1]heptan-2-yl)benzamide;
4-(2-(dimethylamino)ethylamino)-3-(morpholinosulfonyl)-N-(1,3,3-trimethylbicyclo-[2.2.1]heptan-2-yl)benzamide;

4-(2-aminoethylamino)-3-(morpholinosulfonyl)-N-(1,3,
3-trimethylbicyclo[2.2.1]-heptan-2-yl)benzamide;
4-morpholino-3-(morpholinosulfonyl)-N-(1,3,3-trimethylbicyclo[2.2.1]heptan-2-yl)-benzamide;
4-(2-methoxyethylamino)-3-(morpholinosulfonyl)-N-(1,
3,3-trimethylbicyclo[2.2.1]-heptan-2-yl)benzamide;
4-(dimethylamino)-3-(morpholinosulfonyl)-N-(1,3,3-trimethylbicyclo[2.2.1]heptan-2-yl)benzamide;
4-(ethylamino)-3-(morpholinosulfonyl)-N-(1,3,3-trimethylbicyclo[2.2.1]heptan-2-yl)benzamide;
4-(isopropylamino)-3-(morpholinosulfonyl)-N-(1,3,3-trimethylbicyclo[2.2.1]heptan-2-yl)benzamide; and
4-amino-3-(morpholinosulfonyl)-N-(1,3,3-trimethylbicyclo[2.2.1]heptan-2-yl)-benzamide;
or a pharmaceutically acceptable salt thereof.

48. A compound according to claim 2, selected from the group consisting of:
4-(methylamino)-3-(morpholinosulfonyl)-N-((1S,4R)-1,
3,3-trimethylbicyclo[2.2.1]-heptan-2-yl)benzamide;
3-(N,N-dimethylsulfamoyl)-4-(methylamino)-N-((1S,
4R)-1,3,3-trimethyl-bicyclo-[2.2.1]heptan-2-yl)benzamide;
N-((1R,2R,4S)-bicyclo[2.2.1]heptan-2-yl)-4-(methylamino)-3-(morpholinosulfonyl)benzamide;
N-(6-methoxy-1,1-dimethyl-1,2,3,4-tetrahydronaphthalen-2-yl)-4-(methylamino)-3-(morpholinosulfonyl)benzamide;
N-(5-methyl-3-phenylisoxazol-4-yl)-4-(methylamino)-3-(morpholinosulfonyl)benzamide;
3-(isoindolin-2-ylsulfonyl)-4-(methylamino)-N-((1S,4R)-1,3,3-trimethyl-bicyclo-[2.2.1]heptan-2-yl)benzamide;
N-((1R,2R,4S)-bicyclo[2.2.1]heptan-2-yl)-3-(isoindolin-2-ylsulfonyl)-4-(methylamino)benzamide;
N-((1R,2S,4R)-7,7-dimethylbicyclo[2.2.1]heptan-2-yl)-3-(isoindolin-2-ylsulfonyl)-4-(methylamino)benzamide;
3-(1,3-dihydroisoindole-2-sulfonyl)-N-[1-(3-hydroxyadamantan-1-yl)-ethyl]-4-methylaminobenzamide;
3-(isoindolin-2-ylsulfonyl)-4-(methylamino)-N-neopentylbenzamide
3-(isoindolin-2-ylsulfonyl)-4-(methylamino)-N-(1-phenylethyl)benzamide;
3-(isoindolin-2-ylsulfonyl)-4-(methylamino)-N-((1-phenylcyclopentyl)methyl)benzamide;
N-(1-ethylpiperidin-3-yl)-3-(isoindolin-2-ylsulfonyl)-4-(methylamino)benzamide;
3-(isoindolin-2-ylsulfonyl)-4-(methylamino)-N-(1-morpholinobutan-2-yl)benzamide;
3-(N-(2-methoxyethyl)-N-methylsulfamoyl)-4-(methylamino)-N-((1S,4R)-1,3,3-trimethylbicyclo[2.2.1]heptan-2-yl)benzamide;
methyl 2-(N-methyl-2-(methylamino)-5-((1S,4R)-1,3,3-trimethylbicyclo[2.2.1]-heptan-2-ylcarbamoyl)phenylsulfonamido)acetate;
methyl 2-(5-((1R,2R,4S)-bicyclo[2.2.1]heptan-2-ylcarbamoyl)-N-methyl-2-(methylamino)phenylsulfonamido)acetate;
methyl 2-(5-((1R,2S,4R)-7,7-dimethylbicyclOl[2.2.1]heptan-2-ylcarbamoyl)-N-methyl-2-(methylamino)phenylsulfonamido)acetate;
({5-[1-(3-hydroxyadamantan-1-yl)-ethylcarbamoyl]-2-methylaminobenzenesulfonyl}methylamino)acetic acid methyl ester;
methyl 2-(N-methyl-2-(methylamino)-5-(neopentylcarbamoyl)phenylsulfonamido)acetate;
methyl 2-(N-methyl-2-(methylamino)-5-(1-phenylethylcarbamoyl)phenylsulfonamido)acetate;
methyl 2-(N-methyl-2-(methylamino)-5-((1-phenylcyclopentyl)methylcarbamoyl)phenylsulfonamido)acetate;
methyl 2-(N-methyl-5-(8-methyl-8-azabicyclo-[3.2.1]octan-3-ylcarbamoyl)-2-(methylamino)-phenylsulfonamido)acetate;
3-(azetidin-1-ylsulfonyl)-4-(methylamino)-N-((1S,4R)-1,3,3-trimethylbicyclo-[2.2.1]heptan-2-yl)benzamide;
4-(2-(dimethylamino)ethylamino)-3-(morpholinosulfonyl)-N-((1S,4R)-1,3,3-trimethylbicyclo[2.2.1]heptan-2-yl)benzamide;
4-(2-aminoethylamino)-3-(morpholinosulfonyl)-N-((1S,4R)-1,3,3-trimethylbicyclo[2.2.1]heptan-2-yl)benzamide;
4-morpholino-3-(morpholinosulfonyl)-N-((1S,4R)-1,3,3-trimethylbicyclo[2.2.1]-heptan-2-yl)benzamide;
4-(2-methoxyethylamino)-3-(morpholinosulfonyl)-N-((1S,4R)-1,3,3-trimethylbicyclo-[2.2.1]heptan-2-yl)benzamide;
4-(dimethylamino)-3-(morpholinosulfonyl)-N-((1S,4R)-1,3,3-trimethyl-bicyclo-[2.2.1]heptan-2-yl)benzamide;
4-(ethylamino)-3-(morpholinosulfonyl)-N-((1S,4R)-1,3,3-trimethylbicyclo[2.2.1]-heptan-2-yl)benzamide;
4-(isopropylamino)-3-(morpholinosulfonyl)-N-((1S,4R)-1,3,3-trimethylbicyclo[2.2.1]-heptan-2-yl)benzamide; and
4-amino-3-(morpholinosulfonyl)-N-((1S,4R)-1,3,3-trimethylbicyclo[2.2.1]heptan-2-yl)benzamide;
or a pharmaceutically acceptable salt thereof.

49. A compound according to claim 47, selected from the group consisting of:
4-(methylamino)-3-(morpholinosulfonyl)-N-(1,3,3-trimethylbicyclo[2.2.1]heptan-2-yl)benzamide;
3-(N,N-dimethylsulfamoyl)-4-(methylamino)-N-(1,3,3-trimethylbicyclo[2.2.1]-heptan-2-yl)benzamide;
4-(2-methoxyethylamino)-3-(morpholinosulfonyl)-N-1,3,3-trimethylbicyclo[2.2.1]-heptan-2-yl)benzamide;
3-(isoindolin-2-ylsulfonyl)-4-(methylamino)-N-(1,3,3-trimethylbicyclo[2.2.1]heptan-2-yl)benzamide;
N-(bicyclo[2.2.1]heptan-2-yl)-3-(isoindolin-2-ylsulfonyl)-4-(methylamino)benzamide;
N-(7,7-dimethylbicyclo[2.2.1]heptan-2-yl)-3-(isoindolin-2-ylsulfonyl)-4-(methylamino)benzamide;
3-(1,3-dihydroisoindole-2-sulfonyl)-N-[1-(3-hydroxyadamantan-1-yl)-ethyl]-4-methylaminobenzamide;
3(N-(2-methoxyethyl)-N-methylsulfamoyl)-4-(methylamino)-N-(1,3,3-trimethylbicyclo[2.2.1]heptan-2-yl)benzamide;
4-(2-(dimethylamino)ethylamino)-3-(morpholinosulfonyl)-N-(1,3,3-trimethylbicyclo-[2.2.1]heptan-2-yl)benzamide; and
4-(dimethylamino)-3-(morpholinosulfonyl)-N-(1,3,3-trimethylbicyclo[2.2.1]heptan-2-yl)benzamide;
or a pharmaceutically acceptable salt thereof.

50. A compound according to claim 48, selected from the group consisting of:
4-(methylamino)-3-(morpholinosulfonyl)-N-((1S,4R)-1,3,3-trimethylbicyclo[2.2.1]-heptan-2-yl)benzamide;
3-(N,N-dimethylsulfamoyl)-4-(methylamino)-N-((1S,4R)-1,3,3-trimethyl-bicyclo-[2.2.1]heptan-2-yl)benzamide;
4-(2-methoxyethylamino)-3-(morpholinosulfonyl)-N-((1S,4R)-1,3,3-trimethyl-bicyclo[2.2.1]heptan-2-yl)benzamide;
3-(isoindolin-2-ylsulfonyl)-4-(methylamino)-N-((1S,4R)-1,3,3-trimethylbicyclo-[2.2.1]heptan-2-yl)benzamide;
N-((1R,2R,4S)-bicyclo[2.2.1]heptan-2-yl)-3-(isoindolin-2-ylsulfonyl)-4-(methylamino)benzamide;

N-((1R,2S,4R)-7,7-dimethylbicyclo[2.2.1]heptan-2-yl)-3-(isoindolin-2-ylsulfonyl)-4-(methylamino)benzamide;

3-(1,3-dihydroisoindole-2-sulfonyl)-N-[1-(3-hydroxy-adamantan-1-yl)ethyl]-4-methylaminobenzamide;

3-(N-(2-methoxyethyl)-N-methylsulfamoyl)-4-(methylamino)-N-((1S,4R)-1,3,3-trimethylbicyclo[2.2.1]heptan-2-yl)benzamide;

4-(2-(dimethylamino)ethylamino)-3-(morpholinosulfonyl)-N-((1S,4R)-1,3,3-trimethylbicyclo[2.2.1]heptan-2-yl)benzamide; and 4-(dimethylamino)-3-(morpholinosulfonyl)-N-((1S,4R)-1,3,3-trimethyl-bicyclo-[2.2.1]heptan-2-yl)benzamide;

or a pharmaceutically acceptable salt thereof.

51. A compound according to claim 49, selected from the group consisting of:

4-(methylamino)-3-(morpholinosulfonyl)-N-(1,3,3-trimethylbicyclo[2.2.1]heptan-2-yl)benzamide;

4-(2-methoxyethylamino)-3-(morpholinosulfonyl)-N-(1,3,3-trimethylbicyclo[2.2.1]-heptan-2-yl)benzamide;

3-(N,N-dimethylsulfamoyl)-4-(methylamino)-N-(1,3,3-trimethyl-bicyclo[2.2.1]-heptan-2-yl)benzamide;

3-(isoindolin-2-ylsulfonyl)-4-(methylamino)-N-(1,3,3-trimethyl-bicyclo[2.2.1]heptan-2-yl)benzamide; and 4-(dimethylamino)-3-(morpholinosulfonyl)-N-(1,3,3-trimethylbicyclo[2.2.1]heptan-2-yl)benzamide;

or a pharmaceutically acceptable salt thereof.

52. A compound according to claim 50, selected from the group consisting of:

4-(methylamino)-3-(morpholinosulfonyl)-N-((1S,4R)-1,3,3-trimethylbicyclo[2.2.1]-heptan-2-yl)benzamide;

3-(N,N-dimethylsulfamoyl)-4-(methylamino)-N-((1S,4R)-1,3,3-trimethylbicyclo-[2.2.1]heptan-2-yl)benzamide;

4-(2-methoxyethylamino)-3-(morpholinosulfonyl)-N-((1S,4R)-1,3,3-trimethylbicyclo-[2.2.1]heptan-2-yl)benzamide;

3-(isoindolin-2-ylsulfonyl)-4-(methylamino)-N-((1S,4R)-1,3,3-trimethylbicyclo-[2.2.1]heptan-2-yl)benzamide; and 4-(dimethylamino)-3-(morpholinosulfonyl)-N-((1S,4R)-1,3,3-trimethylbicyclo-[2.2.1]heptan-2-yl)benzamide;

or a pharmaceutically acceptable salt thereof.

53. A compound according to claim 2, selected from the group consisting of:

3-(N,N-dimethylsulfamoyl)-4-(methylamino)-N-(1,3,3-trimethylbicyclo[2.2.1]heptan-2-yl)benzamide;

N-(bicyclo[2.2.1]heptan-2-yl)-3-(N,N-dimethylsulfamoyl)-4-(methylamino)benzamide;

3-(4-hydroxypiperidin-1-ylsulfonyl)-4-(methylamino)-N-(1,3,3-trimethylbicyclo-[2.2.1]heptan-2-yl)benzamide;

3-(3-hydroxypiperidin-1-ylsulfonyl)-4-(methylamino)-N-(1,3,3-trimethylbicyclo-[2.2.1]heptan-2-yl)benzamide;

4-(methylamino)-3-(pyrrolidin-1-ylsulfonyl)-N-(1,3,3-trimethylbicyclo[2.2.1]heptan-2-yl)benzamide;

N-(bicyclo[2.2.1]heptan-2-yl)-4-(methylamino)-3-(pyrrolidin-1-ylsulfonyl)benzamide;

N-(3,3-dimethylbutan-2-yl)-4-(methylamino)-3-(pyrrolidin-1-ylsulfonyl)benzamide;

4-(methylamino)-3-(pyrrolidin-1-ylsulfonyl)-N-(3,3,5-trimethylcyclohexyl)benzamide;

3-(3-hydroxypyrrolidin-1-ylsulfonyl)-4-(methylamino)-N-(1,3,3-trimethylbicyclo-[2.2.1]heptan-2-yl)benzamide;

N-adamantan-1-yl-4-methylamino-3-(morpholine-4-sulfonyl)benzamide;

3-(N-tert-butylsulfamoyl)-4-(methylamino)-N-(1,3,3-trimethylbicyclo[2.2.1]heptan-2-yl)benzamide;

3-(N-ethyl-N-methyl-sulfamoyl)-4-(methylamino)-N-(1,3,3-trimethylbicyclo[2.2.1]-heptan-2-yl)benzamide;

methyl 3-(2-(morpholinosulfonyl)-4-(1,3,3-trimethylbicyclo[2.2.1]heptan-2-ylcarbamoyl)phenyl)amino)propanoate;

4-(2-methoxyethylamino)-3-(pyrrolidin-1-ylsulfonyl)-N-(1,3,3-trimethylbicyclo-[2.2.1]heptan-2-yl)benzamide;

4-(benzylamino)-3-(pyrrolidin-1-ylsulfonyl)-N-(1,3,3-trimethylbicyclo[2.2.1]heptan-2-yl)benzamide;

3-(N,N-dimethylsulfamoyl)-4-(2-methoxyethylamino)-N-(1,3,3-trimethylbicyclo-[2.2.1]heptan-2-yl)benzamide;

3-(N-(2-hydroxyethyl)-N-methylsulfamoyl)-4-(2-methoxyethylamino)-N-(1,3,3-trimethylbicyclo[2.2.1]heptan-2-yl)benzamide;

4-amino-3-(N-tert-butylsulfamoyl)-N-(1,3,3-trimethylbicyclo[2.2.1]heptan-2-yl)-benzamide; and 3-(N-benzyl-N-methylsulfamoyl)-4-(2-(dimethylamino)ethylamino)-N(1,3,3-trimethylbicyclo[2.2.1]heptan-2-yl)benzamide;

or a pharmaceutically acceptable salt thereof.

54. A compound according to claim 2, selected from the group consisting of:

3-(N,N-dimethylsulfamoyl)-4-(methylamino)-N-((1S,4R)-1,3,3-trimethylbicyclo-[2.2.1]heptan-2-yl)benzamide;

N-((1R,2R,4S)-bicyclo[2.2.1]heptan-2-yl)-3-(N,N-dimethylsulfamoyl)-4-(methylamino)benzamide;

3-(4-hydroxypiperidin-1-ylsulfonyl)-4-(methylamino)-N-((1S,4R)-1,3,3-trimethylbicyclo[2.2.1]heptan-2-yl)benzamide;

3-(3-hydroxypiperidin-1-ylsulfonyl)-4-(methylamino)-N-((1S,4R)-1,3,3-trimethylbicyclo[2.2.1]heptan-2-yl)benzamide;

4-(methylamino)-3-(pyrrolidin-1-ylsulfonyl)-N-((1S,4R)-1,3,3-trimethylbicyclo-[2.2.1]heptan-2-yl)benzamide;

N-((1R,2R,4S)-bicyclo[2.2.1]heptan-2-yl)-4-(methylamino)-3-(pyrrolidin-1-ylsulfonyl)benzamide;

N-(3,3-dimethylbutan-2-yl)-4-(methylamino)-3-(pyrrolidin-1-ylsulfonyl)benzamide;

4-(methylamino)-3-(pyrrolidin-1-ylsulfonyl)-N-(3,3,5-trimethylcyclohexyl)benzamide;

3-((R)-3-hydroxypyrrolidin-1-ylsulfonyl)-4-(methylamino)-N-((1S,4R)-1,3,3-trimethylbicyclo[2.2.1]heptan-2-yl)benzamide;

3-((S)-3-hydroxypyrrolidin-1-ylsulfonyl)-4-(methylamino)-N-((1S,4R)-1,3,3-trimethylbicyclo[2.2.1]heptan-2-yl)benzamide;

N-adamantan-1-yl-4-methylamino-3-(morpholine-4-sulfonyl)benzamide;

3-(N-tert-butylsulfamoyl)-4-(methylamino)-N-((1S,4R)-1,3,3-trimethylbicyclo[2.2.1]-heptan-2-yl)benzamide;

3-(N-ethyl-N-methylsulfamoyl)-4-(methylamino)-N-((1S,4R)-1,3,3-trimethylbicyclo-[2.2.1]heptan-2-yl)benzamide;

methyl 3-(2-(morpholinosulfonyl)-4-((1S,4R)-1,3,3-trimethylbicyclo[2.2.1]heptan-2-ylcarbamoyl)phenyl)amino)propanoate;

4-(2-methoxyethylamino)-3-(pyrrolidin-1-ylsulfonyl)-N-((1S,4R)-1,3,3-trimethylbicyclo[2.2.1]heptan-2-yl)benzamide;

4-(benzylamino)-3-(pyrrolidin-1-ylsulfonyl)-N-((1S,4R)-1,3,3-trimethylbicyclo[2.2.1]heptan-2-yl)benzamide;

3-(N,N-dimethylsulfamoyl)-4-(2-methoxyethylamino)-
N-((1S,4R)-1,3,3-trimethylbicyclo[2.2.1]heptan-2-yl)
benzamide;

3-(N-(2-hydroxyethyl)-N-methylsulfamoyl)-4-(2-methoxyethylamino)-N-((1S,4R)-1,3,3-trimethylbicyclo
[2.2.1]heptan-2-yl)benzamide;

4-amino-3-(N-tert-butylsulfamoyl)-N-((1S,4R)-1,3,3-trimethylbicyclo[2.2.1]heptan-2-yl)benzamide; and 3-(N-benzyl-N-methylsulfamoyl)-4-(2-(dimethylamino)
ethylamino)-N-((1S,4R)-1,3,3-trimethylbicyclo[2.2.1]
heptan-2-yl)benzamide;

or a pharmaceutically acceptable salt thereof.

55. A compound according to claim 53, selected from the group consisting of:

3-(N,N-dimethylsulfamoyl)-4-(methylamino)-N-(1,3,3-trimethylbicyclo[2.2.1]heptan-2-yl)benzamide;

N-adamantan-1-yl-4-methylamino-3-(morpholine-4-sulfonyl)-benzamide ({5-[1-(3-hydroxyadamantan-1-yl)-ethyl-carbamoyl]-2-methylaminobenzene-sulfonyl}-methylamino)acetic
acid methyl ester;

3-(3-hydroxypiperidin-1-ylsulfonyl)-4-(methylamino)-N-(1,3,3-trimethylbicyclo-[2.2.1]heptan-2-yl)benzamide;

3-(3-hydroxypyrrolidin-1-ylsulfonyl)-4-(methylamino)-
N-(1,3,3-trimethylbicyclo-[2.2.1]heptan-2-yl)benzamide;

4-(benzylamino)-3-(pyrrolidin-1-ylsulfonyl)-N-(1,3,3-trimethylbicyclo[2.2.1]heptan-2-yl)benzamide;

3-(N,N-dimethylsulfamoyl)-4-(2-methoxyethylamino)-
N-(1,3,3-trimethylbicyclo-[2.2.1]heptan-2-yl)benzamide;

N-(3,3-dimethylbutan-2-yl)-4-(methylamino)-3-(pyrrolidin-1-ylsulfonyl)benzamide;

3-(N-ethyl-N-methylsulfamoyl)-4-(methylamino)-N-(1,3,3-trimethylbicyclo[2.2.1]-heptan-2-yl)benzamide; and 4-(2-methoxyethylamino)-3-(pyrrolidin-1-ylsulfonyl)-N-(1,3,3-trimethylbicyclo-[2.2.1]heptan-2-yl)benzamide;

or a pharmaceutically acceptable salt thereof.

56. A compound according to claim 54, selected from the group consisting of:

3-(N,N-dimethylsulfamoyl)-4-(methylamino)-N-((1S,
4R)-1,3,3-trimethylbicyclo-[2.2.1]heptan-2-yl)benzamide;

N-adamantan-1-yl-4-methylamino-3-(morpholine-4-sulfonyl)-benzamide;

({5-[1-(3-hydroxyadamantan-1-yl)ethylcarbamoyl]-2-methylaminobenzene-sulfonyl}methylamino)acetic
acid methyl ester;

3-(3-hydroxypiperidin-1-ylsulfonyl)-4-(methylamino)-N-((1S,4R)-1,3,3-trimethyl-bicyclo[2.2.1]heptan-2-yl)
benzamide;

3-((S)-3-hydroxypyrrolidin-1-ylsulfonyl)-4-(methylamino)-N-((1S,4R)-1,3,3-trimethylbicyclo[2.2.1]heptan-2-yl)benzamide;

4-(benzylamino)-3-(pyrrolidin-1-ylsulfonyl)-N-((1S,4R)-1,3,3-trimethylbicyclo-[2.2.1]heptan-2-yl)benzamide;

3-(N,N-dimethylsulfamoyl)-4-(2-methoxyethylamino)-
N-((1S,4R)-1,3,3-trimethylbicyclo[2.2.1]heptan-2-yl)
benzamide;

N-(3,3-dimethylbutan-2-yl)-4-(methylamino)-3-(pyrrolidin-1-ylsulfonyl)benzamide;

3-(N-ethyl-N-methylsulfamoyl)-4-(methylamino)-N-((1S,4R)-1,3,3-trimethylbicyclo[2.2.1]heptan-2-yl)
benzamide; and 4-(2-methoxyethylamino)-3-(pyrrolidin-1-ylsulfonyl)-N-((1S,4R)-1,3,3-trimethylbicyclo[2.2.1]heptan-2-yl)
benzamide;

or a pharmaceutically acceptable salt thereof.

57. A compound according to claim 55, selected from the group consisting of:

3-(N,N-dimethylsulfamoyl)-4-(methylamino)-N-(1,3,3-trimethylbicyclo[2.2.1]heptan-2-yl)benzamide;

N-adamantan-1-yl-4-methylamino-3-(morpholine-4-sulfonyl)-benzamide;

({5-[1-(3-hydroxyadamantan-1-yl)ethylcarbamoyl]-2-methylaminobenzenesulfonyl}-methylamino)acetic
acid methyl ester;

3-(3-hydroxypiperidin-1-ylsulfonyl)-4-(methylamino)-N-(1,3,3-trimethylbicyclo-[2.2.1]heptan-2-yl)benzamide;
and 3-(3-hydroxypyrrolidin-1-ylsulfonyl)-4-(methylamino)-
N-(1,3,3-trimethylbicyclo-[2.2.1]heptan-2-yl)benzamide;

or a pharmaceutically acceptable salt thereof.

58. A compound according to claim 56, selected from the group consisting of:

3-(N,N-dimethylsulfamoyl)-4-(methylamino)-N-((1S,
4R)-1,3,3-trimethylbicyclo-[2.2.1]heptan-2-yl)benzamide;

N-adamantan-1-yl-4-methylamino-3-(morpholine-4-sulfonyl)benzamide;

({5-[1-(3-hydroxyadamantan-1-yl)ethylcarbamoyl]-2-methylaminobenzenesulfonyl}-methylamino)acetic
acid methyl ester;

3-(3-hydroxypiperidin-1-ylsulfonyl)-4-(methylamino)-N-((1S,4R)-1,3,3-trimethylbicyclo[2.2.1]heptan-2-yl)
benzamide; and 3-((S)-3-hydroxypyrrolidin-1-ylsulfonyl)-4-(methylamino)-N-((1S,4R)-1,3,3-trimethylbicyclo[2.2.1]heptan-2-yl)benzamide;

or a pharmaceutically acceptable salt thereof.

59. A compound according to claim 57, selected from the group consisting of:

3-(N,N-dimethylsulfamoyl)-4-(methylamino)-N-(1,3,3-trimethylbicyclo[2.2.1]heptan-2-yl)benzamide; and N-adamantan-1-yl-4-methylamino-3-(morpholine-4-sulfonyl)benzamide;

or a pharmaceutically acceptable salt thereof.

60. A compound according to claim 58, selected from the group consisting of:

3-(N,N-dimethylsulfamoyl)-4-(methylamino)-N-((1S,
4R)-1,3,3-trimethylbicyclo-[2.2.1]heptan-2-yl)benzamide; and N-adamantan-1-yl-4-methylamino-3-(morpholine-4-sulfonyl)benzamide or a pharmaceutically acceptable salt thereof.

61. A compound according to claim 51 which is 4-(methylamino)-3-(morpholinosulfonyl)-N-(1,3,3-trimethylbicyclo[2.2.1]heptan-2-yl)benzamide. or a pharmaceutically acceptable salt thereof.

62. A compound according to claim 61 which is 4-(methylamino)-3-(morpholinosulfonyl)-N-((1S,4R)-1,3,3-trimethylbicyclo[2.2.1]heptan-2-yl)benzamide or a pharmaceutically acceptable salt thereof.

63. A pharmaceutical composition, comprising:
a pharmaceutically acceptable carrier; and a compound of formula I:

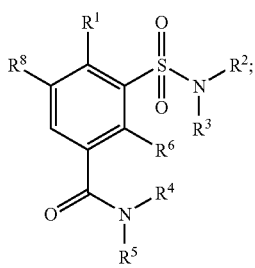

wherein:

$R^1$ is $NR^yR^z$;

each $R^x$, $R^y$ and $R^z$ is independently H, alkyl, cycloalkyl, cycloalkylalkyl, aryl, aralkyl, heterocycloalkyl, heterocycloalkylalkyl, heteroaryl, or heteroaralkyl; or and $R^z$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N($R^{10}$)—;

$R^2$ and $R^3$ are each independently H, alkyl, cycloalkyl, cycloalkylalkyl, aryl, aralkyl, heterocycloalkyl, heterocycloalkylalkyl, heteroaryl, or heteroaralkyl, provided that at least one of $R^2$ and $R^3$ is other than H; or $R^2$ and $R^3$, when taken together with the nitrogen atom to which they are attached, form a 3- to 8-membered heterocycloalkyl ring in which 1 or 2 of the heterocycloalkyl ring carbon atoms independently may each be optionally replaced by —O—, —S—, —N($R^9$)—, —N($R^{10}$)—C(=O)—, or —C(=O)—N ($R^{10}$)—;

$R^4$ is H or alkyl;

$R^5$ is:

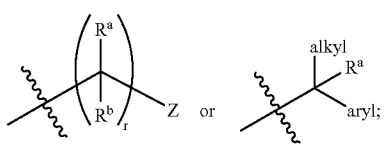

Z is

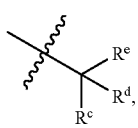

a 1 or 2 heteroatom containing heteroaryl, or a 1 or 2 heteroatom containing heterocycloalkyl, wherein each heteroatom of said heteroaryl or heterocycloalkyl group is independently selected from the group consisting of N, O, or S;

each $R^a$ and $R^b$ is independently H or alkyl;

$R^c$ is H, alkyl, or aryl;

$R^d$ and $R^e$ are each independently H or alkyl, with the proviso that at least two of $R^c$, $R^d$, and $R^e$ are other than H; or $R^d$ and $R^e$, taken together with the carbon atom to which they are attached, form a carbocyclic or heterocyclic ring; or $R^c$, $R^d$, and $R^e$, taken together with the carbon atom to which they are attached, form a bicycloalkyl, tricycloalkyl, heterobicyclic, or heterotricyclic ring;

$R^6$ and $R^8$ are each independently H or alkyl;

each $R^9$ is independently H, alkyl, aryl, —C(=O)—$R^{11}$, —C(=O)—O$R^{11}$, —[C($R^{11}$)($R^{11}$)]$_s$—C(=O)—O$R^{11}$, —SO$_2$$R^{11}$, or —C(=O)N($R^{11}$)$R^{11}$;

each $R^{10}$ is independently H, alkyl, or aryl;

each $R^{11}$ is independently H or alkyl;

r is 0, 1, 2, or 3; and s is 1, 2, 3, or 4;

with the provisos that:

(1) when $R^d$ and $R^e$ are each independently H or alkyl, then $R^c$ is H or alkyl; and (2) when $R^c$ is aryl, then $R^d$ and $R^e$, taken together with the carbon atom to which they are attached, form a carbocyclic or heterocyclic ring;

or a pharmaceutically acceptable salt thereof.

64. A pharmaceutical composition according to claim 63, wherein $R^6$ and $R^8$ are each H.

65. A pharmaceutical composition according to claim 64, further comprising at least one cannabinoid.

66. A pharmaceutical composition according to claim 65, wherein the cannabinoid is $\Delta^9$-tetrahydrocannabinol or cannabidiol.

67. A pharmaceutical composition according to claim 64, further comprising at least one opioid.

68. A pharmaceutical composition according to claim 67, wherein said opioid is selected from the group consisting of alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene; sufentanil and tramadol, and mixtures thereof.

69. A pharmaceutical composition according to claim 64, further comprising at least one analgesic.

70. A pharmaceutical composition according to claim 69, wherein the analgesic is aspirin, acetaminophen, ibuprophen, naproxen, or a mixture thereof.

71. A pharmaceutical composition according to claim 64, further comprising at least one agent selected from the group consisting of an anti-seizure agent, an anti-depressant, an anti-Parkinson's agent, and mixtures thereof; wherein:

said anti-seizure agent is selected from the group consisting of carbamazepine, gabapentin, lamotrigine, phenytoin, and a mixture thereof;

said anti-depressant is amitryptiline; and said anti-Parkinson's agent is selected from the group consisting of deprenyl, amantadine, levodopa, carbidopa, and a mixture thereof.

72. A compound according to claim 2, which is 3-(morpholinosulfonyl)-4-(1H-pyrazol-1-yl)-N-((1S,4R)-1,3,3-trimethyl-bicyclo[2.2.1]heptan-2-yl)benzamide.

73. A compound according to claim 2, which is 4-((2-methoxyethyl)(methyl)amino)-3-(morpholinosulfonyl)-N-((1S,4R)-1,3,3-trimethylbicyclo[2.2.1]heptan-2-yl)benzamide.

74. A compound according to claim 2, which is 4-((3-methoxypropyl)amino)-3-(morpholinosulfonyl)-N-((1S,4R)-1,3,3-trimethylbicyclo[2.2.1]heptan-2-yl)benzamide.

* * * * *